US010258687B2

(12) United States Patent
Mathiesen et al.

(10) Patent No.: US 10,258,687 B2
(45) Date of Patent: Apr. 16, 2019

(54) DEVELOPMENT OF METHODS FOR PRODUCTION OF A WHOLE VIRUS VACCINE CANDIDATE STOCK AND NOVEL ADAPTIVE MUTATIONS IN HEPATITIS C VIRUS

(71) Applicant: Hvidovre Hospital, Hvidovre (DK)

(72) Inventors: Christian Kjærulff Mathiesen, Kongens Lyngby (DK); Tanja Bertelsen Jensen, Copenhagen N (DK); Jens Bukh, Præstø (DK); Judith Margarete Gottwein, Frederiksberg C (DK)

(73) Assignee: HVIDOVRE HOSPITAL, Hvidovre (DK)

( * ) Notice: Subject to any disclaimer, the term of this patent is extended or adjusted under 35 U.S.C. 154(b) by 0 days.

(21) Appl. No.: 15/126,394

(22) PCT Filed: Apr. 16, 2015

(86) PCT No.: PCT/DK2015/050097
§ 371 (c)(1),
(2) Date: Sep. 15, 2016

(87) PCT Pub. No.: WO2015/158353
PCT Pub. Date: Oct. 22, 2015

(65) Prior Publication Data
US 2017/0274067 A1    Sep. 28, 2017

(30) Foreign Application Priority Data

Apr. 16, 2014  (DK) .................................. 2014 70221

(51) Int. Cl.
A61K 39/29      (2006.01)
C07K 14/005    (2006.01)
C12N 7/00        (2006.01)

(52) U.S. Cl.
CPC ............ A61K 39/29 (2013.01); C07K 14/005 (2013.01); C12N 7/00 (2013.01); C12N 2770/24221 (2013.01); C12N 2770/24222 (2013.01); C12N 2770/24234 (2013.01); C12N 2770/24251 (2013.01); C12N 2770/24261 (2013.01)

(58) Field of Classification Search
None
See application file for complete search history.

(56) References Cited

U.S. PATENT DOCUMENTS

| 8,454,974 | B2 | 6/2013 | Scheel et al. |
| 8,506,969 | B2 | 8/2013 | Gottwein et al. |
| 8,563,706 | B2 | 10/2013 | Scheel et al. |
| 8,569,472 | B2 | 10/2013 | Gottwein et al. |
| 8,618,275 | B2 | 12/2013 | Jensen et al. |
| 8,663,653 | B2 | 3/2014 | Gottwein et al. |
| 8,772,022 | B2 | 7/2014 | Gottwein et al. |
| 8,846,891 | B2 | 9/2014 | Prento et al. |
| 9,382,517 | B2 | 7/2016 | Li et al. |
| 9,388,389 | B2 | 7/2016 | Scheel et al. |
| 2006/0210969 | A1* | 9/2006 | Rice .................. C12N 7/00 435/5 |
| 2009/0252755 | A1 | 10/2009 | Bukh et al. |
| 2010/0093841 | A1 | 4/2010 | Gottwein et al. |
| 2013/0243841 | A1* | 9/2013 | Kommareddy ...... A61K 39/145 424/422 |
| 2016/0244729 | A1 | 8/2016 | Li et al. |

FOREIGN PATENT DOCUMENTS

| WO | WO 2006/096459 A2 | 9/2006 |
| WO | WO 2008/125119 A1 | 10/2008 |
| WO | WO 2010/017818 A1 | 2/2010 |
| WO | WO 2010/022727 A1 | 3/2010 |
| WO | WO 2011/038737 A1 | 4/2011 |
| WO | WO 2013/139339 A1 | 9/2013 |
| WO | WO 2013/139340 A1 | 9/2013 |
| WO | WO 2015/014369 A1 | 2/2015 |
| WO | WO 2015/058772 A2 | 4/2015 |
| WO | WO 2015/158353 A1 | 10/2015 |
| WO | WO 2015/179204 A1 | 11/2015 |

OTHER PUBLICATIONS

Zolotukhin et al. Recombinant adeno-associated virus purification using novel methods improves infectious titer and yield. Gene Therapy (1999) 6, 973-985.*
Mathiesen et al. Production and characterization of high-titer serum-free cell culture grown hepatitis C virus particles of genotype 1-6.Virology458-459(2014)190-208.*
Akazawa, Daisuke et al., "Production and characterization of HCV particles from serum-free culture" Vaccine, 2011, pp. 4821-4828, vol. 29.
Akazawa, Daisuke et al., "Neutralizing Antibodies Induced by Cell Culture-Derived Hepatitis C Virus Protect Against Infection in Mice" Gastroenterology, 2013, pp. 447-455, vol. 145.
Houghton, Michael et al., "An Inactivated Hepatitis C Virus Vaccine on the Horizon?" Editorials, 2013, pp. 285-288.
Mathiesen, Christian K. et al., "Production and characterization of high-titer serum-free cell culture grown hepatitis C virus particles of genotype 1-6" Virology, 2014, pp. 190-208, vol. 458-459.
Morris, David L. et al., "Adipose Tissue Macrophages Function As Antigen-Presenting Cells and Regulate Adipose Tissue CD4$^+$ T Cells in Mice" Diabetes, Aug. 2013, pp. 2762-2772, vol. 62, No. 8.
Yao, Xiangjie et al., "Baculovirus Mediated Production of Infectious Hepatitis C Virus in Human Hepatoma Cells Stably Expressing T7 RNA Polymerase" Mol Biotechnol, 2008, pp. 186-194, vol. 40.
International Search Report for PCT/DK2015/050097 dated Sep. 30, 2015.
GenBank: AF009606.1, "Hepatitis C virus subtype 1a polyprotein gene, complete cds.", Jun. 18, 2009.

(Continued)

Primary Examiner — Nianxiang Zou
(74) Attorney, Agent, or Firm — Knobbe, Martens, Olson & Bear LLP

(57) ABSTRACT

The present invention relates to methods for obtaining a whole virus vaccine candidate stock. The present invention also relates to an inactivated whole virus vaccine candidate stock that can be used for vaccination purposes as well as development of novel high titer virus, which is the preferred virus for this technique.

4 Claims, 29 Drawing Sheets

(56) References Cited

OTHER PUBLICATIONS

Figure 1:
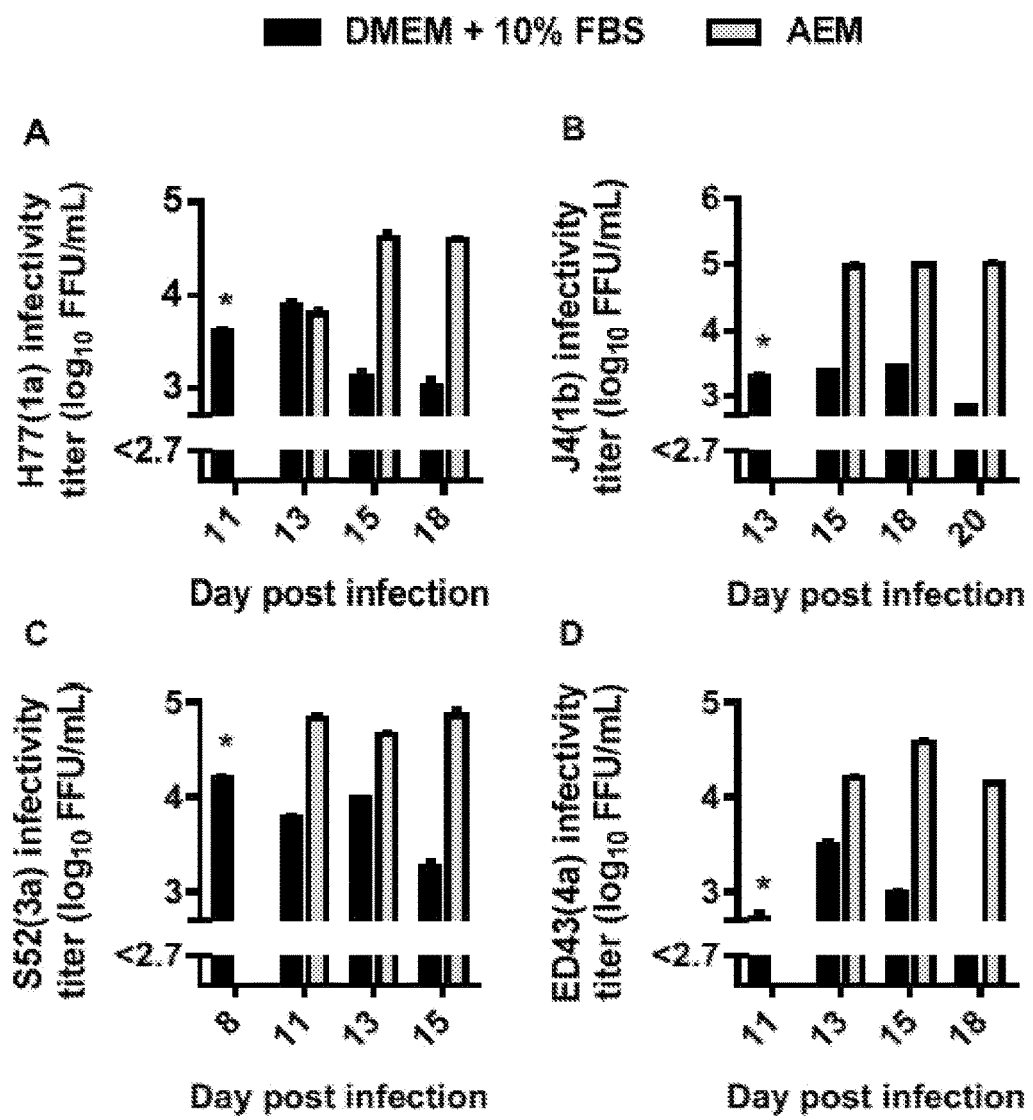

GenBank: BAD73984.1, "polyprotein, Partial [Hepatitis C virus subtype 1B]", Oct. 17, 2008.
Murayama, Asako et al., "Production of Infectious Chimeric Hepatitis C Virus Genotype 2b Harboring Minimal Regions of JFH-1" Journal of Virology, Feb. 2012, pp. 2143-2152, vol. 86, No. 4.
Scheel, Troels K. et al., "Development of JFH1-based cell culture systems for hepatitis C virus genotype 4a and evidence for cross-genotype neutralization" PNAS, Jan. 2008, pp. 997-1002, vol. 105, No. 3.
GenBank: GU814266.1, Synthetic construct Hepatitis C virus ED43 polyprotein gene, complete cds. 2010.
Altschul, Stephen F. et al., "Basic Local Alignment Search Tool" J. Mol. Bioi., 1990, pp. 403-410, vol. 215.
Altschul, Stephen F. et al., "Protein database searches for multiple alignments" Proc. Natl. Acad. Sci, Jul. 1990, pp. 5509-5513, vol. 87.
Bukh, Jens et al., "A milestone for hepatitis C virus research: A virus generated in cell culture is fully viable in vivo" PNAS, Mar. 2006, pp. 3500-3501, vol. 103, No. 10.
Bukh, Jens et al., "Challenge Pools of Hepatitis C Virus Genotypes 1-6 Prototype Strains: Replication Fitness and Pathogenicity in Chimpanzees and Human Liver-Chimeric Mouse Models" J Infect Dis., May 2010, pp. 1381-1389, vol. 201, No. 9.
Chen, N. et al., "Oxymatrine inhibits target cell infection in the HCVcc system" Chinese Journal of Hepatology, Jan. 2016, pp. 40-45, vol. 24, No. 1—Abstract.
Date, Tomoko et al., "Novel Cell Culture-Adapted Genotype 2a Hepatitis C Virus Infectious Clone" Journal of Virology, Oct. 2012, pp. 10805-10820, vol. 86, No. 19.
Engle, Ronald E. et al., "Development of a TaqMan Assay for the Six Major Genotypes of Hepatitis C Virus: Comparison With Commercial Assays" Journal of Medical Virology, 2008, pp. 72-79, vol. 80.
Gottwein, Judith M., et al., "Development and Characterization of Hepatitis C Virus Genotype 1-7 Cell Culture Systems: Role of CD81 and Scavenger Receptor Class B Type I and Effect of Antiviral Drugs" Hepatology, 2009, pp. 364-377, vol. 49, No. 2.
Gottwein, Judith M. et al., "Combination Treatment with Hepatitis C Virus Protease and NS5A Inhibitors Is Effective against Recombinant Genotype 1a, 2a, and 3a Viruses" Antimicrobial Agents and Chemotherapy, Mar. 2013, pp. 1291-1303, vol. 57, No. 3.
Kolykhalov, Alexander A. et al., "Transmission of Hepatitis C by Intrahepatic Inoculation with Transcribed RNA" Science, Jul. 1997, pp. 570-574, vol. 277.
Kuiken, Carla et al., "A Comprehensive System for Consistent Numbering of HCV Sequences, Proteins and Epitopes" Hepatology, Nov. 2006, pp. 1355-1361, vol. 44, No. 5.
Li, Yi-Ping et al., "Protease inhibitors differentially inhibit novel HCV 5'UTR-NS5A genotype 3-6 recombinants" Article intended for submission to Gastroenterology.
Li, Yi-Ping et al., "MicroRNA-122 antagonism against hepatitis C virus genotypes 1-6 and reduced efficacy by host RNA insertion or mutations in the HCV 5' UTR" PNAS, Mar. 2011, pp. 4991-4996, vol. 108, No. 12.
Li, Yi-Ping et al., "Non-genotype-specific role of the hepatitis C virus 5' untranslated region in virus production and in inhibition by interferon" Virology, 2011, pp. 222-234, vol. 421.
Li, Yi-Ping et al., "Robust full-length hepatitis C virus genotype 2a and 2b infectious cultures using mutations identified by a systematic approach applicable to patient strains" PNAS, Mar. 2012, pp. E1101-E1110.
Li, Yi-Ping et al., "Highly efficient full-length hepatitis C virus genotype 1 (strain TN) infectious culture system" PNAS, Nov. 2012, pp. 19757-19762, vol. 109, No. 48.
Li, Yi-Ping et al., "Differential Sensitivity of 5'UTR-NS5A Recombinants of Hepatitis C Virus Genotypes 1-6 to Protease and NS5A Inhibitors" Gastroenterology, 2014, pp. 812-821.e4, vol. 146.
Li, Yi-Ping et al., "Efficient infectious cell culture systems of the hepatitis C virus prototype strains HCV- 1 and H77" JVI-02877-14R1, Oct. 2014.
Lindenbach, Brett D. et al., "Complete Replication of Hepatitis C Virus in Cell Culture" Science, Jul. 2005, pp. 623-626; vol. 309.
Murayama, Asako et al., "The NS3 Helicase and NS5B-to-3 X Regions Are Important for Efficient Hepatitis C Virus Strain JFH-1 Replication in Huh? Cells" Journal of Virology, Aug. 2007, pp. 8030-8040, vol. 81, No. 15.
Murayama, Asako et al., "RNA Polymerase Activity and Specific RNA Structure Are Required for Efficient HCV Replication in Cultured Cells" PLoS Pathogens, Apr. 2010, pp. 1-11, vol. 6, Issue 4, e1000885.
Okamoto, Hiroaki et al., "Nucleotide sequence of the genomic RNA of hepatitis C virus isolated from a human carrier: comparison with reported isolates for conserved and divergent regions" Journal of General Virology, 1991, pp. 2697-2704, vol. 71.
Okamoto, Hiroaki et al., "Full-Length Sequence of a Hepatitis C Virus Genome Having Poor Homology to Reported Isolates: Comparative Study of Four Distinct Genotypes" Virology, 1992, pp. 331-341, vol. 188.
Ramirez, Santseharay et al., "Highly Efficient Infectious Cell Culture of Three HCV Genotype 2b Strains and Sensitivity to Lead Protease, NS5A, and Polymerase Inhibitors" submitted to Hepatology on Jun. 12, 2013.
Ramirez, Santseharay et al., "Highly Efficient Infectious Cell Culture of Three Hepatitis C Virus Genotype 2b Strains and Sensitivity to Lead Protease, Nonstructural Protein 5A, and Polymerase Inhibitors" Hepatology, Feb. 2014, pp. 395-407, vol. 59, No. 2.
Scheel, Troels K.H. et al., "Recombinant HCV Variants With NS5A From Genotypes 1-7 Have Different Sensitivities to an NS5A Inhibitor but Not Interferon-α" Gastroenterology, 2011, pp. 1032-1042, vol. 140.
Shiokawa, Mai et al., "Novel Permissive Cell Lines for Complete Propagation of Hepatitis C Virus" Journal of Virology, May 2014, pp. 5578-5594, vol. 88, No. 10.
Wakita, Takaji et al., "Production of infectious hepatitis C virus in tissue culture from a cloned viral genome" Nat Med., Jul. 2005, pp. 791-796, vol. 11, No. 7.
Yanagi, Masayuki et al., "Hepatitis C Virus: An Infectious Molecular Clone of a Second Major Genotype (2a) and Lack of Viability of Intertypic 1a and 2a Chimeras" Virology, 1999, pp. 250-263, vol. 262.
Database UniParc, Nov. 28, 2012, XP-002699169.

\* cited by examiner

| Isolate (genotype)[a] | Peak HCV infectivity titer[b] log₁₀ FFU/mL | | Peak HCV RNA titer[c] log₁₀ IU/mL | | Peak HCV Core titer[d] log₁₀ amol Core/mL | | Specific infectivity[e] FFU/IU | | Specific infectivity[f] FFU/amol Core | |
|---|---|---|---|---|---|---|---|---|---|---|
| | sf-HCVcc | HCVcc | sf-HCVcc | HCVcc | sf-HCVcc | HCVcc | sf-HCVcc | HCVcc | sf-HCVcc | HCVcc |
| H77(1a) | 5.0 | 4.3 | 7.6 | 7.5 | 5.7 | 5.4 | 1/398 | 1/1,585 | 1/4.8 | 1/13.5 |
| J4(1b) | 4.7 | 3.2 | 7.5 | 7.3 | 5.6 | 5.1 | 1/631 | 1/12,589 | 1/8.1 | 1/79.8 |
| J6(2a) | 5.6 | 5.0 | 7.6 | 7.6 | 5.5 | 5.5 | 1/100 | 1/398 | 1/0.8 | 1/3.4 |
| S52(3a) | 4.9 | 4.3 | 7.4 | 7.2 | 5.5 | 5.4 | 1/316 | 1/794 | 1/3.8 | 1/12.5 |
| ED43(4a) | 4.7 | 3.6 | 7.1 | 7.6 | 5.0 | 5.4 | 1/251 | 1/10,000 | 1/2.0 | 1/58.0 |
| SA13(5a) | 6.2 | 4.1[g] | 7.8 | 7.0 | 5.5 | 4.9 | 1/40 | 1/794 | 1/0.2 | 1/6.6 |
| HK6a(6a) | 5.6 | 4.0 | 7.7 | 7.0 | 5.6 | 4.8 | 1/126 | 1/1,000 | 1/0.9 | 1/5.9 |

Fig. 14

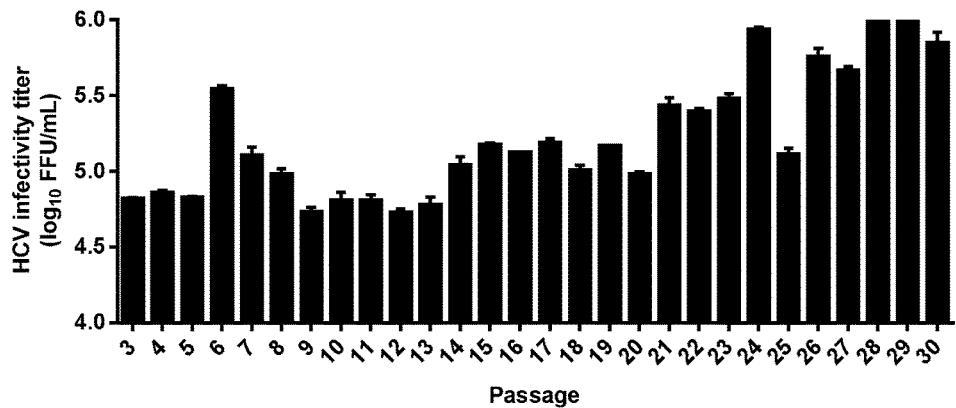
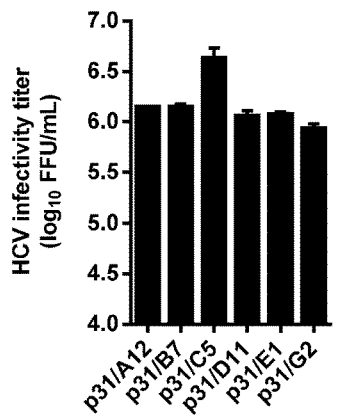
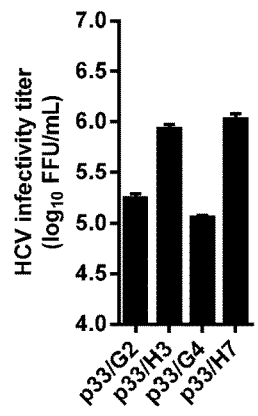
Fig. 16

Fig. 17

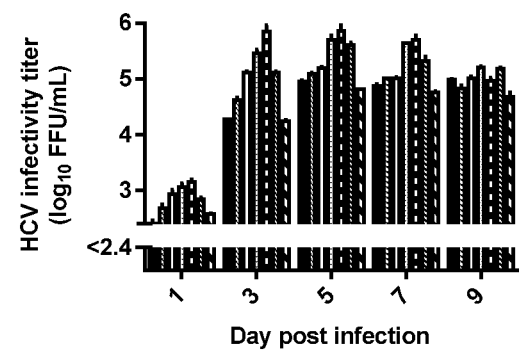
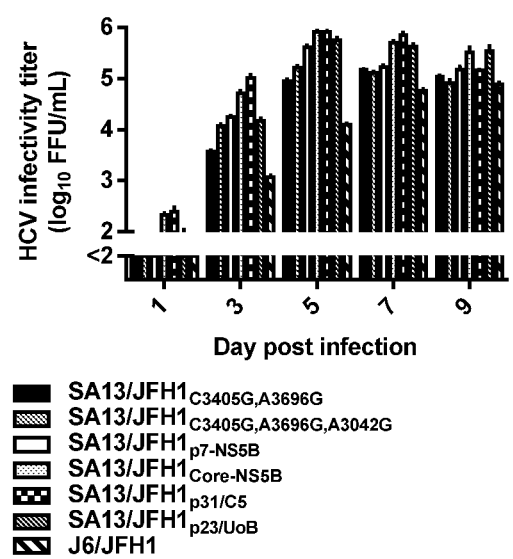
Fig. 19

| Virus stock | MOI 0.003 | | MOI 0.0003 | |
|---|---|---|---|---|
| | Peak day post infection[d] | Peak infectivity titer[e] | Peak day post infection[d] | Peak infectivity titer[e] |
| SA13/JFH1 C3405G,A3696G[a] | 9

Purification and concentration

START: 5.8 L culture supernatant with 9.1 log FFU

| Procedure | Recovery per step (%) |
|---|---|
| Cross-flow filtration (21 mL) | 43 |
| 3-cushion Ultracentrifugation (7.5 mL) | 69 |
| Ultracentrifugation pelleting (0.6 ml) | 24 |
| Iodixanol Gradient Ultracentrifugation (1.7 mL) | 100 |
| Sephadex Chromatography | 98 |

END: 4.5 mL vaccine stock with 8.0 log FFU

Result:
- >99% purification
- 1290-fold concentration
- Total recovery 8%

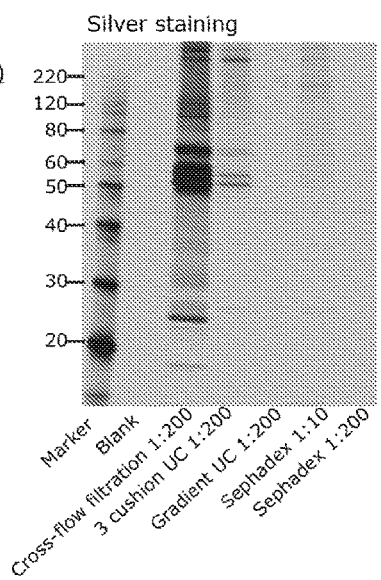

Fig. 24

Fig. 27

DEVELOPMENT OF METHODS FOR PRODUCTION OF A WHOLE VIRUS VACCINE CANDIDATE STOCK AND NOVEL ADAPTIVE MUTATIONS IN HEPATITIS C VIRUS

CROSS REFERENCE TO RELATED APPLICATIONS

This application is a U.S. National Phase Application of PCT International Application Number PCT/DK2015/050097, filed on Apr. 16, 2015, designating the United States of America and published in the English language, which is an International Application of and claims the benefit of priority to Danish Patent Application No. PA 2014 70221, filed on Apr. 16, 2014. The disclosures of the above-referenced applications are hereby expressly incorporated by reference in their entireties.

FIELD OF THE INVENTION

The present invention relates to methods for obtaining a whole virus vaccine candidate stock. The present invention also relates to an inactivated whole virus vaccine candidate stock that can be used for vaccination purposes as well as development of novel high titer virus based on specific adaptive mutations.

BACKGROUND OF THE INVENTION

Hepatitis C virus (HCV) is a major public healthcare burden with 3-4 million new infections occurring each year and more than 150 million individuals estimated to be chronically infected worldwide. Many of these individuals develop serious chronic liver diseases such as cirrhosis and hepatocellular carcinoma, making HCV the most frequent cause of liver transplantation.

HCV is an enveloped, positive-stranded RNA virus of the genus Hepacivirus within the Flaviviridae family. Due to a high degree of genetic heterogeneity, HCV has been classified in 6 epidemiologically important genotypes and numerous subtypes, differing in approximately 30% and 20% of their nucleotide and amino acid sequence, respectively.

Genotypes show important clinical and biological differences. Serotypes have not been defined; however, different genotypes and subtypes show differential sensitivity to neutralizing antibodies found in sera of chronically infected patients and to monoclonal neutralizing antibodies with therapeutic potential.

The 9.6 kb HCV genome consists of 5' and 3' untranslated regions and a single open reading frame encoding structural proteins (Core, E1 and E2), the viroporin p7, and nonstructural proteins (NS2, NS3, NS4A, NS4B, NS5A and NS5B). The HCV virion is believed to consist of a nucleocapsid of HCV Core proteins containing the genomic RNA, covered by a lipid envelope with the HCV envelope glycoproteins E1 and E2. The HCV life cycle is tightly linked to the hepatic lipid metabolism.

During assembly and release, the HCV virion is believed to associate with very-low-density-lipoprotein (VLDL) or VLDL-like structures, creating lipo-viro-particles (LVP). Thus, HCV apparently circulates in infected patients associated to different classes of lipoproteins, resulting in a heterogeneous density profile apparent following buoyant density gradient ultracentrifugation. Components of the VLDL assembly and secretion pathway, such as apolipoprotein E (ApoE), might be important for the association between HCV and lipoproteins.

HCV entry is mediated by several co-receptors, including CD81, the low-density-lipoprotein receptor (LDLr) and the scavenger receptor class B type I (SR-BI). While HCV is believed to interact directly with CD81 through E2, interactions with other receptors, such as LDLr and SR-BI, might occur through lipoprotein components present on the LVP, such as ApoE, although direct interactions between E2 and SR-BI have also been reported. Eventually, HCV is internalized through clathrin-mediated endocytosis.

There is no vaccine available for HCV. Current standard-of-care, based on pegylated interferon-α2 and ribavirin, has limited efficacy and is associated with severe side effects and contraindications. Even though promising new compounds for treatment of HCV are being developed and licenced, only a minority of HCV-infected individuals is expected to be diagnosed and treated, mainly due to the asymptomatic nature of infection, economic constraints and contraindications.

Thus, an HCV vaccine is needed to control HCV globally. Most successful antiviral vaccines employ inactivated or attenuated whole viral particles as vaccine antigen and depend on the induction of neutralizing antibodies. Due to a lack of HCV particle-producing cell culture systems, this approach was not feasible for HCV.

Only in 2005, the first HCV cell culture system supporting the full viral life cycle was developed, based on the genotype 2a isolate JFH1 and the human hepatoma cell line Huh7 and derived cell lines.

Subsequently, culture systems producing HCV particles (HCVcc) of the major genotypes were developed using JFH1-based recombinants expressing genotype specific Core, E1, E2, p7 and NS2. Such particles could serve as antigens in a whole-virus inactivated HCV vaccine primarily aiming at induction of neutralizing antibodies against structural proteins of the major HCV genotypes.

However, HCVcc yields from the developed cell culture systems are relatively low compared to quantities envisioned to be required for vaccine production. Further, as patient derived HCV particles, HCVcc showed a heterogeneous density profile, making density-based purification and concentration procedures difficult. Also, cell cultures are typically treated with animal-derived trypsin, and growth medium used for production of HCVcc is typically supplemented with fetal bovine serum (FBS).

Vaccine development, as well as other research applications, such as biophysical studies of HCV particle composition, require generation of purified and concentrated HCVcc stocks.

This is expected to be facilitated by reducing concentrations of non-HCV proteins such as FBS derived proteins in HCVcc producing cell cultures. Further, use of FBS and animal-derived trypsin increases the risk of contamination with adventitious microbial agents, of relevance for HCV vaccine development. Thus, development of methods for production of HCVcc under serum-free conditions is a research focus.

At the onset of this study it had been demonstrated that Huh7 cells could be cultured in serum-free medium (RPMI 1640 supplemented with Na2SeO3) without previous adaptation for an extended period of time, and that serum-free cell cultures (DMEM supplemented with Na2SeO3 and lipid rich albumin) allowed replication of HCV.

However, establishment of a robust methodology for generation of high-titer single-density serum-free HCVcc is not known and is expected to aid HCV vaccine development.

This is relevant for HCV as well as other viruses similar to HCV.

It is also very important to generate new HCV recombinants that can grow at titers that are high enough to allow application for vaccine development.

Such viruses can be purified, up-concentrated and inactivated through specific procedures. These procedures are required to develop a whole virus inactivated vaccine antigen from crude cell culture supernatant.

These procedures have not been established for HCV even though the initial HCV cell culture was developed in 2005.

SUMMARY OF THE INVENTION

The present inventors have now surprisingly found that specific high-titer viruses grown in serum-free medium can be purified, up-concentrated and inactivated to generate a whole virus inactivated vaccine stock that can be used as antigen for immunization studies.

These stocks will be key in facilitating virological studies, and for vaccine development.

Thus, it is an object of the present invention to provide such stocks.

One aspect of the present invention relates to a method of obtaining a whole virus vaccine candidate stock, the method comprising the steps of providing a cell culture supernatant comprising virus particles, purification and/or up-concentration of the cell culture supernatant, optionally a second or subsequent rounds of step purification and/or up-concentration of the cell culture supernatant, optionally collection of one or more specific fractions obtained from the purification and/or up-concentration, and obtaining the whole virus vaccine candidate stock.

In one embodiment of the present invention is the cell culture grown in a serum free medium.

In another embodiment of the present invention is the medium adenovirus expression medium optionally supplemented with penicillin 100 U/mL and streptomycin 100 μg/mL.

In a further embodiment of the present invention is the cell culture grown under optimized conditions such as but not limited to cell factories or in bioreactors, on optimized surfaces, in suspension or on beads.

In yet another embodiment of the present invention are the cells in the cell culture Huh7.5 cells.

In another embodiment of the present invention is the virus non-enveloped or enveloped.

In another embodiment of the present invention the virus belongs to the Flaviviridae family.

In a further embodiment of the present invention is the virus a virus selected from the group consisting of a flavivirus, a hepacivirus, a pegivirus, and a pestivirus.

In yet another embodiment of the present invention is the virus a virus selected from the group consisting of yellow fever virus, west nile virus, dengue fever virus, GB virus B, GB virus A, GB virus C, GB virus D, bovine viral diarrhea virus, classical swine fever, hog cholera, HAV, HBV, HCV, HCVcc, sf-HCVcc and specific genotypes of HCV selected from genotypes 1-7.

In a further embodiment of the present invention is the purification and/or up-concentration performed using a method selected from the list consisting of centrifugation, ultracentrifugation, density gradient ultracentrifugation, iodixanol cushion centrifugation, sucrose cushion centrifugation, nycodenz cushion centrifugation, iodixanol gradient centrifugation, sucrose gradient centrifugation, nycodenz gradiend centrifugation, cesium chloride gradient centrifugation, ultracentrifugation pelleting, filtration, clarification, microfiltration, direct filtration, cross-flow filtration, ultrafiltration, precipitation, polyethylene glycol precipitation, polymer precipitation, polyelectrolyte precipitation, chromatography, and dialysis.

In a further embodiment of the present invention there are 1, 2, 3, 4, 5, 6, or 7 iodixanol or sucrose cushions.

In another embodiment of the present invention is the filtration selected from the list consisting of conventional direct or dead end filtration, depth filtration, cut-off filtration, small-scale cross-flow filtration, and cross-flow filtration.

In another embodiment of the present invention is the cross-flow filtration selected from the group of hollow-fiber filters such as but not limited to MicroKros® Filter Modules, MidiKros® Filter Modules, MidiKros® TC Filter Modules, MiniKros® Sampler Filter Modules, MiniKros® Filter Modules, KrosFlo® Filter Modules, KrosFlo® Max Filter Modules and Vivaflow. Different molecular weight cut-offs such as 500 kDa, 300 kDA, 200 kDa, 100 kDa, 70 kDa, 50 kDa, 30 kDa, 10 kDa, 5 kDa, 3 kDa, 1 kDa might be used. Filters with different surface areas might be used.

In another embodiment of the present invention is the precipitation PEG precipitation.

In another embodiment of the present invention is the ultracentrifugation selected from the group consisting of iodixanol gradient ultracentrifugation, sucrose gradient ultracentrifugation, ultracentrifugation pelleting.

In another embodiment of the present invention is the chromatography selected from the group consisting of affinity or sephadex chromatography.

A further embodiment of the present invention relates to the method of the present invention wherein the steps are providing a cell culture supernatant comprising virus particles, purification and/or up-concentration of the cell culture supernatant using cross-flow filtration, purification and/or up-concentration of the cell culture supernatant using 3-cushion ultracentrifugation, collection of 3 fractions and use the middle one, purification and/or up-concentration of the cell culture supernatant using ultracentrifugation pelleting, purification and/or up-concentration of the cell culture supernatant using iodixanol gradient ultracentrifugation, collection of 18 fractions and use the 3 containing most HCV, purification and/or up-concentration of the cell culture supernatant using sephadex chromatography, and obtaining the whole virus vaccine candidate stock.

The fractions collected can be 2-35 fractions, such as 3-8, such as 10-35, such as 2-7, such as 5-20, such as 3, such as, 4, such as 5, such as 8, such as 10, such as 12, such as 20.

Another embodiment of the present invention relates to the method of the present invention wherein the steps are providing a cell culture supernatant comprising virus particles, purification and/or up-concentration of the cell culture supernatant using cross-flow filtration, purification and/or up-concentration of the cell culture supernatant using 3-cushion ultracentrifugation, collection of 3 fractions and use the middle one, purification and/or up-concentration of the cell culture supernatant using small-scale cross-flow filtration, purification and/or up-concentration of the cell culture supernatant using iodixanol gradient ultracentrifugation, collection of 18 fractions and use the 3 containing most HCV, purification and/or up-concentration of the cell culture supernatant using sephadex chromatography, and obtaining the whole virus vaccine candidate stock.

Another embodiment of the present invention relates to the whole virus vaccine candidate stock obtained from the methods of the present invention.

Another aspect of the present invention relates to a method of obtaining a whole virus vaccine inactivated candidate stock, the method comprising the step of inactivation of the whole virus vaccine candidate stock according to the present invention to obtain a whole virus vaccine inactivated candidate stock.

In another embodiment of the present invention is the inactivation performed using UV radiation, UV combined with photosensitizer, or paraformaldehyde, or betapropiolactone, or gamma-irradiation.

Another embodiment of the present invention relates to the whole virus vaccine inactivated candidate stock obtained from the methods of the present invention.

Another aspect of the present invention relates to a pharmaceutical composition comprising the whole virus vaccine inactivated candidate stock of the present invention formulated with one or more adjuvant(s), excipients and/or carriers.

A further aspect of the present invention relates to isolated nucleic acid molecule which encodes a human hepatitis C virus, comprising at least one amino acid mutation selected from the group consisting of R104Q, R114W, I178V, V187A, V235L, T385P, H777Y, L782V, I850L, V866A, Y900C, A1021G, K1118R, A1406G, V1635I, V1692A, A1862V, A1900G, P1908L, T1936A, N2034D, T2055I, D2225G, E2238G, S2248P, V2252A, L2266P, M2275T, I2340T, S2357L, C2419S, A2500S, N2537T, C2723S, V2841A, and L2993H according to the H77 reference sequence with GenBank accession number AF009606.

Another aspect of the present invention relates to a composition comprising a nucleic acid molecule according to the present invention suspended in a suitable amount of a pharmaceutical acceptable diluent or excipient.

Another aspect of the present invention relates to a cassette vector for cloning viral genomes, comprising, inserted therein, the nucleic acid sequence according to the present invention and having an active promoter upstream thereof.

Another aspect of the present invention relates to a cell comprising the nucleic acid, the composition, or the cassette vector of the present invention.

Another aspect of the present invention relates to method for producing a hepatitis C virus particle, comprising culturing a cell according to the present invention to allow the cell to produce the virus.

Another aspect of the present invention relates to hepatitis C virus particle obtainable from this method and a hepatitis C vaccine comprising this hepatitis C virus particle.

Additional aspects of the present invention relates to methods for producing a hepatitis C virus vaccine, and antibody against the hepatitis C virus particle, a method for producing a cell, which replicates human hepatitis C virus and produces a virus particle, a cell obtainable by such a method, a method for producing a hepatitis C virus particle, a method for in vitro producing a hepatitis C virus-infected cell comprising culturing a cell according to the invention infecting other cells with the produced virus particle in the culture, and a method for screening an anti-hepatitis C virus substance.

BRIEF DESCRIPTION OF THE FIGURES

FIG. 1: Serum-free Huh7.5 cell cultures produced high-titer sf-HCVcc. Huh7.5 cells were infected with (A) H77 (1a), (B) J4(1b), (C) S52(3a) and (D) ED43(4a) JFH1-based Core-NS2 recombinants in DMEM+10% FBS for 18 hours. Cells were split into two replicate DMEM+10% FBS cultures. When ~80% of culture cells were infected, as determined by HCV NS5A immunostaining, one replicate culture was maintained in DMEM+10% FBS (black bars), while the other replicate culture was maintained in AEM (grey bars). At the indicated day post infection, supernatants were collected and DMEM+10% FBS cultures were split, while fresh medium was added to AEM cultures as described in Materials and Methods. Supernatant HCVcc infectivity titers are shown as means of 3 replicates with standard error of the mean (SEM). The lower limit of detection in the experiments shown was up to 2.7 log 10 FFU/ml, indicated by y-axis break. *, at this time point, the experiment consisted only of replicate cultures maintained in DMEM+10% FBS; only one culture was titrated.

FIG. 2: Generation of genotype 1-6 sf-HCVcc virus stocks. Huh7.5 cells were infected with the indicated viruses in DMEM+10% FBS at an MOI of 0.003 for 6 hours. On day 6 to 15 post infection, depending on the growth kinetics of the respective virus, when 40-80% of culture cells were infected, as determined by HCV NS5A immunostaining, DMEM+10% FBS was replaced by AEM. At the indicated day post infection, supernatant was collected and fresh AEM was added to the cells. Supernatant HCVcc infectivity titers are shown as means of 3 replicates with standard error of the mean (SEM). Black bars represent DMEM+10% FBS supernatant HCVcc infectivity titers; grey bars represent AEM supernatant sf-HCVcc infectivity titers. The lower limit of detection in the experiments shown was up to 2.3 log 10 FFU/ml, indicated by y-axis break.

FIG. 3: Increased infectivity titers of serum-free cell cultures were not due to reduced cell-splitting, changes in cell viability or proliferation, or increased viral stability. (A) AEM cultures produced higher infectivity titers than DMEM+10% FBS cultures handled similarly and DMEM+10% FBS control cultures. Huh7.5 cells were infected with the SA13(5a) JFH1-based Core-NS2 recombinant in DMEM+10% FBS for 3 hours at an MOI of 0.003. On day 4 post-infection, cells were split into three replicate cultures. Following day 6 post infection, when ~80% of culture cells were infected, as determined by HCV NS5A immunostaining, one replicate culture was maintained in DMEM+10% FBS and split every 2-3 days, another replicate culture was maintained in DMEM+10% FBS without being split, while the third replicate culture was maintained in AEM without being split. At the indicated days post infection, supernatants were collected. Supernatant HCVcc infectivity titers are shown as means of 3 replicates with standard error of the mean (SEM). The lower limit of detection in the experiment shown was up to 2.6 log 10 FFU/ml, indicated by y-axis break. * The culture originally infected with SA13(5a) was first split into three replicates at day 4 post infection; thus, on day 1 and 4 post infection only one infectivity titer is shown. On day 6, DMEM+10% FBS supernatants were harvested from the three replicate cultures; subsequently cultures were maintained in the different growth media indicated. (B) AEM cultures showed similar viability and proliferation as DMEM+10% FBS cultures. Cell viability or proliferation of Huh7.5 cells cultured for 48 hours in AEM versus DMEM+10% FBS was determined as described in Materials and Methods. The % viability/proliferation was calculated by relating absorbance at 490 nm (viability) or 450 nm (proliferation) determined for AEM cultures to the mean absorbance of 10 replicate DMEM+10% FBS cultures. Bars represent the means of 10 replicates with SEM.

(C) sf-HCVcc and HCVcc showed similar freeze-thaw stability. SA13(5a) diluted 1:100 in DMEM+10% FBS or sf-SA13(5a) diluted 1:100 in either AEM or AEM+10% FBS were exposed to up to 5 freeze/thaw cycles. Samples were thawn at room temperature and frozen at −80° C. After the indicated number of cycles, infectivity titers were determined as described in Materials and Methods. The % infectivity was calculated by relating the infectivity titer of each sample to the mean titer of a reference sample of the same stock, which had been stored at −80° C. Bars represent the means of three replicates with SEM. (D) sf-HCVcc showed decreased stability under temperature stress. SA13 (5a) diluted 1:100 in DMEM+10% FBS or sf-SA13(5a) diluted 1:100 in either AEM or AEM+10% FBS were incubated at 4° C., room temperature (RT) or 37° C. for 4 to 48 hours as indicated. Infectivity titers were determined as described in Materials and Methods. The % infectivity was calculated by relating the infectivity titer of each sample to the mean titer of a reference sample of the same stock, which had been stored at −80° C. Bars represent the means of three replicates with SEM. The lower limit of detection in the experiment shown was up to 2%, indicated by y-axis break.

Figure 4:
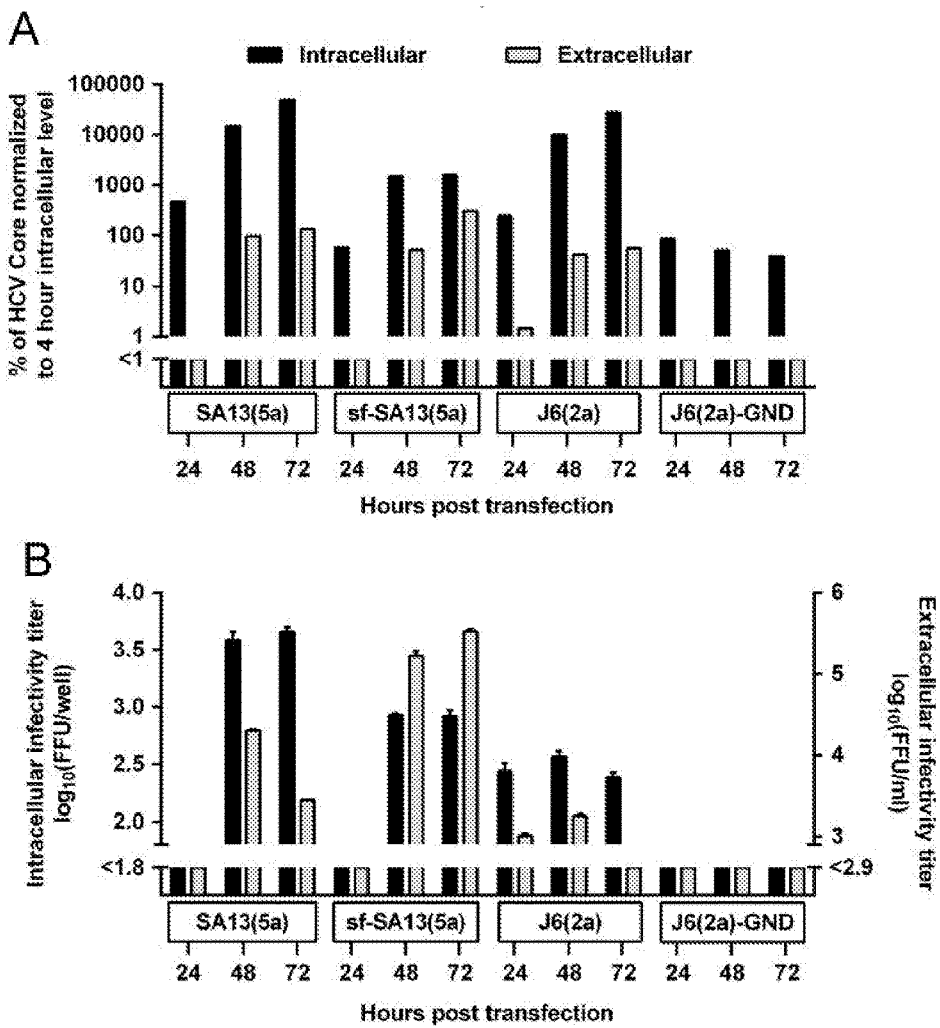

FIG. 4: Serum-free culture decreased viral replication/translation but enhanced viral release and specific infectivity. S29 cells were transfected with SA13(5a) as well as positive control (J6(2a)) and negative control (J6(2a)-GND) HCV RNA transcripts as described in Materials and Methods. (A) Intracellular (black bars) and extracellular (grey bars) Core levels were determined 24, 48 and 72 hours post transfection. Core levels were normalized to intracellular Core levels measured 4 hours post transfection. (B) Intracellular (black bars) and extracellular (grey bars) infectivity titers were determined 24, 48 and 72 hours post transfection. Intracellular infectivity titers are shown as the means (FFU/well) of three replicates with SEM. Extracellular infectivity titers are shown as the means (FFU/mL) of three replicates with SEM. The lower limits of detection are indicated by y-axis breaks.

Figure 5:
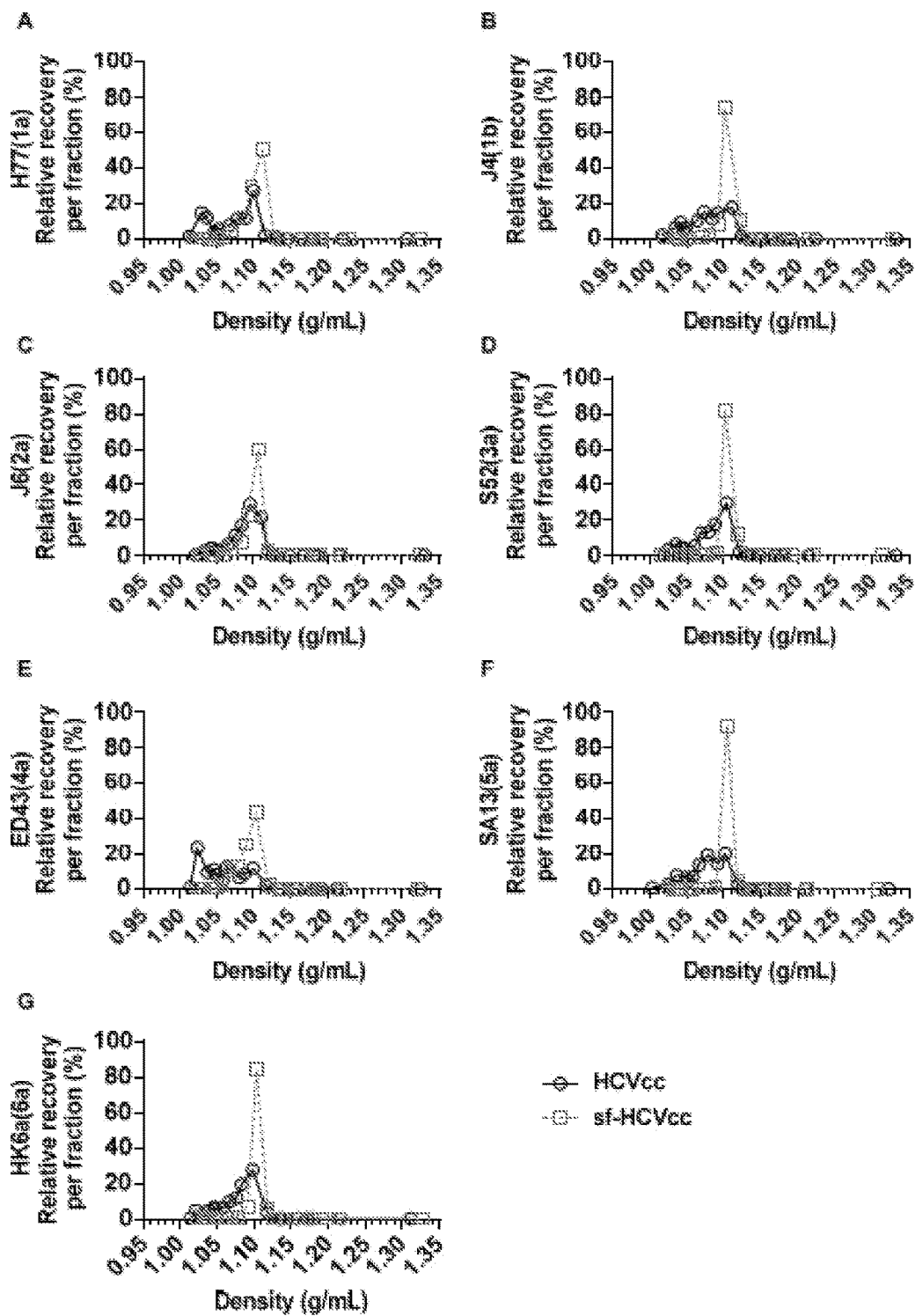

FIG. 5: The sf-HCVcc particles of genotype 1-6 displayed an altered density profile with a single infectivity peak. Of the virus stocks described in FIG. 2, 10 mL HCVcc supernatant taken from the last harvest of DMEM+10% FBS culture supernatant (black line) or 10 mL sf-HCVcc supernatant taken after 48 hours of AEM culture (grey, dotted line) was concentrated and layered on top of a pre-formed 10-40% iodixanol gradient and subjected to ultracentrifugation as described in Materials and Methods. Fractions were collected from the bottom of the gradients and analyzed by infectivity titration and by density determination as described in Materials and Methods. The HCV Core-E2 sequences of all virus stocks used were determined by direct sequencing. Compared to the plasmid sequence, sf-H77(1a) and H77(1a) had acquired the previously described amino acid change Y361H [11], estimated to be present in 50% of viral genomes. The sf-J4(1b) had acquired amino acid changes T578A and D584G, estimated to be present in the majority of viral genomes. Relative recovery per fraction (%) was calculated by relating the amount of infectious virus detected in each fraction to the total amount of infectious virus collected, and is plotted against the density determined for each fraction.

Figure 6:
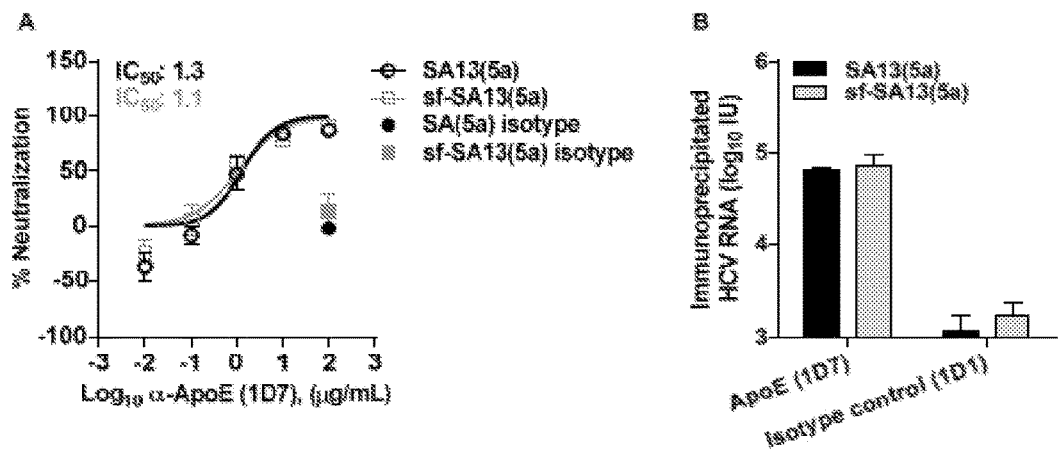

FIG. 6: HCVcc and sf-HCVcc showed similar association with ApoE. (A) Monoclonal α-ApoE antibody (1D7) and control mouse IgG1κ (1D1) were diluted in DMEM+10% FBS to the indicated concentrations. SA13(5a) (black circles) and sf-SA13(5a) (grey squares) were diluted in DMEM+10% FBS and incubated with dilutions of α-ApoE or mouse IgG1K for 30 minutes at 37° C. The virus-antibody mixes were added to Huh7.5 cells, plated the previous day in poly-D-lysine coated 96 well plates. After 3 hours of incubation, virus-antibody mixes were removed and DMEM+10% FBS was added. Cells were fixed 48 hours post infection and stained, and the number of single HCV NS5A positive cells per well was determined by automated counting as described in Materials and Methods. The % neutralization was calculated by relating counts of experimental wells to the mean count of six replicate wells with untreated control virus. Data points are means of three replicates with SEM (error bars). Following logarithmic transformation of X-values, variable-slope sigmoidal dose-response curves were fitted [Y=Bottom+(Top−Bottom)/(1+$10^{(Log10EC50-X) \times HillSlope}$)]. "Bottom" was constrained to "0"; "Top" was constrained to "100". (B) Immunoprecipitation was carried out on $10^6$ IU HCV RNA of SA13(5a) and sf-SA13(5a), using monoclonal α-ApoE (1D7) and control mouse IgG1κ (1D1) as described in Materials and Methods. Amounts of HCV RNA (IU) were determined in the immunoprecipitated fractions using TaqMan PCR as described in Materials and Methods. RNA titers are shown as the mean of two replicates with SEM.

Figure 7:
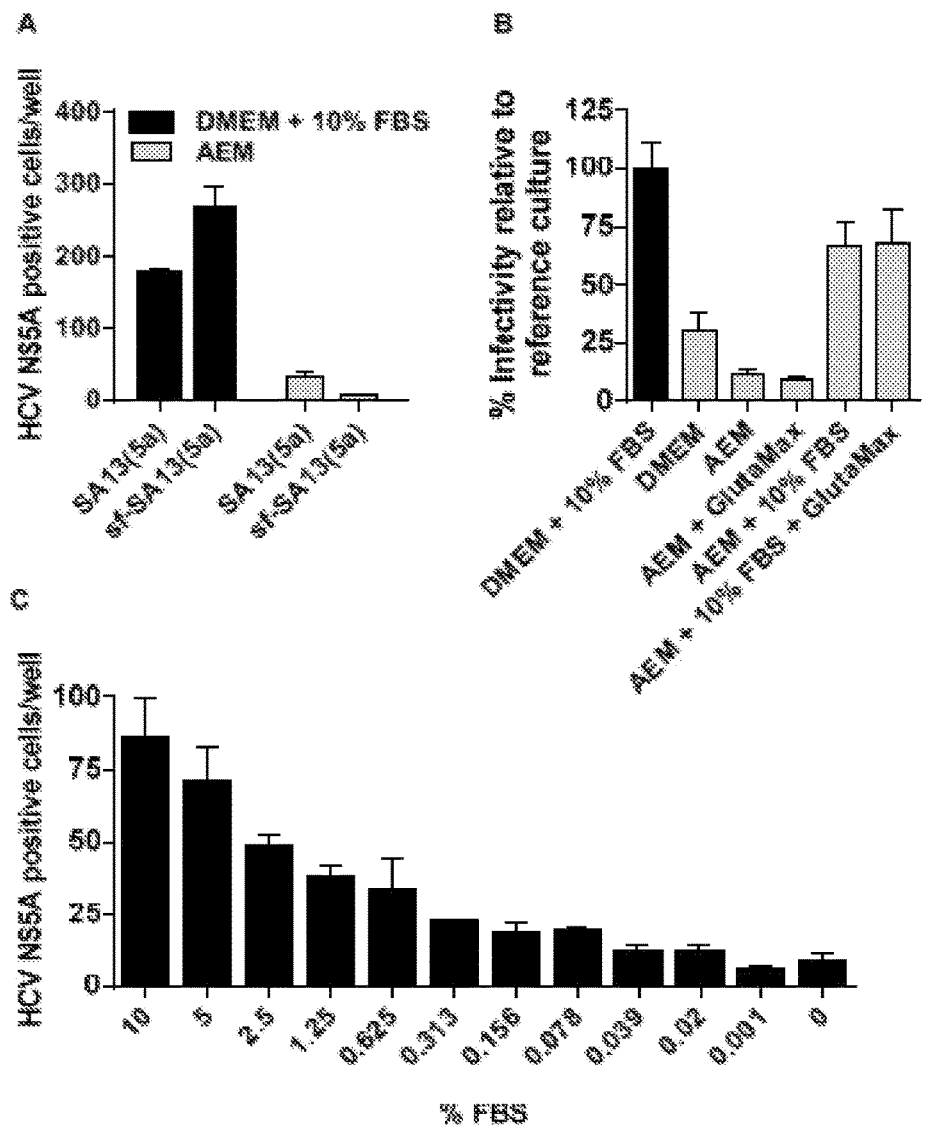

FIG. 7: FBS enhances infectivity of both HCVcc and sf-HCVcc. (A-C) Huh7.5 cells seeded in poly-D-lysine coated 96-well plates the previous day, were incubated with (A) SA13(5a) and sf-SA13(5a) diluted in DMEM+10% FBS (black bars) or AEM (grey bars), (B) sf-SA13(5a) diluted in different media with supplements as indicated or (C) sf-SA13(5a) diluted in AEM supplemented with different concentrations of FBS. % FBS in growth medium indicates the final FBS concentration. (A-C) Cells were incubated with virus mixes for 3 hours. After incubation, fresh DMEM+10% FBS was added to all wells. Cells were incubated for 48 hours before they were fixed, stained and the number of single HCV NS5A positive cells per well was determined by automated counting as described in Materials and Methods. Error bars represent SEM of triplicates. For (B), the mean infectivity (HCV NS5A positive cells/well) of triplicate wells of the reference culture (DMEM+10% FBS, black bar) was set to 100%. The number of HCV NS5A positive cells/experimental well was related to this mean to calculate % infectivity relative to the reference culture.

Figure 8:
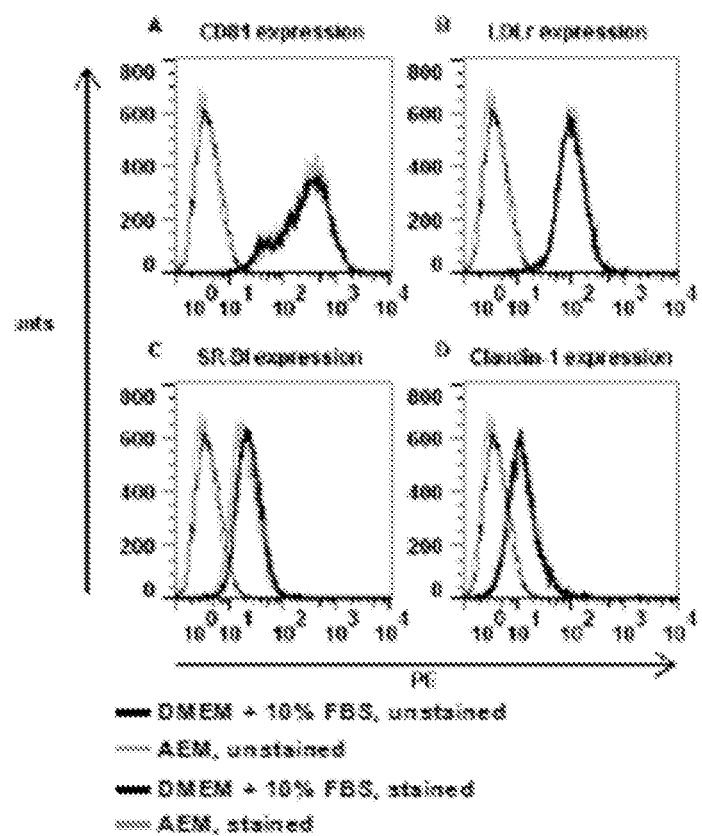

FIG. 8: Huh7.5 cells cultured in DMEM+10% FBS or AEM showed similar surface expression of HCV co-receptors. Huh7.5 cells were incubated for 3 hours in DMEM+10% FBS or AEM and subsequently prepared for flow cytometry analysis as described in Materials and Methods. Cell surface expression of HCV co-receptors was determined using antibodies against (A) CD81, (B) LDL-r, (C) SR-BI and (D) claudin-1 as described in Materials and Methods. PE signals were recorded on a BD FACSCalibur flow cytometer. Histograms show the co-receptor surface expression in cells cultured in DMEM+10% FBS (dark blue) or AEM (light blue) compared to unstained cells (black and grey, respectively).

Figure 9:
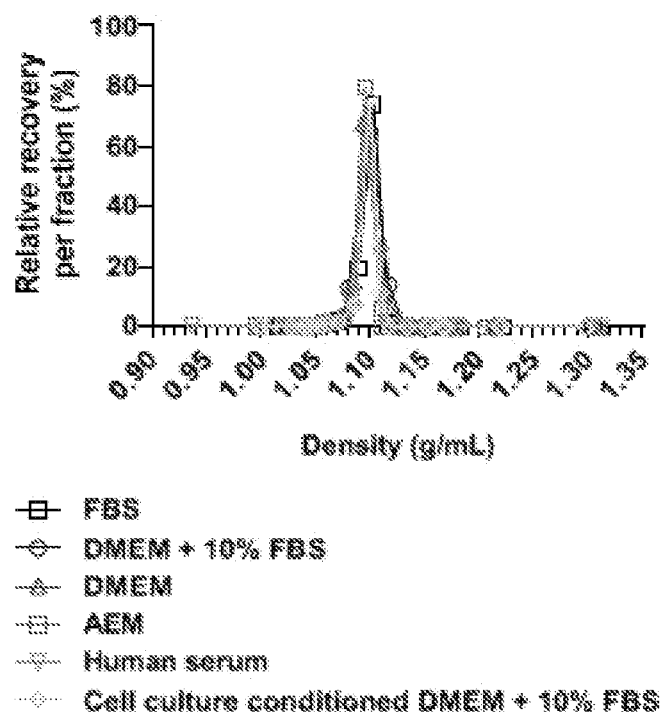

FIG. 9: The sf-HCVcc density profile was maintained after in vitro incubation with serum. The sf-SA13(5a) recombinant was mixed 1:1 with either 100% FBS, DMEM+10% FBS, DMEM, AEM, 100% human serum or sterile filtered cell culture conditioned medium (DMEM+10% FBS harvested after 48 hours culture on naïve Huh7.5 cells) and incubated for 6 hours at 37° C. Mixes were layered on top of a pre-formed 10-40% iodixanol gradient, and subjected to ultracentrifugation as described in Materials and Methods. Fractions were collected from the bottom of the gradients and analyzed by infectivity titration and by density determination as described in Materials and Methods. Relative recovery per fraction (%) was calculated by relating the amount of infectious virus detected in each fraction to the total amount of infectious virus collected, and is plotted against the density determined for each fraction.

Figure 10:
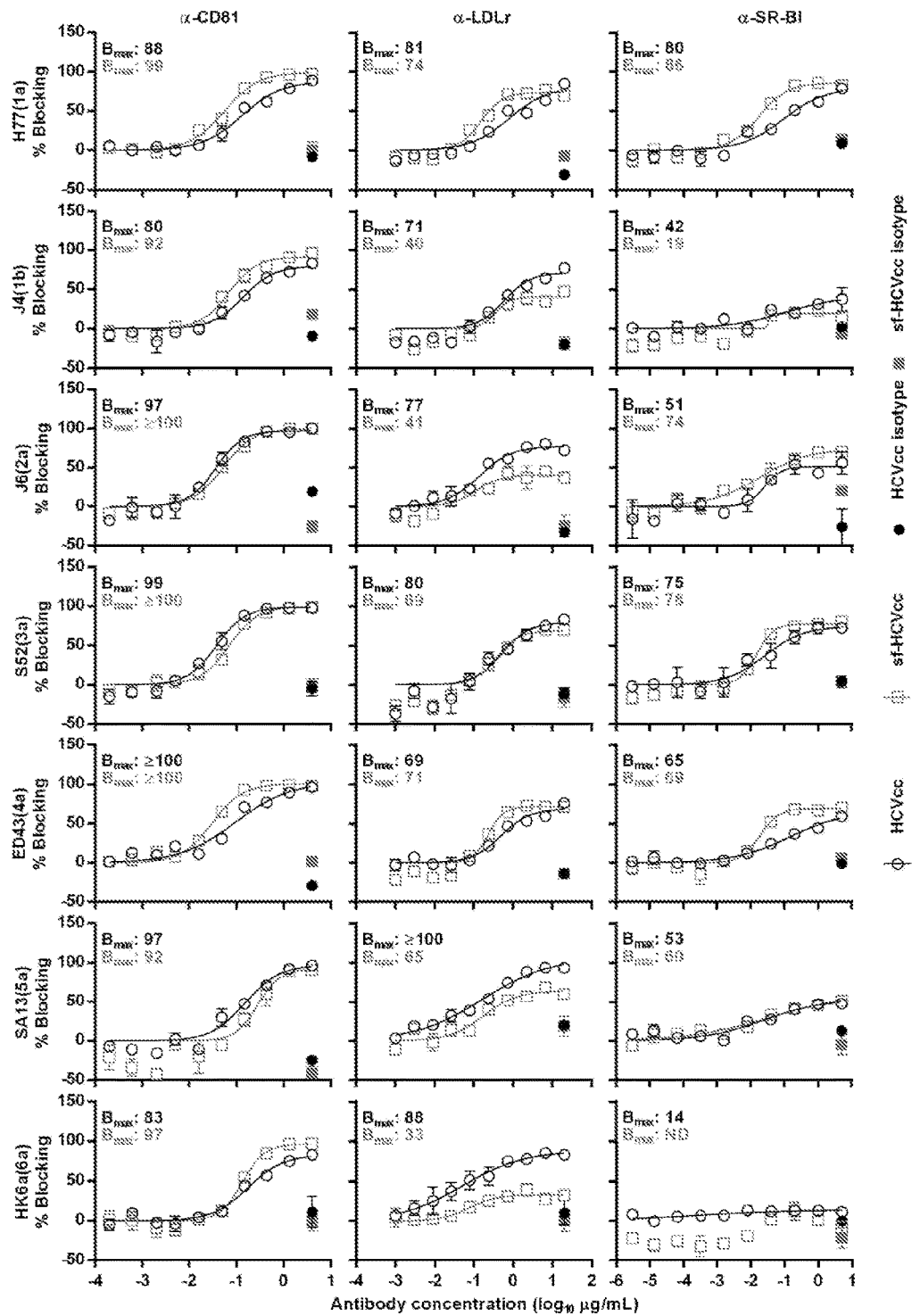

FIG. 10: Effect of co-receptor blocking on HCVcc and sf-HCVcc entry. α-CD81 (left column), α-LDLr (middle column) or α-SR-BI (right column) was diluted in DMEM+ 10% FBS to the indicated concentrations. Specified antibody (open symbols) or control antibody (closed symbols) dilutions were added to Huh7.5 cells, plated the previous day onto poly-D-lysine coated 96-well plates and incubated for 1 hour. HCVcc (black circles) were diluted in DMEM+10% FBS and sf-HCVcc (grey squares) were diluted in AEM+ 10% FBS and added to cultures. After 6 hours incubation, antibody-virus mixes were removed and DMEM+10% FBS was added. Cells were fixed 48 hours post infection and stained, and the number of single HCV NS5A positive cells per well was determined by automated counting as described in Materials and Methods. The HCV Core-E2 sequences of all virus stocks used were determined by direct sequencing. Sequences were identical for HCVcc and sf-HCVcc of the same recombinant. Compared to the plasmid sequence, H77(1a) viruses had acquired amino acid change I3485 and J4(1b) had acquired amino acid change V710L, both estimated to be present in the majority of viral genomes. The % blocking was calculated by relating counts of experimental wells to the mean count of six replicate wells with untreated control virus. Data points are means of three replicates with SEM (error bars). Following logarithmic transformation of X-values, variable-slope sigmoidal dose-response curves were fitted [Y=Bottom+(Top−Bottom)/(1+ $10^{(Log10EC50-X) \times HillSlope}$)]. "Bottom" was constrained to "0". Bmax values, the Y values at the top plateaus of the fitted curves, are shown for HCVcc (black) and sf-HCVcc (grey). No curve could be fitted to data points obtained for sf-HK6a (6a) in SR-BI blocking experiments. ND, not determinable.

Figure 11:
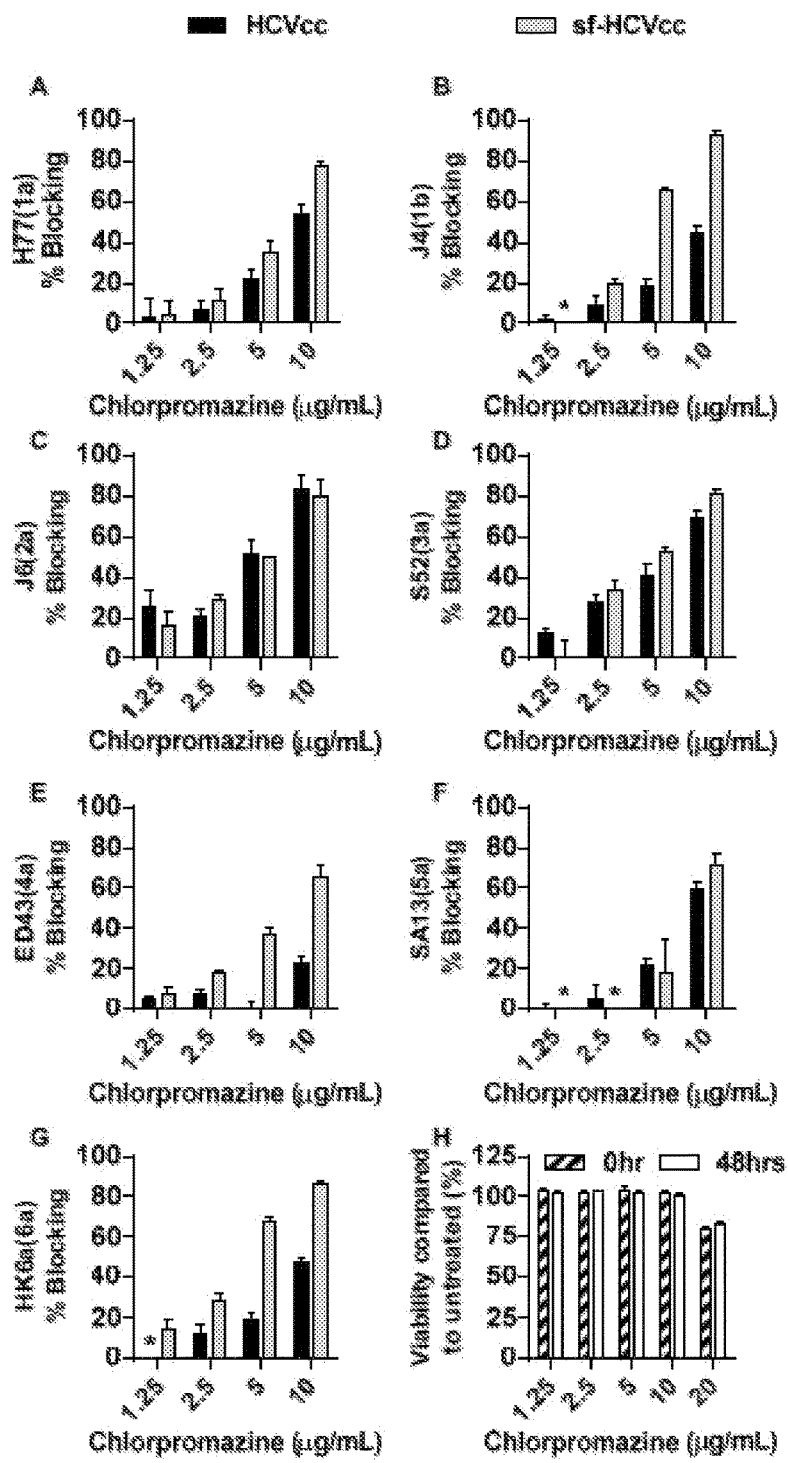

FIG. 11: Effect of chlorpromazine treatment on HCVcc and sf-HCVcc entry. (A-G) Chlorpromazine was diluted in DMEM+10% FBS to the concentrations indicated and then added to Huh7.5 cells, plated the previous day onto poly-D-lysine coated 96-well plates, and incubated for 30 minutes. HCVcc (black bars) were diluted in DMEM+10% FBS and sf-HCVcc (grey bars) were diluted in AEM+10% FBS and added to cultures. After 6 hours incubation, chlorpromazine-virus mixes were removed and DMEM+10% FBS was added. Cells were fixed 48 hours post infection and stained, and the number of single HCV NS5A positive cells per well was determined by automated counting as described in Materials and Methods. The HCV Core-E2 sequences of all virus stocks used were determined by direct sequencing. Sequences were identical for HCVcc and sf-HCVcc of the same recombinant. Compared to the plasmid sequence, H77(1a) viruses had acquired amino acid change I348S and J4(1b) had acquired amino acid change V710L, both estimated to be present in the majority of viral genomes. The % blocking was calculated by relating counts of experimental wells to the mean count of six replicate wells with untreated control virus. Data points are means of three replicates with SEM (error bars) *, values<0. (H) Chlorpromazine was diluted in DMEM+10% FBS to the concentrations indicated and then added to Huh 7.5 cells, plated the previous day in poly-D-lysine coated 96-well plates. Cells were incubated for 6 hours before chlorpromazine was removed and DMEM+10% FBS was added. A cell viability assay was carried out on cells incubated for 6 hours with chlorpromazine and on control cultures as described in Materials and Methods (0 hrs post treatment; dashed bars). An additional cell viability assay was carried out on chlorpromazine treated- and control cultures 48 hours post treatment (white bars). The % viability was calculated by relating absorbance at 490 nm determined for chlorpromazine treated cultures to the mean absorbance of three replicate untreated cultures. Bars represent the means of three replicates with SEM.

Figure 12:
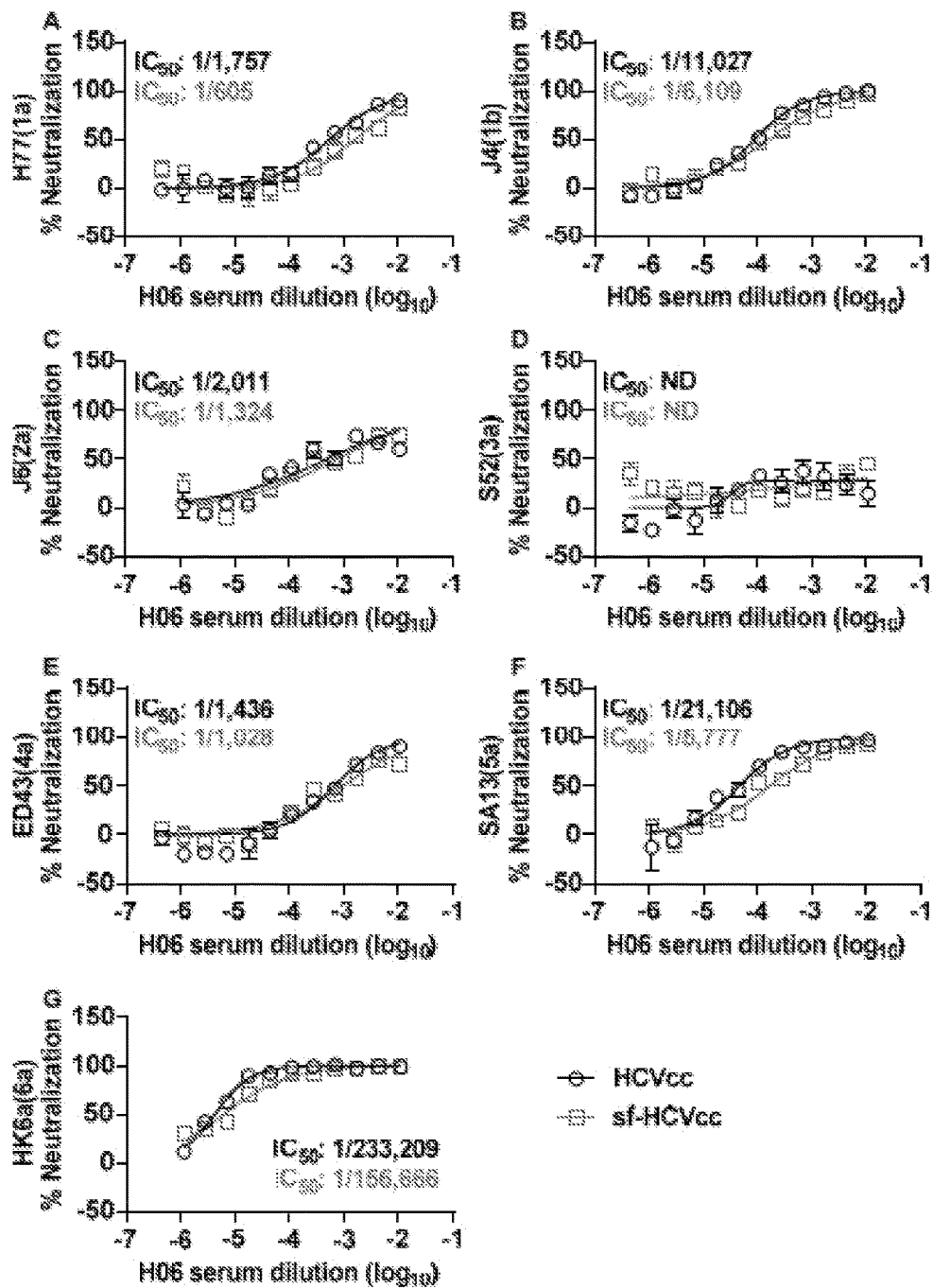

FIG. 12: HCVcc and sf-HCVcc show similar sensitivity to neutralization with genotype 1a chronic-phase patient serum. Genotype 1a serum H06 was diluted in DMEM+10% FBS as indicated. HCVcc (black circles) were diluted in DMEM+10% FBS and sf-HCVcc (grey squares) were diluted in AEM+10% FBS, mixed with H06 serum dilutions and incubated 1 hour at 37° C. Virus-serum mixes were added to Huh7.5 cells, plated the previous day onto poly-D-lysine coated 96 well plates. After 6 hours incubation, virus-serum mixes were removed and DMEM+10% FBS was added. Cells were fixed 48 hours post infection and stained, and the number of single HCV NS5A positive cells per well was determined by automated counting as described in Materials and Methods. The HCV Core-E2 sequences of all virus stocks used were determined by direct sequencing. Sequences were identical for HCVcc and sf-HCVcc of the same recombinant. Compared to the plasmid sequence, H77(1a) viruses had acquired amino acid change I348S and J4(1b) had acquired amino acid change V710L, both estimated to be present in the majority of viral genomes. The % neutralization was calculated by relating counts of experimental wells to the mean count of six replicate wells with untreated control virus. Data points are means of three replicates with SEM (error bars). Following logarithmic transformation of X-values, variable-slope sigmoidal dose-response curves were fitted [Y=Bottom+(Top−Bottom)/(1+ $10^{(Log10EC50-X) \times HillSlope}$)]. "Bottom" was constrained to "0" for all curves. "Top" was constrained to "100" for all curves in all panels except D; for these curves, median inhibitory concentrations (IC50) were calculated (black for HCVcc and grey for sf-HCVcc). ND, not determinable.

Figure 13:
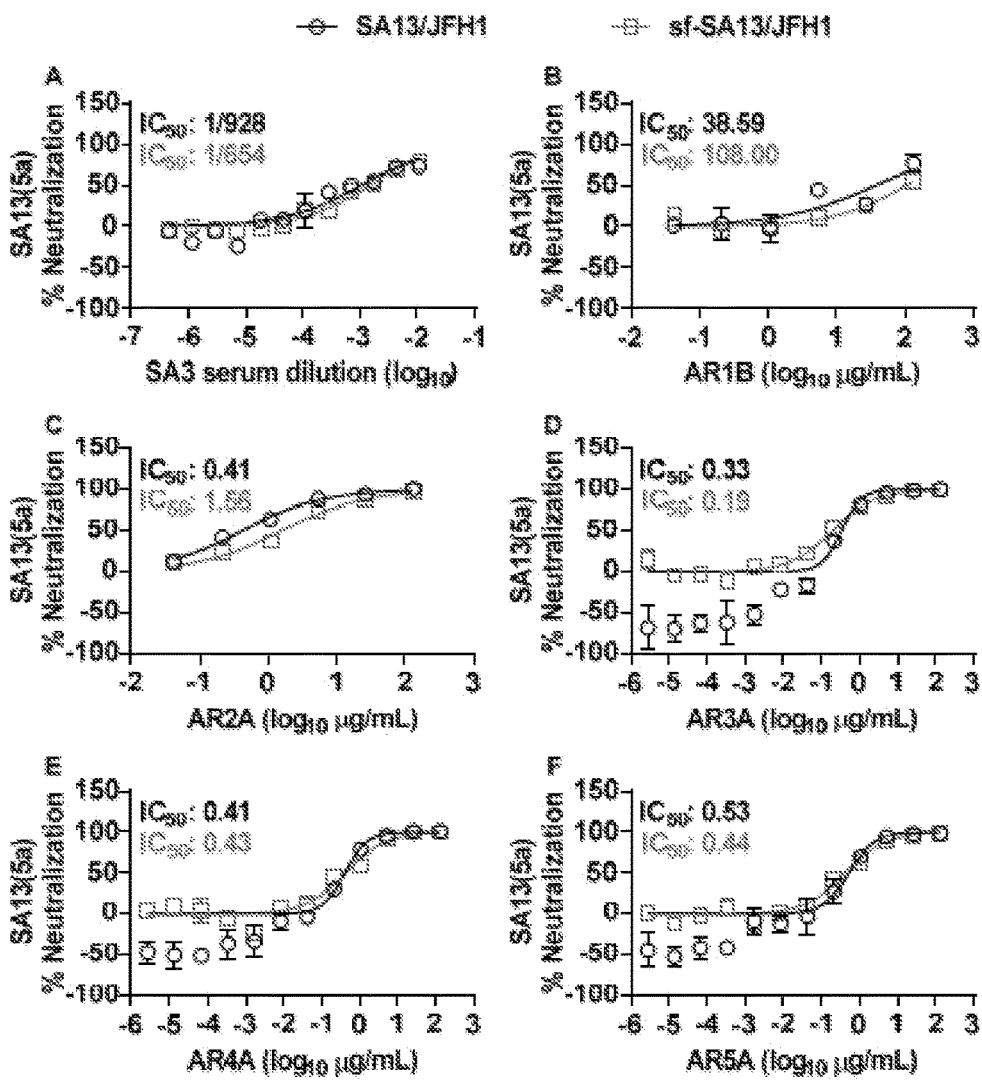

FIG. 13: SA13(5a) and sf-SA13(5a) show similar susceptibility to genotype 5a patient serum and human monoclonal antibodies. (A) Genotype 5a chronic phase serum SA3 or (B-F) monoclonal antibodies AR1B and AR2A-5A were diluted in DMEM+10% FBS as indicated. HCVcc (black circles) were diluted in DMEM+10% FBS and sf-HCVcc (grey squares) were diluted in AEM+10% FBS, mixed with SA3 serum, AR1B or AR2A-5A antibody dilutions and incubated 1 hour at 37° C. Virus-serum or virus-antibody mixes were added to Huh7.5 cells, plated the previous day in poly-D-lysine coated 96 well plates. After 6 hours incubation, virus-serum or virus-antibody mixes were removed and DMEM+10% FBS was added. Cells were fixed 48 hours post infection and stained, and the number of single HCV NS5A positive cells per well was determined by automated counting as described in Materials and Methods. The % neutralization was calculated by relating counts of experimental wells to the mean count of six replicate wells with untreated control virus. Data points are means of three replicates with SEM (error bars). Following logarithmic transformation of X-values, variable-slope sigmoidal dose-response curves were fitted [Y=Bottom+(Top−Bottom)/$^{(1+10(Log10EC50-X) \times HillSlope)}$]. "Bottom" was constrained to "0" for all curves. "Top" was constrained to "100" for all curves. Median inhibitory concentrations (IC50) were calculated (black for HCVcc and grey for sf-HCVcc).

Figure 2:
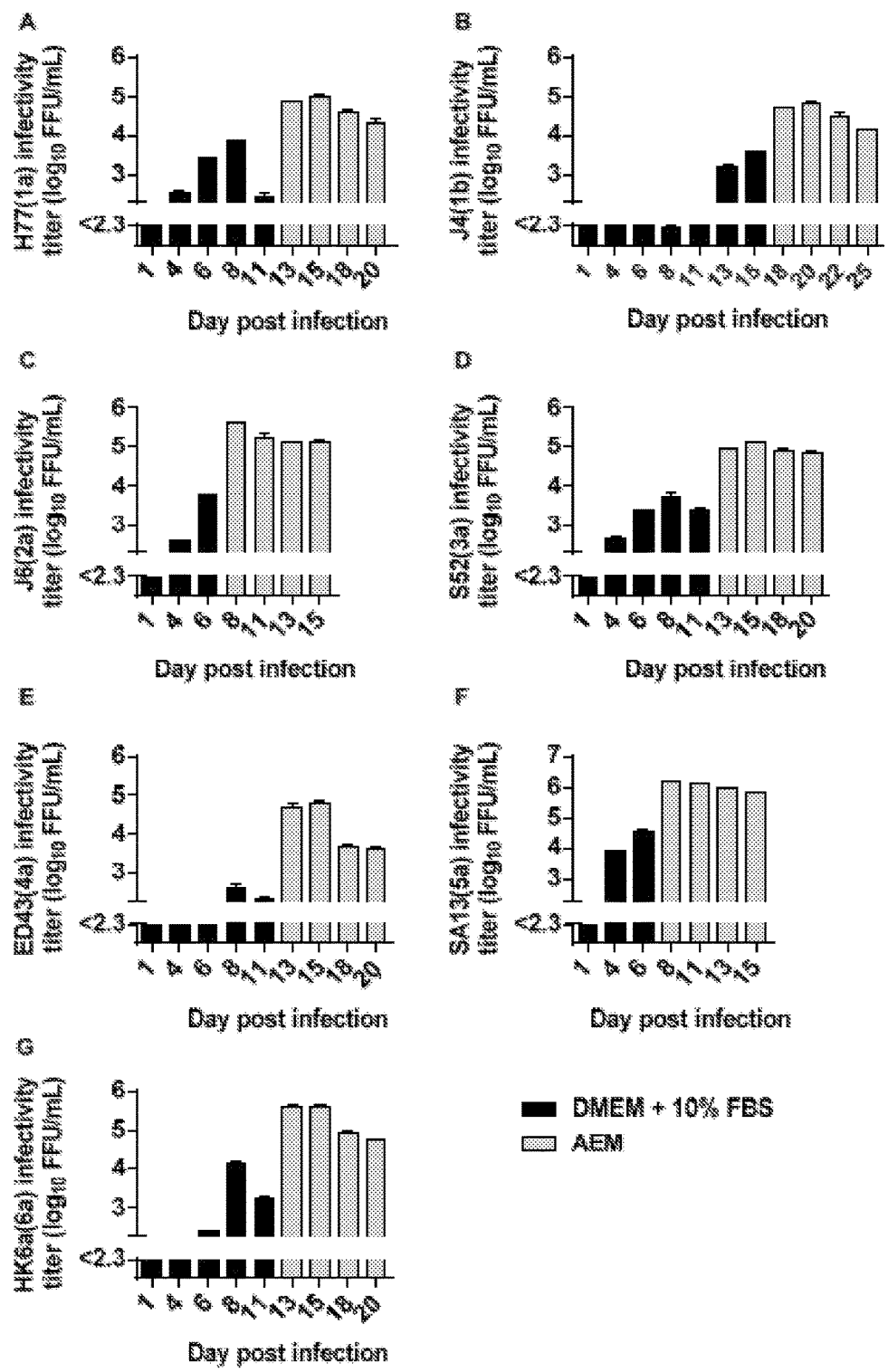

FIG. 14: Characteristics of genotype 1-6 sf-HCVcc virus stocks compared to HCVcc reference stocks. Serum-free cultures were infected and maintained as described in Materials and Methods (FIG. 2). For sf-HCVcc, supernatant HCV infectivity titers, Core antigen, and RNA titers were determined, and specific infectivities was calculated. Representative peak infectivity titers as well as Core and RNA titers from the same sample are shown. Core-E2 sequences were determined by direct sequence analysis as described in Materials and Methods. For sf-J6(2a), sf-552(3a), sf-ED43 (4a), sf-SA13(5a) and sf-HK6a(6a), Core-E2 sequences were identical to the plasmid sequence. The sf-H77(1a) had acquired the previously described amino acid change Y361H, estimated to be present in 50% of viral genomes; this change was also present in the H77(1a) HCVcc stock shown in this table. The sf-J4(1b) had acquired amino acid changes T578A and D584G, estimated to be present in the majority of viral genomes. For HCVcc, characteristics of references stocks (HCVcc ref. stocks) are reproduced from Gottwein et al. 2009.

a Isolate and genotype of Core-NS2 of the used JFH1-based recombinants is indicated. Recombinants are further described in Materials and Methods.

b For sf-HCVcc, supernatant infectivity titers were determined as FFU/mL by a cell culture-based titration assay as described in Materials and Methods. Values are means of three replicates.

c For sf-HCVcc, supernatant RNA titers were determined in the samples, for which infectivity titers are given, as IU/mL by Taq-Man PCR as described in Materials and Methods. Values are means of two replicates.

d Core titers were determined in the samples for which infectivity titers are given, as amol/mL using the ARCHITECT HCV Ag assay (Abbott).

e For sf-HCVcc, specific infectivity was calculated as FFU/IU by dividing supernatant infectivity titers with the corresponding RNA titers. For HCVcc, values were adapted from Gottwein et al. (2009) to FFU/IU by dividing supernatant infectivity titers with the corresponding RNA titers.

f Specific infectivity was calculated as FFU/amol Core by dividing supernatant infectivity titers with the corresponding Core titers.

g The peak infectivity titer of this SA13(5a) reference stock was lower than what we typically observe. Typically, peak titers for SA13(5a) are ~5 log 10 FFU/mL (FIG. 3A).

Figure 15:
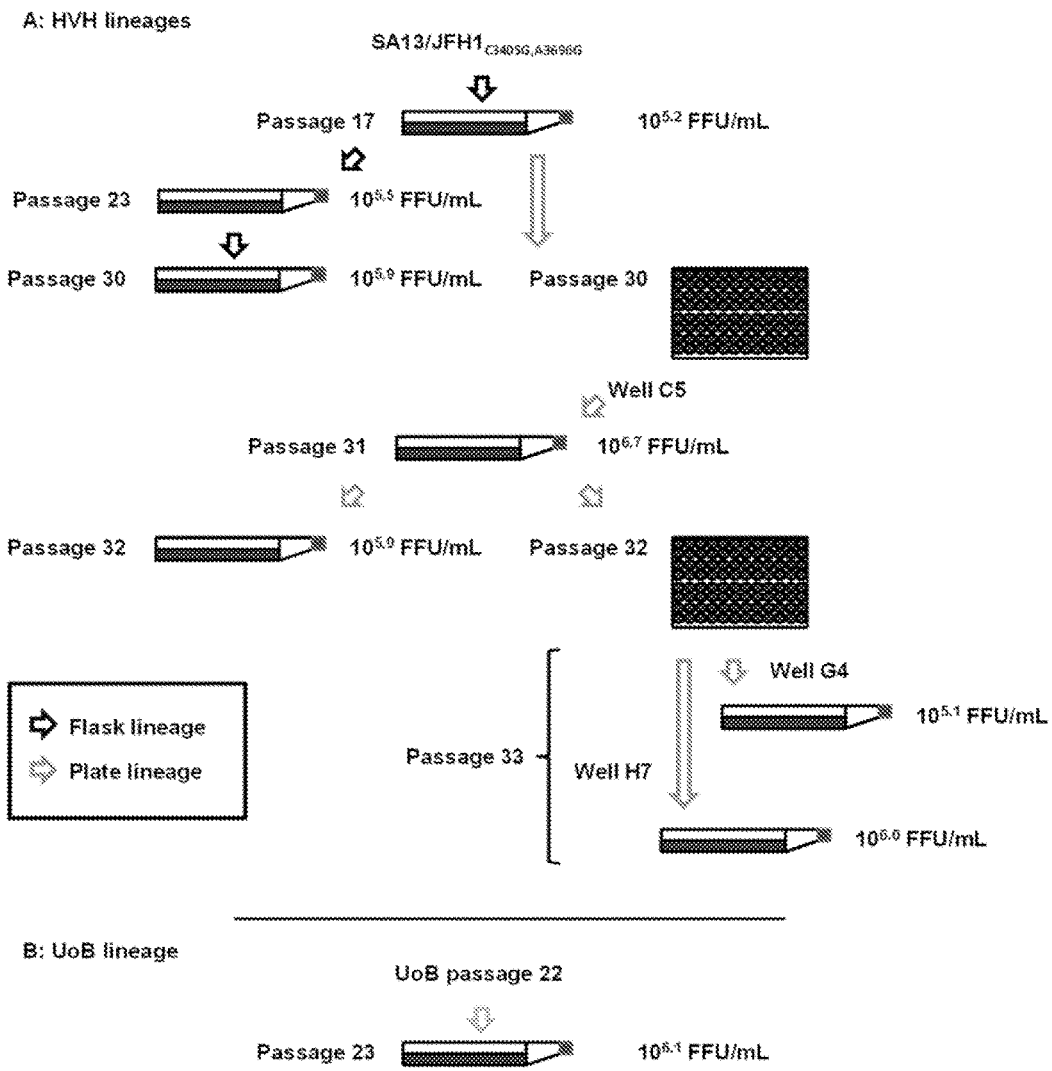

FIG. 15. Flow chart of serial passage lineages of a genotype 5a Core-NS2 recombinant. (A) A previously described 2nd passage SA13/JFH1C3405G,A3696G virus was serially passaged in cell culture flasks for a total of 17 passages as described in Materials and Methods (black arrows). From the 17th passage, two different lineages were continued, the flask lineage (black arrows) and the plate lineage (blue arrows). For the flask lineage, virus was passaged in cell culture flasks as described in Materials and Methods until passage 30. In the plate lineage, virus was passaged in 96-well plates as described in Materials and Methods until passage 30. From the passage 30 plate, six individual wells were used to infect Huh7.5 cultures to generate passage 31 stocks. From the displayed passage 31 stock (SA13/JFH1p31/C5), a 32nd passage was made. Furthermore, SA13/JFH1p31/C5 was subjected to endpoint titration in a 96-well plate (passage 32) in order to obtain individual quasispecies. Six individual wells were selected at the highest possible dilution (endpoint) and used to infect Huh7.5 cultures to generate passage 33 stocks. Representative stocks and their peak titer are shown. (B) Simultaneously, an independently serially passaged passage 22 SA13/JFH1C3405G,A3696G stock was received from The University of Birmingham (UK) (UoB lineage, green arrow). This virus stock was used to generate a passage 23-virus stock (SA13/JFH1p23/UoB). (A and B) Selected serially passaged virus stocks from all lineages are shown. The ORF of RNA genomes recovered from these stocks were all sequenced (FIG. 14). Furthermore, the viruses were infectivity titrated (FIG. 16, FIG. 2, and data not shown); titers are given as FFU/mL.

FIG. 16. Serial passage of SA13/JFH1C3405G,A3696G resulted in increased HCV infectivity titers. (A) Flask lineage peak infectivity titers. SA13/JFH1C3405G,A3696G was serially passaged in Huh7.5 cell cultures kept in culture flasks as described in Materials and Methods; passage number is indicated. Supernatants were collected and infectivity titers were determined. (B) Plate lineage peak infectivity titers. A 96-well plate was infected with virus from the 17th passage of the flask lineage as described in Materials and Methods. Virus was passaged in 96-well plates until a passage 30 plate was generated. From the passage 30 plate, individual wells were used to infect Huh7.5 cell cultures in order to generate passage 31 stocks. Passage cultures are named according to passage number and the number of the well, from which supernatant for infection was recovered (A12, B7, C5, D11, E1 and G2). Passage 31 supernatants were collected and infectivity titers were determined. (C) Endpoint culture peak infectivity titers. From the passage 31 stock SA13/JFH1p31/C5, 12 replicate serial dilutions were made from 10-1 to 10-8. Supernatants from 6 passage 32 cultures containing 1-2 FFU at dilutions of 10-7-10-8 were used to infect naive Huh7.5 cell cultures. In 4/6 passage 33 cultures, viral spread was observed. These cultures are named according to passage (33) and the number of the well, from which supernatant for infection was recovered (G2, H3, G4 and H7). From these, supernatants were collected and infectivity titers were determined. (A-C) Supernatant infectivity titers are shown as means of three replicates with standard error of the mean (SEM). An overview of the serial passage lineages can be seen in FIG. 15.

FIG. 17. Coding mutations of adapted SA13(5a) constructs. Positions are numbered according to the sequence of pSA13/JFH1. Corresponding H77 (AF009606) absolute reference numbers are given. Only positions with coding mutations present as a 50/50 quasispecies or dominant in at least one isolate are shown. Dashes indicate identity with original plasmid sequence. Positions with quasispecies are written with the dominant sequence in upper case and the minor sequence in lower case. 50/50 quasispecies are shown with two upper case letters. Shaded positions were introduced back into pSA13/JFH1 in different combinations. Positions shaded in black represent original SA13/JFH1 cell culture adaptive mutations described previously.

b Common 17th passage used for subsequent flask- and plate lineage.

c Virus stocks are designated according to their passage-well number used to infect culture. Accordingly, a 31st passage virus stock derived from well C5 of a 96-well plate is designated p31/C5.

d Adapted virus stock acquired from the University of Birmingham (UK).

e HCV infectivity titers were determined as described in Materials and Methods. Peak infectivity titers are displayed as log 10 FFU/mL.

FIG. 18. Adapted SA13/JFH1 constructs show accelerated spread, higher infectivity titers and larger FFUs after transfection and passage in Huh7.5 cells. (A) Different SA13/JFH1 constructs (see figure label) were engineered; HCV RNA transcripts were transfected into Huh7.5 cell cultures as described in Materials and Methods. From transfection cultures, supernatants were collected and infectivity titers were determined. (B) Supernatants from the stocks generated from experiments shown in FIG. 3A, collected at the peak of infection, were used to infect Huh7.5 cell cultures at an MOI of 0.003 as described in Materials and Methods. From these, supernatants were collected and infectivity titers were determined. (A, B) Supernatant infectivity titers are shown as means of three replicates with SEM. The lower limits of detection were determined for each individual experiment and are indicated by y-axis break. #, infectivity titer not determined due to massive HCV induced cell death in the culture. (C) Individual foci sizes (mm2) generated by infection of Huh7.5 cells with either SA13/JFH1C3405G,A3696G (black bar, [n=290 for transfection; n=162 for infection]) and SA13/JFH1Core-NS5B (grey bar, [n=B149 for transfection; n=151 for infection]) transfection supernatants (top panel) or infection supernatants (bottom panel), were determined automatically as described in Materials and Methods. Foci size is shown as the mean of n (see above) replicates with SEM. * indicates p=0.0001. ** indicates p<0.0001. p-values were determined using the non-parametric Mann-Whitney test.

FIG. 19. Comparison between adapted SA13/JFH1 virus stocks and serially passaged SA13/JFH1 supernatants reveal SA13/JFH1Core-NS5B as the fittest adapted recombinant. Second passage virus stocks from adapted recombinants, serially passaged virus stocks and control virus stock J6/JFH1 (see figure label) were titrated three times independently as described in Materials and Methods, in order to determine an accurate mean infectivity titer (data not shown). Huh7.5 cell cultures were infected with these stocks at an (A) MOI of 0.003 or (B) MOI of 0.0003. From these, supernatants were collected and infectivity titers were determined. Supernatant infectivity titers are shown as means of three replicates with SEM. The lower limits of detection were determined for each individual experiment and are indicated by y-axis break.

Figure 20:
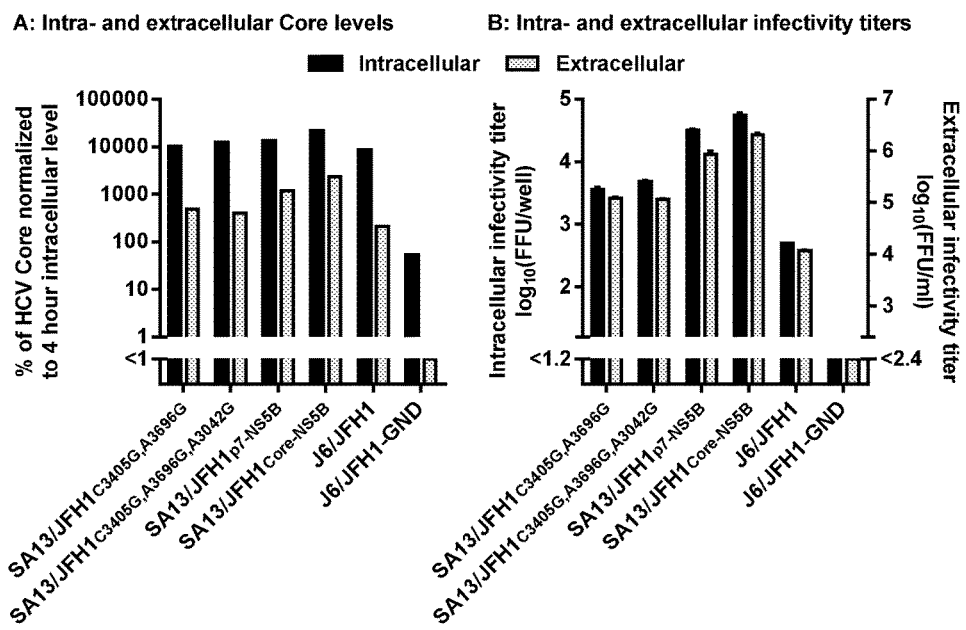

FIG. 20. Adaptive mutations confer increased HCV assembly. S29 cells were transfected with the constructs indicated in the figure label as described in Materials and Methods. (A) Intra- (black) and extracellular (grey) Core values were determined 48 hours post transfection as described in Materials and Methods. Core values were normalized to intracellular Core measured 4 hours post transfection. (B) Intracellular infectivity titers (black), determined 48 hours post transfection, are shown as the means (FFU/well) of three replicates with SEM and extracellular infectivity titers (grey), determined 48 hours post transfection, are shown as means (FFU/ml) of three replicates with SEM. The lower limits of detection were determined for each individual experiment and are indicated by y-axis break.

Figure 21:
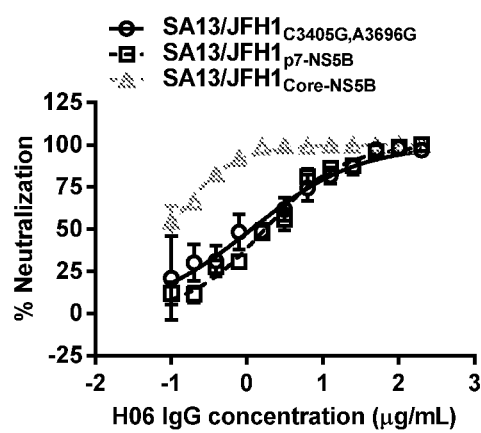

FIG. 21. SA13/JFH1Core-NS5B showed increased sensitivity to neutralization by patient IgG. Previously described purified H06 IgG was diluted in complete DMEM and mixed 1:1 with 200 FFU of the indicated 3rd passage virus stocks (FIG. 19A), and incubated for 1 hour at 37° C. IgG-virus mixes were added to Huh7.5 cells, plated the previous day onto poly-D-lysine coated 96-well plates. After 6 hours incubation, IgG-virus mixes were removed and complete DMEM was added to all wells. Cells were fixed 48 hours post infection and stained, and the number of single HCV NS5A positive cells per well was determined by automated counting as described in Materials and Methods. The % neutralization was calculated by relating counts of experimental wells to the mean count of six replicate wells with untreated control virus. Data points are means of three replicates with SEM. Following logarithmic transformation of X-values, variable-slope sigmoidal concentration-response curves were fitted [Y=Bottom+(Top−Bottom)/(1+ $10^{(Log10EC50-X) \times HillSlope}$)]. "Bottom" was constrained to 0 and "Top" was constrained to 100.

Figure 22:
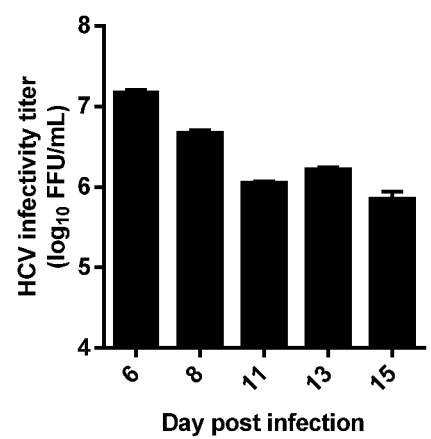

FIG. 22. AEM culture increased infectivity titers of SA13/JFH1p31/C5. Huh7.5 cells were infected with SA13/JFH1p31/C5 and kept in complete DMEM as described in Materials and Methods. At day 4 post infection, complete DMEM was replaced by AEM as described in Materials and Methods. AEM supernatants were harvested without splitting the cells at the indicated time points. Supernatant infectivity titers are shown as means of three replicates with SEM.

FIG. 23. Peak infectivity titers from kinetics experiment.
 a Third passage virus stocks generated as described in FIG. 4.
 b Serially passaged virus supernatants generated independently in two different laboratories (see FIG. 15).
 c Control virus stock.
 d The day post infection corresponding to the highest recorded peak titer (see FIG. 19).
 e HCV infectivity titers were determined as described in Materials and Methods. Peak infectivity titers are displayed as log 10 FFU/mL.

FIG. 24. Multi-step purification and concentration procedure—method 1. We produced 5.8 L of HCV containing serum-free cell culture supernatant from Huh7.5 cell cultures infected with the adapted genotype 5a (isolate SA13) Core-NS2 JFH1-based recombinant. This starting material contained a total of approximately 9.1 log FFU. We first carried out cross-flow filtration using Vivaflow filters (Sartorius) with 100 kDa cut-off for purification from low-molecular proteins and up-concentration to 21 mL. During this step, approximately 43% of infectious HCV was recovered. We then carried out 3-cushion iodixanol ultracentrifugation for purification and further up-concentration to 7.5 mL. During this step, approximately 69% of infectious HCV was recovered. Next, we carried out ultracentrifugation pelleting for purification from iodixanol and up-concentration to 0.6 mL. During this step, approximately 24% of infectious HCV was recovered. We then carried out iodixanol gradient centrifugation for purification, resulting in 1.7 mL. During this step, approximately 100% of infectious HCV was recovered. At last, we carried out sephadex chromatography for purification from iodixanol, resulting in 4.5 mL. During this step, approximately 98% of infectious HCV was recovered. In total, approximately 8 log FFU were recovered, equivalent to a total recovery of 8%. To the right, a silver staining of a protein gel is shown, on which samples obtained after the individual steps were run.

Figure 25:
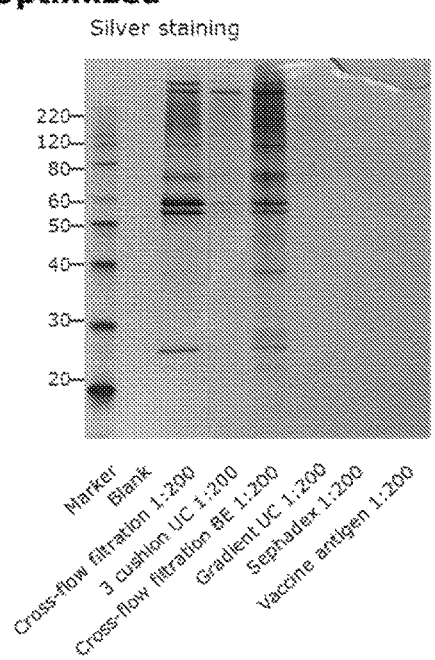

FIG. 25. Optimized multi-step purification and concentration procedure—method 2. We produced 8.7 L of HCV containing serum-free cell culture supernatant from Huh7.5 cell cultures infected with the adapted genotype 5a (isolate SA13) Core-NS2 JFH1-based recombinant. This starting material contained a total of approximately 10.1 log FFU. We first carried out cross-flow filtration using mPES MiniKros® Sampler Filter Modules 20 cm with 500 kDa cut-off (SpectrumLabs) for purification from low-molecular proteins and up-concentration to 32 mL. During this step, approximately 100% of infectious HCV was recovered. We then carried out 3-cushion iodixanol ultracentrifugation for purification and further up-concentration to 7.5 mL. During this step, approximately 67% of infectious HCV was recovered. Next, we carried out small-scale cross-flow filtration using mPES MicroKros® Modules (Spectrum labs) for purification from iodixanol and up-concentration to 1 mL. During this step, approximately 97% of infectious HCV was recovered. We then carried out iodixanol gradient centrifugation for purification, resulting in 1.7 mL. During this step, approximately 48% of infectious HCV was recovered. At last, we carried out sephadex chromatography for purification from iodixanol, resulting in 4.6 mL. During this step, approximately 60% of infectious HCV was recovered. In total, approximately 9.5 log FFU were recovered, equivalent to a total recovery of 25%. To the right, a silver staining of a protein gel is shown, on which samples obtained after the individual steps were run.

Figure 26:
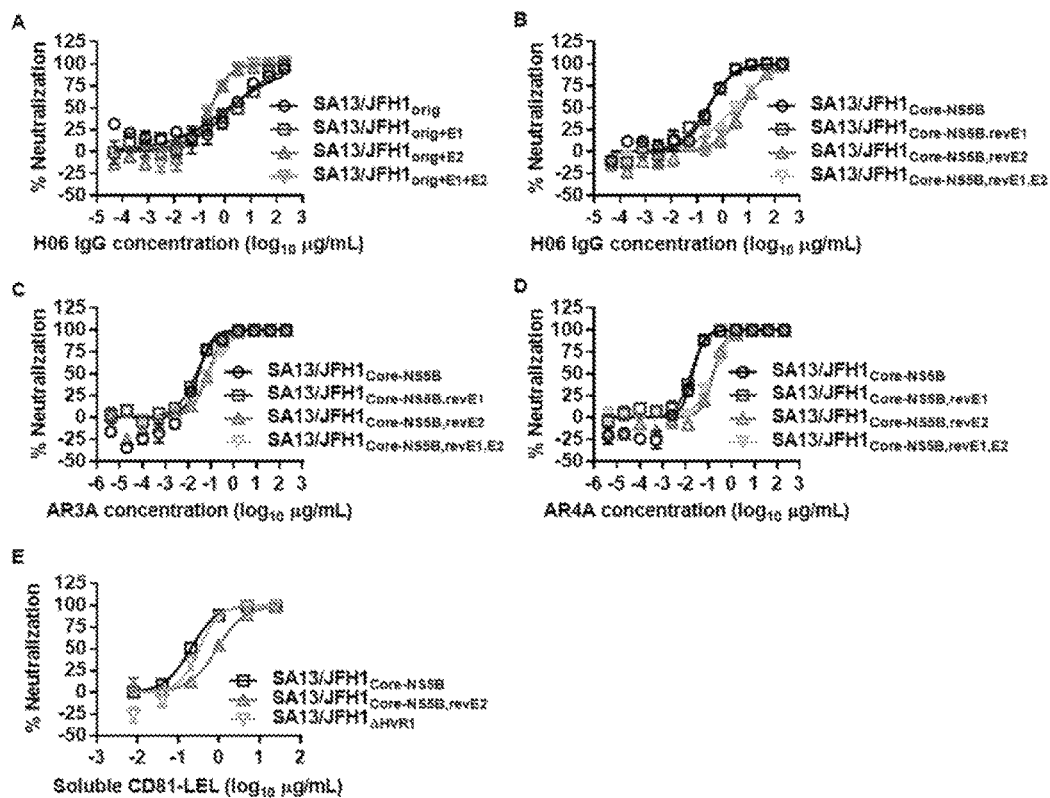

FIG. 26. Sensitivity to neutralization is affected by a single putative adaptive aa change in E2. (A and B) H06 IgG, (C) AR3A, (D) AR4A and (E) soluble CD81-LEL was mixed and incubated for 1 hour with the indicated viruses as described in Materials and Methods. Neutralization reactions were added to Huh7.5 cells and incubated for 3 hours. Neutralization reactions were removed and complete DMEM was added to all wells. Cells were fixed 48 hours post infection and stained, and the number of single HCV NS5A positive cells per well was determined by automated counting as described in Materials and Methods. The % neutralization was calculated by relating counts of experimental wells to the mean count of six replicate wells with untreated control virus. Data points are means of three replicates with SEM. Following logarithmic transformation of X-values, variable-slope sigmoidal concentration-response curves were fitted [Y=Bottom+(Top−Bottom)/(1+$10^{(Log10EC50-X) \times HillSlope}$)]. "Bottom" was constrained to 0 and "Top" was constrained to 100. (A and B) All neutralizations were performed in the same assay but are split in separate panels for visualization purposes. (A-D) IC50 values of individual recombinants are shown in FIG. 27.

Figure 27:
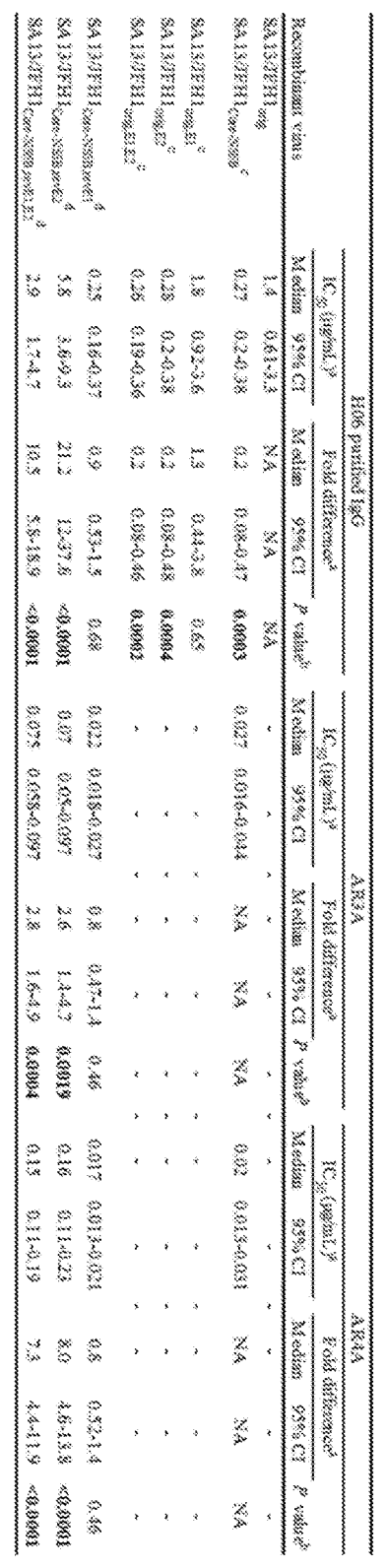

FIG. 27. Neutralization of SA13 Core-NS2 recombinants using chronic phase patient IgG and human monoclonal antibodies. Neutralization assays were performed using IgG purified from serum from genotype 1a infected Patient H, taken 29 years after acute infection (H06) and human monoclonal antibodies AR3A and AR4A, as described in Materials and Methods. NA, not applicable. Dash (-) indicates no available data.

a Median IC50 and median fold differences with 95% confidence interval were calculated as described in Materials and Methods. For calculation of fold differences, the IC50 obtained for the respective recombinant was related to the IC50 obtained for either SA13/JFH1orig or SA13/JFH1Core-NS5B as specified below.

b P values were determined using Z test as described in Materials and Methods. P values<0.005 are shown in bold.

c For statistical analyses, these recombinants were related to the SA13/JFH1orig recombinant.

d For statistical analyses, these recombinants were related to the SA13/JFH1Core-NS5B recombinant.

Figure 28:
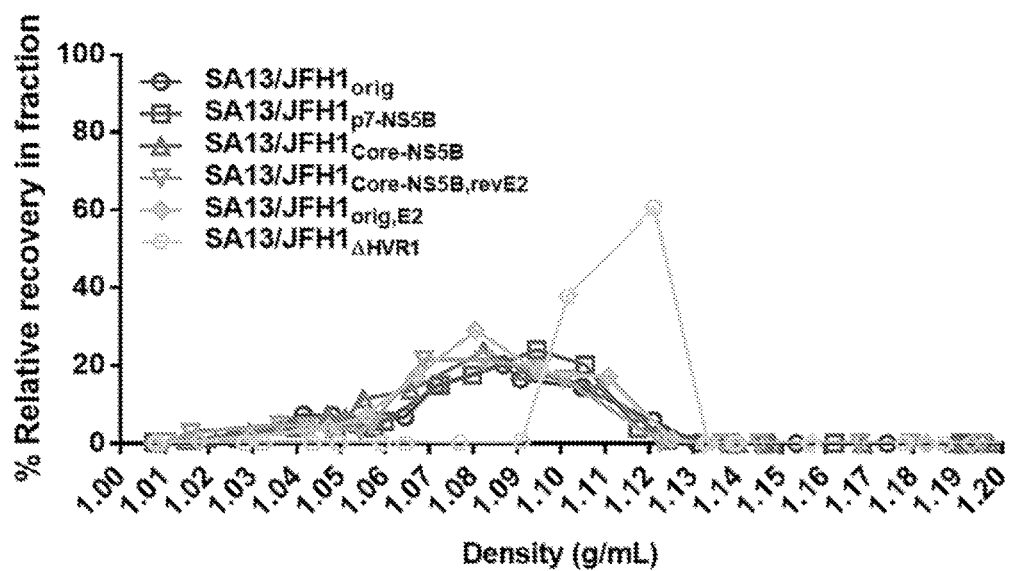

FIG. 28. Adaptive mutations do not affect buoyant density of infectious HCVcc particles. First passage virus stocks of the indicated viruses were loaded on top of pre-formed 10-40% iodixanol gradient and subjected to ultracentrifugation as described in Materials and Methods. Fractions were collected from the bottom of the gradients and analysed by density determination and infectivity titration as described in Materials and Methods. Relative recovery of infectious virus per fraction (%) was calculated by relating the amount of infectious virus detected in each fraction to the total amount of infectious virus collected, and is plotted against the density determined for each fraction. Only fractions with densities <1.20 g/mL are shown.

Figure 29:
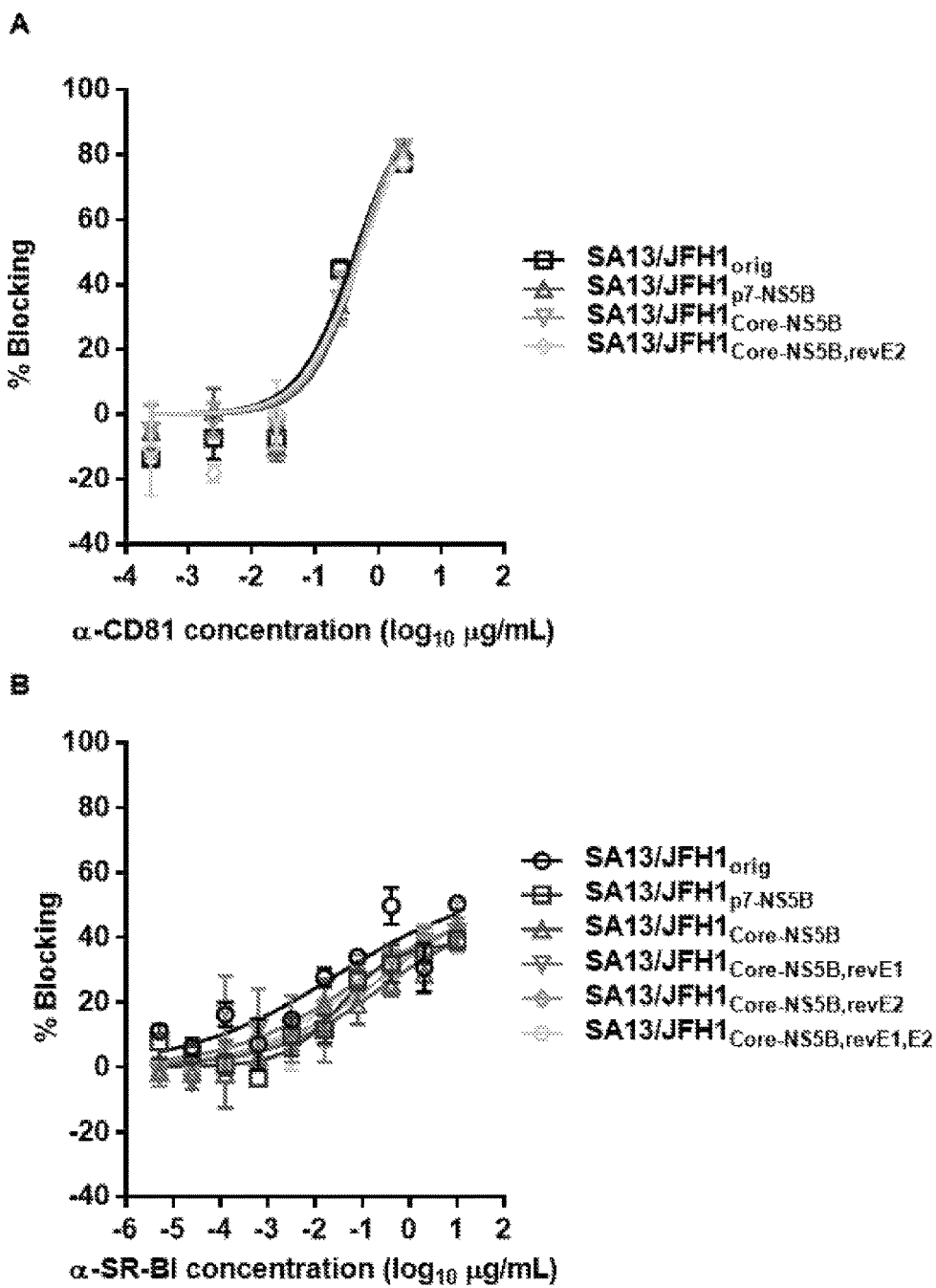

FIG. 29. Adaptive mutations do not affect sensitivity to CD81 and SR-BI blocking. (A) α-CD81 or (B) α-SR-BI was added to Huh7.5 cells at the given concentrations and incubated for 1 hour. Following incubation, the indicated viruses were added to the Huh7.5 cells, as described in Materials and Methods, and incubated for 3 hours. Antibody and virus was removed and complete DMEM was added to all wells. Cells were fixed 48 hours post infection and stained, and the number of single HCV NS5A positive cells per well was determined by automated counting as described in Materials and Methods. The % blocking was calculated by relating counts of experimental wells to the mean count of eight replicate wells with untreated control virus. Data points are means of three replicates with SEM. Following logarithmic transformation of X-values, variable-slope sigmoidal concentration-response curves were fitted [Y=Bottom+(Top−Bottom)/(1+$10^{(Log10EC50-X) \times HillSlope}$)]. "Bottom" was constrained to 0. For CD81 blocking, a "Top" constraint of 100 was introduced.

The present invention will now be described in more detail in the following.

DETAILED DESCRIPTION OF THE INVENTION

The present inventors have now surprisingly found that specific high-titer viruses grown in serum-free medium can be purified, up-concentrated and inactivated to generate a whole viral inactivated vaccine stock that can be used for immunizing. These stocks will be key in facilitating virological studies, and for vaccine development.

Thus, it is an object of the present invention to provide such stocks.

One aspect of the present invention relates to a method of obtaining a whole virus vaccine candidate stock, the method comprising the steps of providing a cell culture supernatant comprising virus particles, purification and/or up-concentration of the virus particles in the cell culture supernatant, optionally a second or subsequent steps of purification and/or up-concentration of the product of the previous round of purification and/or up-concentration, optionally collection of one or more specific fractions obtained from the purification and/or up-concentration, and obtaining the whole virus vaccine candidate stock.

Example 3 shows experiments using such method.

The second or subsequent steps purification and/or up-concentration of the cell culture supernatant may be done with collection or one or more specific fractions obtained from the purification and/or up-concentration between each round.

The rounds of purification and/or up-concentration or collection of one or more specific fractions may be a single round, two rounds, three rounds, four rounds, five rounds, or six, 8, 10, 15 or 20 rounds.

Viral particles grown in serum free medium have an advantage because they have favorable density profiles.

Thus, in one embodiment of the present invention is the cell culture grown in a serum free medium.

In another embodiment of the present invention is the medium adenovirus expression medium optionally supplemented with penicillin 100 U/mL and streptomycin 100 µg/mL.

In a further embodiment of the present invention is the cell culture grown under optimized conditions such as but not limited to cell factories or in bioreactors, on optimized surfaces, in suspension or on beads In yet another embodiment of the present invention are the cells in the cell culture Huh7.5 cells.

In another embodiment of the present invention is the virus non-enveloped or enveloped.

In another embodiment of the present invention the virus belongs to the Flaviviridae family.

In a further embodiment of the present invention is the virus a virus selected from the group consisting of a flavivirus, a hepacivirus, a pegivirus, and a pestivirus.

In yet another embodiment of the present invention is the virus a virus selected from the group consisting of yellow fever virus, west nile virus, dengue fever virus, GB virus B, GB virus A, GB virus C, GB virus D, bovine viral diarrhea virus, classical swine fever, hog cholera, HAV, HBV, HCV, HCVcc, sf-HCVcc and specific genotypes of HCV selected from genotypes 1-7.

In yet another embodiment of the present invention is the virus a virus selected from the group consisting of recently discovered hepatitis C virus-like viruses belonging to the hepaci- and pegivirus genera, which were identified in domesticated animals (dogs and horses) and small wild mammals (rodents and bats).

The HCV may also be any other HCV described herein.

In a further embodiment of the present invention is the purification and/or up-concentration performed using a method selected from the list consisting of centrifugation, ultracentrifugation, density gradient ultracentrifugation, iodixanol cushion centrifugation, sucrose cushion centrifugation, nycodenz cushion centrifugation, cesium chloride cushion, iodixanol gradient centrifugation, sucrose gradient centrifugation, nycodenz gradiend centrifugation, cesium chloride gradient centrifugation, ultracentrifugation pelleting, filtration, clarification, microfiltration, nanofiltration, direct filtration, cross-flow filtration, ultrafiltration, precipitation, polyethylene glycol precipitation, polymer precipitation, polyelectrolyte precipitation, chromatography, column chromatography, porous particle chromatography, membrane chromatography, monolith chromatography, size exclusion chromatography, ion exchange chromatography, and dialysis. In a further embodiment of the present invention there are 1, 2, 3, 4, 5, 6, or 7 iodixanol or sucrose cushions.

Filtration may cover clarification and endotoxin removal. This can be done using 3M Purification Inc.™ filtration system. The 3M Purification Inc.™ filtration system includes but is not limited to depth filters "Zeta Plus", "Zeta Plus EXT Series" and "Betapure NT-P™" which can be used for clarification, adsorption-based separation systems "Zeta Plus ZA", which can be used for endotoxin removal, and surface filters "LifeASSURE SP", which can be used for endotoxin removal.

In a preferred embodiment of the present invention there are 3 or 4 cushions.

Cushions can have different densities, for example, iodixanol cushions could be 10%, 28% m 60%, 20, 30 or 70%.

In another embodiment of the present invention is the filtration selected from the list consisting of conventional direct or dead end filtration, depth filtration, cut-off filtration, microfiltration, nanofiltration, ultrafiltration, small-scale cross-filtration, and cross-flow filtration.

Different filters can be applied and they may have different pore size, greater surface or have a higher molecular weight cut-off to allow purification of bigger proteins.

In another embodiment of the present invention is the cross-flow filtration selected from the group of hollow-fiber filters such as but not limited to MicroKros® Filter Modules, MidiKros® Filter Modules, MidiKros® TC Filter Modules, MiniKros® Sampler Filter Modules, MiniKros® Filter Modules, KrosFlo® Filter Modules, KrosFlo® Max Filter Modules and Vivaflow. Different molecular weight cut-offs such as 500 kDa, 300 kDA, 200 kDa, 100 kDa, 70 kDa, 50 kDa, 30 kDa, 10 kDa, 5 kDa, 3 kDa, 1 kDa might be used. Filters with different surface areas might be used.

In another embodiment of the present invention is the precipitation polyethylene glycol (PEG) precipitation.

In another embodiment of the present invention is the ultracentrifugation selected from the group consisting of iodixanol gradient ultracentrifugation, sucrose gradient ultracentrifugation, and ultracentrifugation pelleting.

The gradient ultracentrifugations can be done at different ranges, for example 10-40% 5-60%, 1-80%, 20-60%, or 20-70%.

In another embodiment of the present invention is the chromatography selected from the group consisting of column chromatography, porous particle chromatography, membrane chromatography, monolith chromatography, size exclusion chromatography, ion exchange chromatography, affinity chromatography or sephadex chromatography.

A further embodiment of the present invention relates to the method of the present invention wherein the steps are providing a cell culture supernatant comprising virus particles, purification and/or up-concentration of the cell culture supernatant using cross-flow filtration, purification and/or up-concentration of the cell culture supernatant using 3-cushion ultracentrifugation, collection of 3 fractions and using the middle one, purification and/or up-concentration of the cell culture supernatant using ultracentrifugation pelleting, purification and/or up-concentration of the cell culture supernatant using iodixanol gradient ultracentrifugation, collection of 18 fractions and use the 3 containing most HCV, purification and/or up-concentration of the cell culture supernatant using sephadex chromatography, and obtaining the whole virus vaccine candidate stock.

Another embodiment of the present invention relates to the method of the present invention wherein the steps are providing a cell culture supernatant comprising virus particles, purification and/or up-concentration of the cell culture supernatant using cross-flow filtration, purification and/or up-concentration of the cell culture supernatant using 3-cushion ultracentrifugation, collection of 3 fractions and use the middle one, purification and/or up-concentration of the cell culture supernatant using small-scale cross-flow filtration, purification and/or up-concentration of the cell culture supernatant using iodixanol gradient ultracentrifugation, collection of 18 fractions and use the 3 containing most HCV, purification and/or up-concentration of the cell culture supernatant using sephadex chromatography, and obtaining the whole virus vaccine candidate stock.

The fractions collected may be examined to determine those that contain most HCV by methods known to the skilled person.

One, two, three or more fractions may be used in the methods and one, two, three, four, five, ten, 15, 18 or 20 fractions may be collected.

Another embodiment of the present invention relates to the whole virus vaccine candidate stock obtained from the methods of the present invention. This stock will contain a high concentration of whole virus.

Another aspect of the present invention relates to a method of obtaining a whole virus vaccine inactivated candidate stock, the method comprising the step of inactivation of the whole virus vaccine candidate stock of the present invention to obtain a whole virus vaccine inactivated candidate stock.

In another embodiment of the present invention is the inactivation performed using UV radiation, UV combined with photosensitizer, paraformaldehyde, or betapropiolactone, or gamma-irradiation.

Another embodiment of the present invention relates to the whole virus vaccine inactivated candidate stock obtained from the methods of the present invention.

Another aspect of the present invention relates to a pharmaceutical composition comprising the whole virus vaccine inactivated candidate stock of the present invention formulated with one or more adjuvant(s), excipient(s) and/or carrier(s).

Such pharmaceutical compositions are ideal for use in immunizing and vaccination. They will also be key in facilitating virological studies, and for vaccine development.

Adaptive Mutations

The present invention advantageously provides hepatitis C virus (HCV) nucleotide and amino acid sequences.

These sequences are capable of replication, expression of functional HCV proteins, infection in vivo and/or in vitro for development of antiviral therapeutics and diagnostics.

Nucleic Acid Molecules (cDNA Clones and RNA Transcripts)

The present invention is directed towards an isolated nucleic acid molecule which encodes a human hepatitis C virus, comprising at least one amino acid mutation selected from the group consisting of R104Q, R114W, I178V, V187A, V235L, T385P, H777Y, L782V, I850L, V866A, Y900C, A1021G, K1118R, A1406G, V1635I, V1692A, A1862V, A1900G, P1908L, T1936A, N2034D, T2055I, D2225G, E2238G, S2248P, V2252A, L2266P, M2275T, I2340T, S2357L, C2419S, A2500S, N2537T, C2723S, V2841A, and L2993H according to the H77 reference sequence with GenBank accession number AF009606.

In one embodiment of the present invention is the isolated nucleic acid molecule capable of infectivity in vivo.

In another embodiment of the present invention is the hepatitis C is derived from genotype 5a Core-NS2 JFH1-based recombinant SA13/JFH1.

In another embodiment of the present invention is the hepatitis C of a genotype selected from the group consisting of genotype 1, 2, 3, 4, 5, 6, and 7 as well as their subtypes a, b, c, d, e, and f.

The hepatitis C virus can be either full length or an intra- or intergenotypic recombinant.

The terms "isolate" and "strain" are used herein interchangeably.

Another aspect of the present invention relates to an isolated amino acid molecule which encodes a human hepatitis C virus wherein the hepatitis C virus is derived from genotype 5a, comprising at least one amino acid mutation selected from the group consisting of R104Q, R114W, I178V, V187A, V235L, T385P, H777Y, L782V, I850L, V866A, Y900C, A1021G, K1118R, A1406G, V1635I, V1692A, A1862V, A1900G, P1908L, T1936A, N2034D, T2055I, D2225G, E2238G, S2248P, V2252A, L2266P, M2275T, I2340T, S2357L, C2419S, A2500S, N2537T, C2723S, V2841A, and L2993H according to the H77 reference sequence with GenBank accession number AF009606.

The HCV can comprise all of the adaptive mutations or a certain subgroup such as 16, such as 14, such as 12, such as 10, such as 8, such as 6, such as five, such as 4, such as 3, such as 2, such as 1.

In one aspect of the present invention is a single of the adaptive mutations listed above comprised in the HCV.

Another aspect of the present invention relates to an isolated amino acid molecule that has an open reading frame (ORF) amino acid sequence with 90% sequence identity to the sequences of the present invention.

As commonly defined "identity" is here defined as sequence identity between genes or proteins at the nucleotide or amino acid level, respectively.

Thus, in the present context "sequence identity" is a measure of identity between proteins at the amino acid level and a measure of identity between nucleic acids at nucleotide level. The protein sequence identity may be determined by comparing the amino acid sequence in a given position in each sequence when the sequences are aligned. Similarly, the nucleic acid sequence identity may be determined by comparing the nucleotide sequence in a given position in each sequence when the sequences are aligned.

To determine the percent identity of two amino acid sequences or of two nucleic acids, the sequences are aligned for optimal comparison purposes (e.g., gaps may be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100).

In one embodiment the two sequences are the same length.

In another embodiment the two sequences are of different length and gaps are seen as different positions.

One may manually align the sequences and count the number of identical amino acids. Alternatively, alignment of two sequences for the determination of percent identity may be accomplished using a mathematical algorithm. Such an algorithm is incorporated into the NBLAST and XBLAST programs of (Altschul et al. 1990). BLAST nucleotide searches may be performed with the NBLAST program, score=100, wordlength=12, to obtain nucleotide sequences homologous to a nucleic acid molecules of the invention. BLAST protein searches may be performed with the XBLAST program, score=50, wordlength=3 to obtain amino acid sequences homologous to a protein molecule of the invention. To obtain gapped alignments for comparison purposes, Gapped BLAST may be utilised. Alternatively, PSI-Blast may be used to perform an iterated search which detects distant relationships between molecules. When utilising the NBLAST, XBLAST, and Gapped BLAST programs, the default parameters of the respective programs may be used. See http://www.ncbi.nlm.nih.gov. Alternatively, sequence identity may be calculated after the sequences have been aligned e.g. by the BLAST program in the EMBL database (www.ncbi.nlm.gov/cgi-bin/BLAST). Generally, the default settings with respect to e.g. "scoring matrix" and "gap penalty" may be used for alignment. In the context of the present invention, the BLASTN and PSI BLAST default settings may be advantageous.

The percent identity between two sequences may be determined using techniques similar to those described above, with or without allowing gaps. In calculating percent identity, only exact matches are counted.

An embodiment of the present invention thus relates to sequences of the present invention that have some degree of sequence variation.

In another embodiment, the nucleic acid comprises a sequence sharing at least 85% identity with that set forth in genotype 5a Core-NS2 SA13/JFH1 or H77, such as 90% identity, 91% identity, 92% identity, 93% identity, 94% identity, 95% identity, 96% identity, 97% identity, 98% identity, or 99% identity and comprising the adaptive mutations listed above.

It should be noted that while several of the sequences in the present application are DNA sequences, the present invention contemplates the corresponding RNA sequence, and DNA and RNA complementary sequences as well.

Thus, in cases where a DNA sequence is mentioned refers such DNA sequence also to the RNA equivalent i.e. with Ts exchanged with Us as well as their complimentary sequences.

In another embodiment, the HCV nucleic acid is a DNA that codes on expression or after in vitro transcription for a replication-competent HCV RNA genome, or is itself a replication-competent HCV RNA genome.

In one embodiment, the HCV nucleic acid of the invention has a full-length sequence as depicted in or corresponding to the sequences of the present invention.

Various modifications for example of the 5' and 3' UTR are also contemplated by the invention.

In another embodiment, the nucleic acid further comprises a reporter gene, which, in one embodiment, is a gene encoding neomycin phosphotransferase, Renilla luciferase, secreted alkaline phosphatase (SEAP), Gaussia luciferase or fluorescent proteins such as green or red fluorescent protein.

Naturally, as noted above, the HCV nucleic acid sequence of the invention is selected from the group consisting of double stranded DNA, positive-sense cDNA, or negative-sense cDNA, or positive-sense RNA or negative-sense RNA or double stranded RNA.

Thus, where particular sequences of nucleic acids of the invention are set forth, both DNA and corresponding RNA are intended, including positive and negative strands thereof.

In a further embodiment, the nucleic acid sequences or the nucleic acid sequences with any mutation described in this document is obtained by any other means than what is described above.

Nucleic acid molecules according to the present invention may be inserted in a plasmid vector for translation of the corresponding HCV RNA. Thus, the HCV DNA may comprise a promoter 5' of the 5'-UTR on positive-sense DNA, whereby transcription of template DNA from the promoter produces replication-competent RNA. The promoter can be selected from the group consisting of a eukaryotic promoter, yeast promoter, plant promoter, bacterial promoter, or viral promoter.

Thus, in one embodiment the present invention provides a cassette vector for cloning viral genomes, comprising, inserted therein, the nucleic acid sequence according to the invention and having an active promoter upstream thereof.

Adapted mutants of a HCV-cDNA construct or HCV-RNA full-length genome with improved abilities to generate infectious viral particles in cell culture compared to the original HCV-cDNA construct or the original HCV-RNA full-length genome are characterized in that they are obtainable by a method in which the type and number of mutations in a cell culture adapted HCV-RNA genome are determined through sequence analysis and sequence comparison and these mutations are introduced into a HCV-cDNA construct, particularly a HCV-cDNA construct according to the present invention, or into an (isolated) HCV-DNA full-length genome, either by site-directed mutagenesis, or by exchange of DNA fragments containing the relevant mutations.

The present inventors here report adaptive mutations, which allow efficient formation and release of viral particles in cell culture, and thus the present invention relates to these adaptive mutations in the present use as well as use in other strains by changing equivalent positions of such genomes to the adapted nucleotide or amino acid described.

A group of preferred HCV-cDNA constructs, HCV-RNA full-length genomes with the ability to release viral particles in cell culture, which are consequently highly suitable for practical use, is characterized in that it contains one, several or all of the nucleic acid exchanges listed below and/or one or several or all of the following amino acid exchanges.

One embodiment of the present invention relates to adaptive mutations, wherein the adaptive mutation is a mutation that can be observed by clonal or direct sequencing of recovered replicating genomes of the sequences of the present invention.

Thus in a further embodiment, the present invention relates to nucleic acid molecules according to the present invention, wherein said molecule comprises one or more adaptive mutations in Core, E1, E2, p7, NS2, NS3, NS4A, NS4B, NS5A or NS5B singly or in combination.

In the context of the present invention the term "adaptive mutation" is meant to cover mutations identified in passaged viruses that provide the original and any other HCV sequence the ability to grow efficiently in culture. Furthermore all introductions of mutations into the sequences described, whether or not yielding better growth abilities, and the introduction of these mutations into any HCV sequence should be considered.

Thus the described mutations enable the HCV-RNA genome (e.g. derived from a HCV-cDNA clone) to form viral particles in and release these from suitable cell lines. In addition some of the described mutations might change the function of the concerned proteins in favourable ways, which might be exploited in other experimental systems employing these proteins.

This also includes other HCV genomes with adaptive mutations, all of them, combinations of them or individual mutations that grow in culture.

It should be understood that any feature and/or aspect discussed above in connection with the mutations according to the invention apply by analogy to both single mutations and any combination of the mutations.

In another embodiment all the amino acid changes observed herein are provided by the present application. The skilled addressee can easily obtain the same amino acid change by mutating another base of the codon and hence all means of obtaining the given amino acid sequence is intended.

Examples of such adaptive mutations are disclosed in the present examples.

Adaptive mutation T385P in E2 increased sensitivity to patient derived and well defined human monoclonal HCV neutralizing antibodies. Thus, T385P might expose conserved epitopes including a conserved HCV receptor binding site.

In brief, the present inventors have observed that T358P induced increased sensitivity to IgG purified from chronic phase patient serum, as well as to human monoclonal antibodies AR3A, which targets a conformational epitope that blocks the CD81 binding site on E2, and AR4A, which targets a conformational epitope in E1E2. Furthermore, the T385P mutation rendered the CD81 binding site on E2 more exposed as virus carrying this mutation was more sensitive to neutralization with soluble CD81 large-extracellular-loop.

Others have demonstrated that alanine substitution at position 385 of HCV pseudo particles carrying genotype 1a specific envelope glycoproteins increased sensitivity to neutralization by patient sera from chronically infected genotype 1-5 patients.

These can be favourable characteristics for a vaccine antigen, since a vaccine targeting conserved epitopes could be generated.

Thus, in one embodiment of the present inventiosn is the adaptive mutation T385P included.

To determine the efficiency of the developed system, HCV RNA titers are determined in IU/ml (international units/ml) with Taq-Man Real-Time-PCR and infectious titers are determined with a focus forming unit assay.

The infectious titers are determined as TCID50/ml (median tissue culture infectious dose/ml) or FFU/ml (focus forming unites/ml); in such method, infectivity titers are determined by infection of cell culture replicates with serial dilutions of virus containing supernatants and, following immuno-stainings for HCV antigens, counting of HCV-antigen positive cell foci.

HCV RNA titers and infectivity titers can be determined extracellularly, in cell culture supernatant (given as IU and TCID50 or FFU per ml, respectively) or intracellularly, in lysates of pelleted cells (given as IU and TCID50 or FFU related to a the given cell number or culture plate wells, which was lysed).

One embodiment of the present invention relates to a nucleic acid molecule of the present invention, wherein said molecule is capable of generating a HCV RNA titer of $10^4$ IU/ml or above following transfection and/or subsequent viral passage, such as a titer of at least $10^5$ IU/mL, such as a titer of at least $10^6$ IU/mL, such as a titer of at least $10^7$ IU/mL, such as a titer of at least $10^8$ IU/mL, such as a titer of at least $10^9$ IU/mL, such as a titer of at least $10^{10}$ IU/mL, such as a titer of at least $10^{11}$ IU/mL, or such as a titer of at least $10^{12}$ IU/mL.

In another embodiment, the present invention relates to a nucleic acid molecule according to the invention, wherein said molecule is capable of generating a HCV infectivity titer of at least $10^2$ TCID50/ml or above following transfection and/or subsequent viral passage, such as a titer of at least $10^3$ TCID50/ml, such as a titer of at least $10^4$ TCID50/ml, such as a titer of at least $10^5$ TCID50/ml, such as a titer of at least $10^6$ TCID50/ml, such as a titer of at least $10^7$ TCID50/ml, such as a titer of at least $10^8$ TCID50/ml, such as a titer of at least $10^9$ TCID50/ml or such as a titer of at least $10^{10}$ TCID50/ml.

In another embodiment, the present invention relates to a nucleic acid molecule according to the invention, wherein said molecule is capable of generating an HCV infectivity titer of at least $10^2$ FFU/ml or above following transfection and/or subsequent viral passage, such as a titer of at least $10^3$ FFU/ml, such as a titer of at least $10^4$ FFU/ml, such as a titer of at least $10^5$ FFU/ml, such as a titer of at least $10^6$ FFU/ml, such as a titer of at least $10^7$ FFU/ml, such as a titer of at least $10^8$ FFU/ml, such as a titer of at least $10^9$ FFU/ml or such as a titer of at least $10^{10}$ FFU/ml.

It is of course evident to the skilled addressee that the titers described here are obtained using the assay described in this text. Any similar or equivalent titer determined by any method is thus evidently within the scope of the present invention.

One embodiment of the present invention relates to a composition comprising a nucleic acid molecule according to the invention suspended in a suitable amount of a pharmaceutical acceptable diluent or excipient.

In another embodiment, this invention provides for compositions comprising an isolated nucleic acid, vector or cell of this invention, or an isolated nucleic acid obtained via the methods of this invention.

In one embodiment, the term "composition" refers to any such composition suitable for administration to a subject, and such compositions may comprise a pharmaceutically acceptable carrier or diluent, for any of the indications or modes of administration as described. The active materials in the compositions of this invention can be administered by any appropriate route, for example, orally, parenterally, intravenously, intradermally, subcutaneously, or topically, in liquid or solid form.

It is to be understood that any applicable drug delivery system may be used with the compositions and/or agents/vectors/cells/nucleic acids of this invention, for administration to a subject, and is to be considered as part of this invention.

The compositions of the invention can be administered as conventional HCV therapeutics. The compositions of the invention may include more than one active ingredient which interrupts or otherwise alters groove formation, or occupancy by RNA or other cellular host factors, in one embodiment, or replicase components, in another embodiment, or zinc incorporation, in another embodiment.

The precise formulations and modes of administration of the compositions of the invention will depend on the nature of the anti-HCV agent, the condition of the subject, and the judgment of the practitioner. Design of such administration and formulation is routine optimization generally carried out without difficulty by the practitioner.

It is to be understood that any of the methods of this invention, whereby a nucleic acid, vector or cell of this invention is used, may also employ a composition comprising the same as herein described, and is to be considered as part of this invention.

"Pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopoeia or other generally recognized pharmacopoeia for use in animals, and more particularly in humans.

The term "excipient" refers to a diluent, adjuvant, carrier, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The term "adjuvant" refers to a compound or mixture that enhances the immune response to an antigen. An adjuvant can serve as a tissue depot that slowly releases the antigen and also as a lymphoid system activator that non-specifically enhances the immune response. Often, a primary challenge with an antigen alone, in the absence of an adjuvant, will fail to elicit a humoral or cellular immune response.

Adjuvants include, but are not limited to, complete Freund's adjuvant, incomplete Freund's adjuvant, saponin, mineral gels such as aluminum hydroxide, surface active substances such as lysolecithin, pluronicpolyols, polyanions, peptides, oil or hydrocarbon emulsions, keyhole limpet hemocyanins, dinitrophenol, and potentially useful human adjuvants such as BCG (bacilleCalmette-Guerin), Corynebacteriumparvmm, aluminum hydroxide+MPL, Addavax, MF59, CAF01, CAF04, CAF05 and CAF09, Toll-like receptor agonists such as, but not limited to poly:IC, and Sigma adjuvant system.

Preferably, the adjuvant is pharmaceutically acceptable.

Thus relates one embodiment of the present invention to a composition comprising a nucleic acid molecule according to the present invention suspended in a suitable amount of a pharmaceutical acceptable diluent or excipient.

The nucleotides of the present invention may be used to provide a method for identifying additional cell lines that are permissive for infection with HCV, comprising contacting (e.g. transfecting) a cell line in tissue culture with an infectious amount of HCV RNA of the present invention, e.g., as produced from the plasmid clones, and detecting replication and formation and release of viral particles of HCV in cells of the cell line.

Naturally, the invention extends as well to a method for identifying an animal that is permissive for infection with HCV, comprising introducing an infectious amount of the HCV RNA, e.g., as produced by the plasmids, to the animal, and detecting replication and formation and release of viral particles of HCV in the animal. By providing infectious HCV, e.g. comprising a dominant selectable marker, the invention further provides a method for selecting for HCV with further adaptive mutations that permit higher levels of HCV replication in a permissive cell line or animal comprising contacting (e.g. transfecting) a cell line in culture, or introducing into an animal, an infectious amount of the HCV RNA, and detecting progressively increasing levels of HCV RNA and infectious HCV viral particles in the cell line or the animal.

In a specific embodiment, the adaptive mutation permits modification of HCV tropism. An immediate implication of this aspect of the invention is creation of new valid cell culture and animal models for HCV infection.

The permissive cell lines or animals that are identified using the nucleic acids of the invention are very useful, inter alia, for studying the natural history of HCV infection, isolating functional components of HCV, and for sensitive, fast diagnostic applications, in addition to producing authentic HCV virus or components thereof.

Because the HCV DNA, e.g., plasmid vectors, of the invention encode HCV components, expression of such vectors in a host cell line transfected, transformed, or transduced with the HCV DNA can be effected.

For example, a baculovirus or plant expression system can be used to express HCV virus particles or components thereof. Thus, a host cell line may be selected from the group consisting of a bacterial cell, a yeast cell, a plant cell, an insect cell, and a mammalian cell.

In one embodiment, the cell is a hepatocyte, or in another embodiment, the cell is the Huh-7 hepatoma cell line or a derived cell line such as Huh7.5, Huh7.5.1 cell line.

In one embodiment, the cell, or in another embodiment, cell systems of this invention comprise primary cultures or other, also non hepatic cell lines. "Primary cultures" refers, in one embodiment, to a culture of cells that is directly derived from cells or tissues from an individual, as well as cells derived by passage from these cells, or immortalized cells.

In one embodiment, "cell line" refers to a population of cells capable of continuous or prolonged growth and division in vitro. The term "cell lines" also includes immortalized cells. Often, cell lines are clonal populations derived from a single progenitor cell. Such cell lines are also termed "cell clones". It is further known in the art that spontaneous or induced changes can occur in karyotype during storage or transfer of such clonal populations. Therefore, cells derived from the cell clones referred to may not be precisely identical to the ancestral cells or cultures. According to the present invention, such cell clones may be capable of supporting replication of a vector, virus, viral particle, etc., of this invention, without a significant decrease in their growth properties, and are to be considered as part of this invention.

It is to be understood that any cell of any organism that is susceptible to infection by or propagation of an HCV construct, virus or viral particle of this invention is to be considered as part of this invention, and may be used in any method of this invention, such as for screening or other assays, as described herein.

Thus relates one embodiment of the present invention to a cell comprising the nucleic acid according to the present invention, the composition of present invention or the cassette vector of the present invention.

Another embodiment of the present invention relates to a method for producing a cell, which replicates human hepatitis C virus and produces a virus particle comprising introducing a nucleic acid molecule of the present invention into a cell.

In a preferred embodiment is the cell is a Huh7.5 cell.

Another embodiment of the present invention relates to a cell obtainable by the methods of the present invention.

Also, a method for in vitro producing a hepatitis C virus-infected cell comprising culturing the cell which produces virus particles of the present invention and infecting other cells with the produced virus particle in the culture.

Naturally, the invention extends to any cell obtainable by such methods, for example any in vitro cell line infected with HCV, wherein the HCV has a genomic RNA sequence as described herein such as a hepatitis C virus infected cell obtainable by any of the methods described.

In one embodiment, the cell line is a hepatocyte cell line such as Huh7 or derived cell lines e.g. Huh7.5 or Huh7.5.1.

In another embodiment the cell is Huh7.5.

In another embodiment the cell is any cell expressing the genes necessary for HCV infection and replication, such as but not limited to CD81, SR-BI, Claudin-1, -4, -6 or -9, occludin, and the low-density lipoprotein receptor.

The invention further provides various methods for producing HCV virus particles, including by isolating HCV virus particles from the HCV-infected non-human animal of invention; culturing a cell line of the invention under conditions that permit HCV replication and virus particle formation; or culturing a host expression cell line transfected with HCV DNA under conditions that permit expression of HCV particle proteins; and isolating HCV particles or particle proteins from the cell culture. The present invention extends to an HCV virus particle comprising a replication-competent HCV genome RNA, or a replication-defective HCV genome RNA, corresponding to an HCV nucleic acid of the invention as well.

The production of authentic virus proteins (antigens) may be used for the development and/or evaluation of diagnostics. The cell culture system according to the invention also allows the expression of HCV antigens in cell cultures. In principle these antigens can be used as the basis for diagnostic detection methods.

The production of HCV viruses and virus-like particles, in particular for the development or production of therapeutics and vaccines as well as for diagnostic purposes is an embodiment of the present invention. Especially cell culture adapted complete HCV genomes, which could be produced by using the cell culture system according to the invention, are able to replicate and form viral particles in cell culture with high efficiency. These genomes have the complete functions of HCV and in consequence they are able to produce infectious viruses.

Thus in one embodiment the present invention relates to a method for producing a hepatitis C virus particle of the present invention or parts thereof, comprising culturing a cell or an animal to allow either to produce the virus.

In another embodiment the inventions provides a hepatitis C virus particle obtainable by the method described.

Because the invention provides, inter alia, infectious HCV RNA, the invention provides a method for infecting an animal with HCV, which comprises administering an infectious dose of HCV RNA, such as the HCV RNA transcribed from the plasmids described above, to the animal. Naturally, the invention provides a non-human animal infected with HCV of the invention, which non-human animal can be prepared by the foregoing methods.

In one embodiment the introduced mutations attenuates the virus in vivo.

A further advantage of the present invention is that, by providing a complete functional HCV genome, authentic HCV viral particles or components thereof, which may be produced with native HCV proteins or RNA in a way that is not possible in subunit expression systems, can be prepared.

In addition, since each component of HCV of the invention is functional (thus yielding the authentic HCV), any specific HCV component is an authentic component, i.e., lacking any errors that may, at least in part, affect the clones of the prior art. Indeed, a further advantage of the invention is the ability to generate HCV virus particles or virus particle proteins that are structurally identical to or closely related to natural HCV virions or proteins. Thus, in a further embodiment, the invention provides a method for propagating HCV in vitro comprising culturing a cell line contacted with an infectious amount of HCV RNA of the invention, e.g., HCV RNA translated from the plasmids described above, under conditions that permit replication of the HCV RNA.

In one embodiment, the method further comprises isolating infectious HCV. In another embodiment, the method further comprises freezing aliquots of said infectious HCV. According to this aspect of the invention, and in one embodiment, the HCV is infectious following thawing of said aliquots, and in another embodiment, the HCV is infectious following repeated freeze-thaw cycles of said aliquots.

A further embodiment of the present invention relates to a method for in vitro producing a hepatitis C virus-infected cell comprising culturing a cell according to the present invention and infecting other cells with the produced virus particle in the culture.

Screening for Anti-Viral Drugs and the Determination of Drug Resistance

It can be assumed that resistance to therapy occurs due to the high mutation rate of the HCV genome. This resistance, which is very important for the clinical approval of a substance, can be detected with the cell culture system according to the invention. Cell lines, in which the HCV-RNA construct or the HCV genome or subgenome replicates and produces infectious viral particles, are incubated with increasing concentrations of the relevant substance and the replication of the viral RNA is either determined by means of an introduced reporter gene or through the qualitative or quantitative detection of the viral nucleic acids or proteins. The release of viral particles is determined by measuring HCV RNA and infectivity titers in the cell culture supernatant. Alternatively, the number of antigen-expressing cells is determined. Resistance is given if no or a reduced inhibition of the replication and release of viral particles can be observed with the normal concentration of the active substance. The nucleotide and amino acid replacements responsible for the therapy resistance can be determined by recloning the HCV-RNA (for example by the means of RT-PCR) and sequence analysis. By cloning the relevant replacement(s) into the original construct its causality for the resistance to therapy can be proven.

While the replicon systems facilitated testing of drugs interfering with replication such as NS3/4A protease and polymerase inhibitors, the variant genomes obtained in the present invention may prove useful for different research topics.

The systems developed in this invention are ideal candidates for specific testing of therapeutics in general and therapeutics targeting viral entry, assembly and release.

Genomes with the sequences of the present invention are valuable for testing of neutralizing antibodies and other drugs acting on entry level, such as fusion inhibitors.

In one embodiment the present invention relates to a method for identifying neutralizing antibodies.

In another one embodiment the present invention relates to a method for identifying cross-genotype neutralizing antibodies.

In one embodiment the present invention relates to a method of raising neutralizing antibodies.

In another embodiment the present invention relates to a method of raising cross neutralizing antibodies.

In one embodiment the present invention related to a method for screening new HCV genotype 5a inhibitors or neutralizing antibodies, comprising a) culturing at least one selected from the group consisting of a cell according to the present invention, a hepatitis C virus infected cell according to the present invention and a hepatitis C virus particle obtainable by the present invention together with a hepatitis C virus permissive cell, and b) subjecting said virus or virus infected cell culture to a blood sample or derivatives thereof from a HCV genotype 5a infected patient c) detecting the amount of replicating RNA and/or the virus particles.

Inhibitors targeting the HCV non-structural proteins NS3/4A, NS5A and NS5B are currently being developed. The first directly-acting antiviral compounds targeting the NS3/4A protease were licensed in 2011 (Telaprevir and Boceprevir). Clinical studies show promising results for inhibitors of NS5A and the NS5B polymerase. The present invention offers novel culture systems where additional HCV isolates can be tested to generate efficient cross-reactive inhibitors.

The p7 peptide features two transmembrane domains (TM1 and TM2), and p7 monomers multimerize to form a putative ion channel. Additionally p7 has been shown to contain genotype specific sequences required for genotype specific interactions between p7 and other HCV proteins. Hence, new compounds targeting the putative p7 ion-channel and autoprotease inhibitors interfering with NS2, and drugs targeting cellular proteins involved in the described processes can be tested.

Thus, one embodiment of the present invention relates to a method for screening an anti-hepatitis C virus substance, comprising
 a) culturing at least one selected from the group consisting of a cell according to the present invention, a hepatitis C virus infected cell according to the present invention and a hepatitis C virus particle obtainable by the present invention together with a hepatitis C virus permissive cell,
 b) subjecting said virus or virus infected cell culture to the anti-hepatitis C virus substance, and
 c) detecting the replicating RNA and/or the virus particles in the resulting culture.

Another embodiment of the present invention relates to a method for screening an anti-hepatitis C virus substance, comprising
 a) culturing at least one selected from the group consisting of a cell according to the present invention and the hepatitis C virus particle according to the present invention together with a hepatitis C virus permissive cell, and
 b) detecting the replicating RNA or the virus particles in the resulting culture.

Yet another embodiment of the present invention relates to a hepatitis C vaccine comprising a hepatitis C virus particle of the present invention or a part thereof.

In another embodiment, the inhibition of HCV replication and/or infection and/or pathogenesis includes inhibition of downstream effects of HCV. In one embodiment, downstream effects include neoplastic disease, including, in one embodiment, the development of hepatocellular carcinoma.

In one embodiment, the invention provides a method of screening for anti-HCV therapeutics, the method comprising contacting a cell with an isolated nucleic acid molecule encoding an infectious recombinant HCV genome, comprising a chimeric HCV genome and contacting the cell with a candidate molecule, independently contacting the cell with a placebo and determining the effects of the candidate molecule on HCV infection, replication, or cell-to-cell spread, versus the effects of the placebo, wherein a decrease in the level of HCV infection, replication, or cell-to-cell spread indicates the candidate molecule is an anti-HCV therapeutic.

In one embodiment, the method may be conducted be in vitro or in vivo. In one embodiment, the cells as described may be in an animal model, or a human subject, entered in a clinical trial to evaluate the efficacy of a candidate molecule. In one embodiment, the molecule is labelled for easier detection, including radio-labelled, antibody labelled for fluorescently labelled molecules, which may be detected by any means well known to one skilled in the art.

In one embodiment, the candidate molecule is an antibody.

Another embodiment of the present invention relates to an antibody against the hepatitis C virus particle of the present invention.

In one embodiment, the term "antibody" refers to intact molecules as well as functional fragments thereof, such as Fab, F(ab')2, and Fv. In one embodiment, the term "Fab" refers to a fragment, which contains a monovalent antigen-binding fragment of an antibody molecule, and in one embodiment, can be produced by digestion of whole antibody with the enzyme papain to yield an intact light chain and a portion of one heavy chain, or in another embodiment can be obtained by treating whole antibody with pepsin, followed by reduction, to yield an intact light chain and a portion of the heavy chain. In one embodiment, the term "F(ab')2", refers to the fragment of the antibody that can be obtained by treating whole antibody with the enzyme pepsin without subsequent reduction, F(ab')2 is a dimer of two Fab' fragments held together by two disulfide bonds. In another embodiment, the term "Fv" refers to a genetically engineered fragment containing the variable region of the light chain and the variable region of the heavy chain expressed as two chains, and in another embodiment, the term "single chain antibody" or "SCA" refers to a genetically engineered molecule containing the variable region of the light chain and the variable region of the heavy chain, linked by a suitable polypeptide linker as a genetically fused single chain molecule.

Methods of producing these fragments are known in the art.

In another embodiment, the candidate molecule is a small molecule. In one embodiment, the phrase "small molecule" refers to, inter-alia, synthetic organic structures typical of pharmaceuticals, peptides, nucleic acids, peptide nucleic acids, carbohydrates, lipids, and others, as will be appreciated by one skilled in the art. In another embodiment, small molecules, may refer to chemically synthesized peptidomimetics of the 6-mer to 9-mer peptides of the invention.

In another embodiment, the candidate molecule is a nucleic acid. Numerous nucleic acid molecules can be envisioned for use in such applications, including antisense, siRNA, ribozymes, etc., as will be appreciated by one skilled in the art.

It is to be understood that the candidate molecule identified and/or evaluated by the methods of this invention, may be any compound, including, inter-alia, a crystal, protein, peptide or nucleic acid, and may comprise an HCV viral product or derivative thereof, of a cellular product or derivative thereof. The candidate molecule in other embodiments may be isolated, generated synthetically, obtained via translation of sequences subjected to any mutagenesis technique, or obtained via protein evolution techniques, well known to those skilled in the art, each of which represents an embodiment of this invention, and may be used in the methods of this invention, as well.

In one embodiment, the compound identified in the screening methods as described, may be identified by computer modelling techniques, and others, as described herein. Verification of the activity of these compounds may be accomplished by the methods described herein, where, in one embodiment, the test compound demonstrably affects HCV infection, replication and/or pathogenesis in an assay, as described. In one embodiment, the assay is a cell-based assay, which, in one embodiment, makes use of primary isolates, or in another embodiment, cell lines, etc. In one embodiment, the cell is within a homogenate, or in another embodiment, a tissue slice, or in another embodiment, an organ culture. In one embodiment, the cell or tissue is hepatic in origin, or is a derivative thereof. In another embodiment, the cell is a commonly used mammalian cell line, which has been engineered to express key molecules known to be, or in another embodiment, thought to be involved in HCV infection, replication and/or pathogenesis.

In another embodiment, protein, or in another embodiment, peptide or in another embodiment, other inhibitors of the present invention cause inhibition of infection, replication, or pathogenesis of HCV in vitro or, in another embodiment, in vivo when introduced into a host cell containing the virus, and may exhibit, in another embodiment, an IC50 in the range of from about 0.0001 nM to 100 µM in an in vitro assay for at least one step in infection, replication, or pathogenesis of HCV, more preferably from about 0.0001 nM to 75 µM, more preferably from about 0.0001 nM to 50 µM, more preferably from about 0.0001 nM to 25 µM, more preferably from about 0.0001 nM to 10 µM, and even more preferably from about 0.0001 nM to 1 µM.

In another embodiment, the inhibitors of HCV infection, or in another embodiment, replication, or in another embodiment, pathogenesis, may be used, in another embodiment, in ex vivo scenarios, such as, for example, in routine treatment of blood products wherein a possibility of HCV infection exists, when serology shows a lack of HCV infection.

In another embodiment, the anti-HCV therapeutic compounds identified via any of the methods of the present invention can be further characterized using secondary screens in cell cultures and/or susceptible animal models. In one embodiment, a small animal model may be used, such as, for example, a tree shrew Tupaiabelangerichinensis. In another embodiment, an animal model may make use of a chimpanzee. Test animals may be treated with the candidate compounds that produced the strongest inhibitory effects in any of the assays/methods of this invention. In another embodiment, the animal models provide a platform for pharmacokinetic and toxicology studies.

The construct according to the invention by itself can also be used for various purposes in all its embodiments. This includes the construction of hepatitis C viruses or HCV-like particles and their production in cell cultures as described.

These HCV or HCV-like particles can be used in particular as vaccine. Thus, one embodiment of the present invention relates to a hepatitis C vaccine comprising a hepatitis C virus particle according to the invention or a part thereof.

In another embodiment, the nucleic acids, vectors, viruses, or viral particles may be further engineered to express a heterologous protein, which, in another embodiment, is mammalian or a derivative thereof, which is useful in combating HCV infection or disease progression. Such proteins may comprise cytokines, growth factors, tumor suppressors, or in one embodiment, may following infection, be expressed predominantly or exclusively on an infected cell surface. According to this aspect of the invention, and in one embodiment, such molecules may include costimulatory molecules, which may serve to enhance immune response to infected cells, or preneoplastic cells, or neoplastic cells, which may have become preneoplastic or neoplastic as a result of HCV infection. In one embodiment, the heterologous sequence encoded in the nucleic acids, vectors, viruses, or viral particles of this invention may be involved in enhanced uptake of a nucleic acids, vectors, viruses, or viral particles, and may specifically target receptors thought to mediate HCV infection.

Further, the present invention relates to a method for producing a hepatitis C virus vaccine comprising using a hepatitis C virus particle according to the invention as an antigen, and naturally any antibody against such hepatitis C virus particle.

The cell culture system developed of the present invention will be a valuable tool to address different research topics.

It will allow the isolate, subtype and genotype specific study of functions of all HCV genome regions and proteins using reverse genetics.

Accordingly the developed cell culture systems allow individual patient targeting. This means that when a new potential therapeutic candidate is discovered it is possible to test this particular candidate or combination of candidates on novel HCV isolates grown in culture.

Knowing which specific genotype the candidate is functioning towards, it allows an individual treatment of each patient dependent on which specific genotype the patient is infected with. Furthermore these cell culture systems allow the development of antibodies and vaccines targeting individual patients.

The replication level of a virus can be determined, in other embodiments, using techniques known in the art, and in other embodiments, as exemplified herein. For example, the genome level can be determined using RT-PCR, and northern blot. To determine the level of a viral protein, one can use techniques including ELISA, immunoprecipitation, immunofluorescence, EIA, RIA, and Western blotting analysis.

In one embodiment, the invention provides a method of identifying sequences in HCV associated with HCV pathogenicity, comprising contacting cells with an isolated nucleic acid molecule encoding an infectious recombinant HCV genome, comprising a chimeric HCV genome, contacting cells with an isolated nucleic acid molecule comprising at least one mutation of the chimeric HCV genome, independently culturing the cells and determining HCV infection, replication, or cell-to-cell spread, in cells contacted with the mutant, versus the chimeric HCV, whereby changes in HCV infection, replication, or cell-to-cell spread in cells contacted with the mutant virus shows the mutation is in an HCV sequence associated with HCV pathogenicity.

In one embodiment, the invention provides a method of identifying HCV variants with improved growth in cell culture, the method comprising contacting cells with an isolated nucleic acid molecule encoding an infectious recombinant HCV genome, comprising a chimeric HCV genome contacting cells with an isolated nucleic acid molecule comprising at least one mutation of the chimeric HCV genome, independently culturing the cells and determining HCV infection, replication, or cell-to-cell spread, in cells contacted with the chimeric HCV or the mutated virus, whereby enhanced HCV infection, replication, or cell-to-cell spread in cells contacted with the mutated virus shows that the HCV variant has improved growth in cell culture.

In some embodiments, HCV variants are selected for enhanced replication, over a long course of time, in vitro culture systems. According to this aspect of the invention, and in some embodiments, cells contacted with the variants are characterized by reduced infection, as compared to cells contacted with the chimeric HCV.

Kits

In a related aspect, the invention also provides a test kit for HCV comprising HCV virus components, and a diagnostic test kit for HCV comprising components derived from an HCV virus as described herein.

Furthermore the invention also provides test kits, for screening for new HCV inhibitors, neutralizing and cross neutralizing antibodies, comprising HCV virus components.

A further aspect of the present invention relates to a method for obtaining an isolated nucleic acid molecule encoding a human hepatitis C virus with adaptive mutations, comprising identification of one or more adaptive mutations as described in the above method, incorporation of said one or more adaptive mutations into a nucleic acid molecule encoding a full length human hepatitis C virus, and isolating the nucleic acid molecule encoding a human hepatitis C virus with adaptive mutations.

One embodiment of the present invention relates to an isolated nucleic acid molecule obtained from the above method.

Another embodiment of the present invention relates to an isolated nucleic acid molecule according to the present invention, wherein the human hepatitis C virus is of genotype 5a.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples and figure.

EXAMPLES

Example 1—Production of High-Titer Serum-Free Cell Culture Grown HCV Particles of Genotype 1-6

Materials and Methods

Huh7.5 Cell Culture and Infection with HCV Recombinants.

Human hepatoma Huh7.5 cells were cultured in culture flasks (Nunc) in DMEM (Gibco/Invitrogen) supplemented with 10% fetal bovine serum (FBS, [Sigma]), penicillin 100 U/mL and streptomycin 100 μg/mL (Gibco/Invitrogen), referred to as DMEM+10% FBS. Cells were kept subconfluent and split every 2-3 days. For splitting, cells were washed in PBS (Invitrogen) and detached using trypsin (Sigma-Aldrich). For serum-free cultures, cells were plated in DMEM+10% FBS. When cells were 80% confluent, DMEM+10% FBS was removed, cells were washed in PBS and adenovirus expression medium (AEM, [Gibco/Invitrogen]) supplemented with penicillin 100 U/mL and streptomycin 100 μg/mL, referred to as AEM, was added without splitting the cells. Every 2-3 days, supernatant was removed and fresh AEM was added to the cells. Huh7.5 cell cultures were maintained at 37° C. and 5% $CO_2$.

Generation of HCVcc Virus Stocks.

For generation of HCVcc and sf-HCVcc virus stocks, Huh7.5 cells cultured in DMEM+10% FBS at 80% confluency were infected at a multiplicity of infection (MOI) of 0.003 using 1st or 2nd viral passage stocks of the following HCVcc intra- and intergenotypic recombinants: H77C/JFH1V787A,Q1247L (referred to as H77(1a)), J4/JFH1F886L,Q1496L (J4(1b)), J6/JFH1 (J6(2a)), S52/JFH1I787S,K1398Q (S52(3a)), ED43/JFH1T827A,T977S (ED43(4a)), SA13/JFH1A1022G,K1119R (SA13(5a)), and HK6a/JFH1F350S,N417T (HK6a(6a)). The % infection was monitored by HCV-specific immunostaining as described below. For generation of HCVcc virus stocks, cells were maintained in DMEM+10% FBS; supernatants were harvested every 2-3 days, when cells were split, until % of infected cells declined, as detected by immunostaining. High-titer stocks, collected at the peak of viral infection, were used for further experiments. Stocks with relatively low peak titers were concentrated using Amicon 100 kDa centrifugation filters (Millipore). For generation of sf-HCVcc virus stocks, DMEM+10% FBS cell cultures with 40-80% HCV infected cells were washed with PBS and AEM was added. Cells were maintained in AEM, and supernatants were harvested every 2-3 days, when AEM was exchanged, for up to 29 days. Supernatants were sterile filtered and stored at −80° C. The HCV Core-E2 sequences of all virus stocks used for further experiments were determined by direct sequencing (described below). Sequences were identical to the plasmid sequence unless otherwise indicated in respective figure and table legends.

Evaluation of HCV Infected Cell Cultures.

Spread of HCV recombinants in cell cultures was monitored by HCV NS5A immunostaining. Cells plated onto chamber slides (Nunc) the previous day were fixed for 10 minutes in ice-cold acetone (Sigma-Aldrich) and washed twice with PBS and twice with PBS+0.1% Tween-20 (Sigma-Aldrich). Cells were stained for HCV NS5A using primary anti-NS5A antibody 9E10 at 1:1,000 dilution in PBS+1% bovine serum albumin (BSA, [Roche Applied Science])+0.2% skim milk (PBS/BSK) for two hours at room temperature. Cells were washed twice with PBS and twice with PBS+0.1% Tween-20, and stained using secondary antibody Alexa Fluor 594-conjugated goat anti-mouse IgG (H+L) (Invitrogen) at 1:500 dilution and Hoechst 33342 (Invitrogen) at 1:1,000 dilution in PBS+0.1% Tween-20. Cells were washed twice in PBS, before being covered by Fluoromount-G (SouthernBiotech) and a cover-slip.

Culture supernatant infectivity titers were determined as Focus Forming Units (FFU)/mL. Huh7.5 cells, plated at 6,000 cells/well onto poly-D-lysine coated 96-well plates (Nunc) the day before, were infected with serially-diluted supernatants (lowest dilution 1:2). Forty-eight hours after infection, cells were fixed in ice-cold methanol and washed twice with PBS+B0.1% Tween-20 before being incubated with 3% H2O2 for five minutes at room temperature. Cells were washed twice with PBS+0.1% Tween-20 and HCV NS5A was immunostained with primary anti-NS5A antibody 9E10 at 1:1,000 dilution in PBS/BSK at 4° C. The next day, cells were washed twice with PBS+0.1% Tween-20 and stained using secondary antibody ECL anti-mouse IgG horseradish peroxidase (HRP)-linked whole antibody (GE Healthcare Amersham) at 1:300 in PBS+0.1% Tween-20 for 30 minutes at room temperature before being visualized by 30 minutes incubation at room temperature with a DAB substrate kit (Dako). FFU were counted automatically using an ImmunoSpot series 5 UV analyzer (CTL Europe GmbH) with customized software as described previously. Lower limit of detection was calculated for each 96-well plate as the mean of at least 6 negative wells plus 3 standard deviations plus 3. Upper limit of detection was set to 200 FFU/well as this was within the linear range of test dilution series and comparable with manual determinations.

For determination of HCV RNA titers in culture supernatant, RNA was extracted from 200 μL supernatant using the Total Nucleic Acid Isolation Kit (Roche Applied Science); titers were determined by TaqMan real-time PCR as previously described . HCV Core titers in culture supernatant were determined using the ARCHITECT HCV Ag assay (Abbott).

Direct Sequencing of Cell Culture-Derived HCV.

HCV RNA was purified from 200 μL cell culture supernatant using the High Pure Viral Nucleic Acid Kit (Roche Applied Science). Overall, reverse transcription, 1st round PCR and 2nd round nested PCR were carried out as previously described. Primers used to generate cDNA and PCR amplicons spanning the Core-E2 region have been previously reported for H77(1a) and ED43(4a); J4(1b) and HK6a (6a), J6(2a) and S52(3a); as well as SA13(5a). Direct sequencing of amplicons was carried out by Macrogen Europe.

Single-Cycle Virus Production Assay in S29 Cells.

Overall, S29 cell experiments were carried out as previously described. Briefly, 400,000 CD81-deficient S29 cells were plated in 6-well plates 24 hours before transfection. In vitro HCV RNA transcripts of SA13(5a) as well as of positive control (J6(2a)) and of negative control (J6(2a)-GND) were generated using T7 RNA polymerase (Promega) for 2 hours at 37° C., DNAse treated using DNA RQ1 DNAse (Promega) and purified using RNeasy kit (Qiagen). HCV RNA transcripts (2.5 µg) were mixed with 5 µL Lipofectamine 2000 (Invitrogen) in 500 µL serum-free Opti-MEM (Gibco/Invitrogen). S29 cells were incubated with transfection complexes for 4 hours in Opti-MEM. Following transfection, Opti-MEM was replaced by either DMEM+10% FBS or AEM. S29 cells were collected at 4, 24, 48 and 72 hours post transfection and prepared for determination of intracellular HCV Core and infectivity titers as previously described. Culture supernatants were collected at 24, 48 and 72 hours post transfection for determination of extracellular HCV Core and infectivity titers. Infectivity titers were determined as described above, while Core titers were determined using the ARCHITECT HCV Ag assay (Abbott).

Equilibrium Density Gradient Ultracentrifugation.

Semi-continuous 10-40% iodixanol gradients were prepared by layering 2.5 mL of 40%, 30%, 20% and 10% OptiPrep (iodixanol; Sigma-Aldrich) on top of each other as described previously. HCVcc containing supernatants were either loaded directly on top of the gradient, or concentrated using Amicon 100 kDa centrifugation filters before loading. A final volume of ~250 µL was loaded for all samples. The samples were ultracentrifuged at 151,000× relative centrifugal force (RCF) for 18 hours at 4° C. using a Beckman SW-41 rotor mounted in a Beckman XL-70 ultracentrifuge. After centrifugation, fractions of ~550 µL were collected from the bottom of the tube and 400 µL portions were weighed (model SI-114; Denver Instruments) to determine fraction densities. Fraction infectivity titers were determined as described above. Iodixanol containing fractions were diluted to contain ≤10% iodixanol before titration.

Receptor-, Endocytosis- and Neutralization Assays.

For receptor blocking assays we used Purified Mouse Anti-Human CD81 primary antibody (JS-81) and Purified Mouse IgG1K isotype control (MOPC-21) (both BD Biosciences); Purified Goat Anti-human LDLr polyclonal antibody (AF2148) and Normal Goat IgG control (AB108C) (both R&D Systems); Anti-SR-BI primary antibody (C16-71) and control antibody (D) were previously described. For HCVcc neutralization, we used chronic-phase serum from patient H taken 29 years after acute infection (H06) and chronic-phase serum from a genotype 5a infected patient (SA3) as well as a panel of monoclonal antibodies AR1B and AR2A-5A, which were previously described. For ApoE neutralization we used a mouse monoclonal primary antibody (1D7) blocking the ApoE receptor binding site, and mouse IgG1κ (1D1) control antibody previously described. For inhibition of clathrin-mediated endocytosis, we used chlorpromazine hydrochloride (Calbiochem). Huh7.5 cells were plated at 7,000 cells/well onto poly-D-lysine coated 96-well plates. On the following day, for receptor-blocking assays, antibodies were diluted in DMEM+10% FBS as specified and added to cells for 1 hour. For chlorpromazine assays, chlorpromazine was diluted in DMEM+10% FBS as specified and added to cells for 30 minutes. HCVcc was diluted in DMEM+10% FBS, whereas sf-HCVcc was diluted in AEM with FBS concentration adjusted to 10%. Virus dilutions were added to the cells incubated with blocking antibodies or chlorpromazine. Cell cultures were incubated for an additional 6 hours.

For HCV neutralization assays, chronic-phase HCV sera, or AR1B and AR2A-5A monoclonal antibodies were diluted in DMEM+10% FBS as specified and mixed with either HCVcc or sf-HCVcc diluted as for receptor blocking assays. Patient serum-virus or antibody-virus mixes were incubated for 1 hour, before being added to cells. Cell cultures were incubated for 6 hours. For ApoE neutralization, 1D7 and 1D1 monoclonal antibodies were diluted in DMEM+10% FBS as specified and mixed with either HCVcc or sf-HCVcc, diluted in DMEM+10% FBS. Antibody-virus mixes were incubated for 30 minutes, before being added onto cells. Cell cultures were incubated for 3 hours.

For blocking and neutralization assays, after 3 or 6 hours incubation as indicated above, the cells were washed in PBS and DMEM+10% FBS was added to all cultures. Cells were incubated and fixed 48 hours post infection in ice-cold methanol and HRP-stained for HCV S5A as described above. Single HCV NS5A positive cells were counted automatically using an ImmunoSpot series 5 UV analyzer (CTL Europe GmbH) with customized software as described previously. The % blocking and neutralization were calculated by relating counts of experimental wells to the mean count of six replicate wells with untreated control virus. For receptor blocking and neutralization assays, following logarithmic transformation of X-values, variable-slope sigmoidal dose-response curves [$Y = Bottom+(Top-Bottom)/(1+10^{(Log10EC50-X) \times HillSlope})$] were fitted to the data using GraphPad Prism 6.0. For receptor blocking and neutralization assays "Bottom" was constrained to "0". For neutralization assays, "Top" was constrained to "100", when appropriate, as indicated in Figure legends, and median inhibitory concentrations (IC50) were calculated using GraphPad Prism 6.0. For receptor blocking assays, maximum blocking rates (Bmax), the Y values at the top plateaus of the fitted curves, were calculated using GraphPad Prism 6.0.

HCV Immunoprecipitation Using Anti-ApoE Antibody.

Immunoprecipitation was done using the ApoE-specific antibody 1D7 and isotype-matched control antibody 1D1 as previously described. Briefly, 50 µl of magnetic-bead slurry was washed in antibody binding buffer (immunoprecipitation kit; Dynabeads Protein G; 100.070D; Invitrogen) and incubated it on a shaker with 5 µg antibody in 50 µl antibody binding buffer for 20 minutes at room temperature. The beads were subsequently washed two times in washing buffer and incubated with $10^6$ IU of the virus in 200 µl of complete medium on a shaker for 1 hour at room temperature. The beads were removed and washed three times in 200 µl of washing buffer prior to elution in 50 µl according to the manufacturer's instructions. HCV RNA was extracted from the complete eluate and measured in duplicates as previously described.

Cell Viability and Proliferation Assays.

For determination of Huh7.5 cell viability in DMEM+10% FBS versus AEM, we plated 6,000 cells per well of poly-D-lysine coated 96-well plates in DMEM+10% FBS. The following day, medium was removed and cells were incubated in DMEM+10% FBS or AEM for 48 hours. Then, cell viability was determined using the CellTiter 96® AQueous One Solution Cell Proliferation Assay kit (Promega) according to the manufacturer's instructions. The % viability was calculated by relating absorbance at 490 nm determined for 10 AEM cultures to the mean absorbance of 10 replicate DMEM+10% FBS cultures. For determination of chlorpromazine cytotoxicity, chlorpromazine was diluted in DMEM+10% FBS as specified and then added to 6,000 Huh 7.5 cells/well, plated the previous day in poly-D-lysine coated 96-well plates. Cells were incubated for 6 hours before chlorpromazine was removed and DMEM+10% FBS was added. Cell viability was determined 6 and 48 hours post-treatment using the CellTiter 96® AQueous One Solution Cell Proliferation Assay kit. The % viability was calculated by relating absorbance at 490 nm determined for chlorpromazine treated cultures to the mean absorbance of at least three replicate untreated cultures.

For determination of Huh7.5 cell proliferation in DMEM+10% FBS versus AEM, we used the BrdU cell proliferation kit (Millipore). Cells were plated in poly-d-lysine coated 96-well plates at 2,000 cells/well in DMEM+10% FBS according to the manufacturer's instructions. The following day, medium was removed and cells were incubated in DMEM+10% FBS or AEM for 48 hours. Then, cell proliferation was determined using the BrdU cell proliferation kit according to the manufacturer's instructions. The % proliferation was calculated by relating absorbance at 450 nm determined for 10 replicate AEM cultures to the mean absorbance of 10 replicate DMEM+10% FBS cultures.

Flow Cytometry.

For surface staining of HCV co-receptors we used Phycoerythrin (PE) Mouse Anti-Human CD81 primary antibody (BD Biosciences, JS-81), Anti-mouse LDL R-Phycoerythrin primary antibody (R&D systems, 263123), Purified Mouse Anti-Human CLA-1 (SR-BI) primary antibody (BD Transduction Laboratories, 25/CLA-1) with PE Goat Anti-Mouse Ig secondary antibody (BD Biosciences, polyclonal 550589) and Anti-human Claudin-1 primary antibody (R&D systems, 421203) with PE Goat Anti-Rat Ig secondary antibody (BD Biosciences, polyclonal 550767). Cells were detached by treatment with a 10 mM solution of EDTA in PBS for 10 minutes at 37° C. The cells were washed in PBS and resuspended in FACS buffer (PBS+1% FBS) and $2.5 \times 10^5$ cells/well were plated in a V-bottom 96-well plate. Cells were stained protected from light at 4° C. for 1 hour with either α-CD81 (25 µL/well according to the manufacturer's instructions), α-LDLr (10 µg/mL in FACS buffer), α-SR-BI (5 µg/mL in FACS buffer) or α-Claudin-1 (5 µg/mL in FACS buffer). Total volume in all wells was adjusted to 50 µL using FACS buffer. After incubation, cells were washed in FACS buffer. SR-BI- and claudin-1-stained cells were stained protected from light at 4° C. for 20 minutes with secondary antibodies α-mouse Ig (4 µg/mL in FACS buffer) or α-rat Ig (2 µg/mL in FACS buffer). Cells were washed in FACS buffer and fixed protected from light at room temperature for 15 minutes using CellFix (BD Biosciences). Cells were washed and resuspended in PBS before they were analyzed on a BD FACSCalibur flow cytometer using CellQuest Pro. Data analysis was done using FlowJo flow cytometry analysis software.

Results

Huh7.5 Cells Cultured in Serum-Free Medium Yield Higher HCV Infectivity Titers than Conventional Cultures.

To produce sf-HCVcc, HCV recombinants were cultured in Huh7.5 cells maintained in AEM, a commercially available cell culture medium without animal- or human serum as described in Materials and Methods. Because AEM cultured Huh7.5 cells did not tolerate detachment, AEM was replaced every 2-3 days without splitting the cells. Thus, animal-derived trypsin was not used during the virus production phase. Cultures handled in this manner became over-confluent but could be maintained for at least 29 days (data not shown).

We tested if AEM cultured cells supported production of sf-HCVcc. Huh7.5 cells cultured in DMEM+10% FBS were initially infected with JFH1-based Core-NS2 recombinants H77(1a), J4(1b), S52(3a) and ED43(4a)(FIG. 1). When viral infection had spread to ~80% of culture cells, as determined by immunostaining of HCV NS5A antigen, one replicate culture was maintained in AEM and another in DMEM+10% FBS. Similar to previous observations, HCVcc peak supernatant infectivity titers were 3.4 to 4.2 log 10 FFU/ml, followed by a drop in infectivity titers, when virus induced cell death was observed (FIG. 1). For sf-HCVcc, peak infectivity titers were higher than for HCVcc, reaching 4.6 to 5.0 log 10 FFU/ml (FIG. 1). Also, relatively high infectivity titers were maintained for a longer period for sf-HCVcc than for HCVcc.

We next aimed at producing sf-HCVcc virus stocks of prototype strains of the six major HCV genotypes and epidemiologically important subtype 1b for further characterization. We infected Huh7.5 cells cultured in DMEM+10% FBS with Core-NS2 recombinants indicated in FIG. 2. DMEM+10% FBS was replaced by AEM, when 40-80% of culture cells were infected (FIG. 2). From these cultures, high-titer sf-HCVcc virus stocks were harvested at four consecutive time points, before cultures were closed. Peak infectivity titers between 4.7 and 6.2 log 10 FFU/ml were observed for sf-HCVcc, with sf-J4(1b) and sf-ED43(4a) showing the lowest and sf-SA13(5a) showing the highest titers (FIG. 2 and FIG. 14). Thus, sf-HCVcc stocks showed 0.6 to 2.1 log 10 FFU/mL increased infectivity titers compared to previously described HCVcc reference stocks (FIG. 14). HCV RNA and Core titers for sf-HCVcc and HCVcc reference stocks were similar (FIG. 14). Thus, genotype 1-6 sf-HCVcc showed increased specific infectivities compared to HCVcc reference stocks (FIG. 14). This increase in specific infectivity was most pronounced for recombinants with comparatively low infectivity titers. Thus, based on RNA titers, specific infectivity was 20-fold increased for sf-J4(1b) and 40-fold increased for sf-ED43(4a) compared to their HCVcc counterparts (FIG. 14). This resulted in differences in specific infectivity between sf-HCVcc of different genotypes being smaller than those between HCVcc of different genotypes. For sf-HCVcc, based on RNA titers, specific infectivities were between $1/40$ FFU/IU and $1/631$ FFU/IU, while HCVcc showed specific infectivities between $1/398$ FFU/IU and $1/12,589$ FFU/IU (FIG. 14).

Higher Infectivity Titers of sf-HCVcc Might be Due to Increased Viral Release and Specific Infectivity.

We next aimed at determining if the observed differences in infectivity titers were due to the fact that DMEM+10% FBS cultures were split at regular intervals, while AEM cultures were kept over-confluent. Huh7.5 cell cultures were infected with SA13(5a) and (i) maintained in DMEM+10% FBS and split every 2-3 days, (ii) maintained in DMEM+10% FBS without splitting, or (iii) maintained in AEM without splitting (FIG. 3A). The DMEM+10% FBS culture yielded a peak infectivity titer of 5.6 log 10 FFU/ml, while the AEM culture yielded a peak infectivity titer of 6.1 log 10 FFU/ml (FIG. 3A). However, the DMEM+10% FBS culture maintained without splitting reached only 4.6 log 10 FFU/mL (FIG. 3A). This suggested that the high infectivity titers observed for the AEM cultures were not due to reduced stress related to avoiding cell culture splitting.

We subsequently investigated cell viability and proliferation of cells cultured in AEM versus DMEM+10% FBS. After 48 hours of culture in AEM, when increased infectivity titers were observed, cell viability and proliferation of AEM cultures was similar to that of DMEM+10% FBS cultures (FIG. 3B). Thus, changes in cell viability or proliferation did not explain the increased infectivity titers observed.

We further investigated, whether sf-HCVcc were more stable than HCVcc, which might contribute to the observed increase in infectivity titers. Up to 5 freeze/thaw cycles did not results in major decrease in infectivity or differences in infectivity for SA13(5a), sf-SA13(5a) or sf-SA13(5a) supplemented with 10% FBS (FIG. 3C). Incubation for 48 hours at 4° C. resulted in a minor decrease in infectivity of sf-SA13(5a) compared to SA13(5a) and sf-SA13(5a) supplemented with 10% FBS (FIG. 3D). Incubation for 4 to 48 hours at room temperature and 37° C. resulted in a gradual decrease in infectivity; this decrease was more pronounced for sf-SA13(5a) than for SA13(5a), and partially rescued by addition of 10% FBS to sf-SA13(5a) (FIG. 3D). Thus, FBS might result in stabilization of HCVcc. However, apparently, increased infectivity titers were not caused by increased stability of sf-HCVcc.

Figure 3:
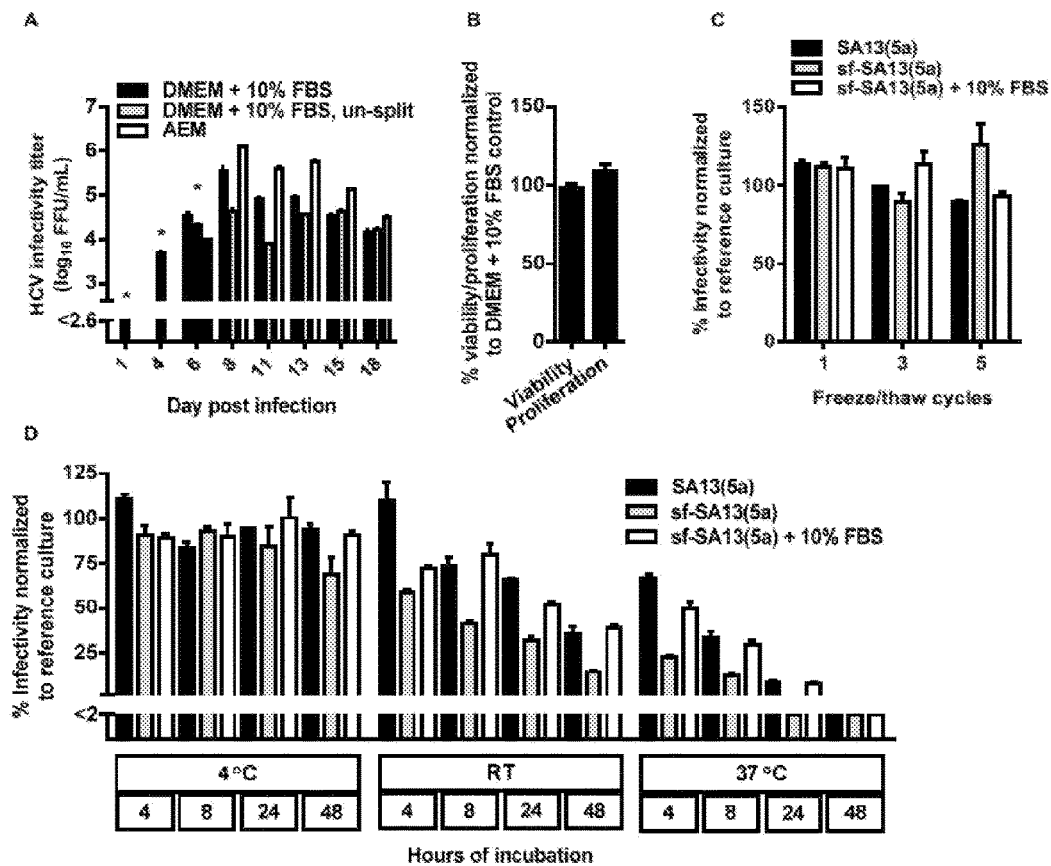

In order to investigate whether certain steps of the viral life cycle were affected by serum-free culture conditions, we carried out single-cycle virus production assays using CD81-deficient S29 cells, which are derived from Huh7.5 cells. Following transfection with SA13(5a) HCV RNA, AEM cultures showed an ~1 log decrease in intracellular HCV Core and infectivity titers compared to DMEM+10% FBS cultures, indicating a decrease in viral replication/translation (FIGS. 4A and B). In contrast, AEM and DMEM+10% FBS cultures showed similar extracellular Core titers, but AEM cultures had a ~1 log increase in extracellular infectivity titers compared to DMEM+10% FBS cultures. These findings suggest that AEM culture resulted in increase in viral release and that sf-HCVcc had increased specific infectivity compared to HCVcc. Furthermore, for HCVcc, the peak extracellular infectivity titer was observed 48 hours post transfection followed by a decrease at 72 hours post transfection, while for sf-HCVcc high titers were observed at both time points (FIG. 4B). This is in agreement with the prolonged peak of infection observed in Huh7.5 cells (FIGS. 1-3).

Infectious sf-HCVcc Particles Displayed a Homogeneous Density Profile.

To investigate their biophysical properties we subjected sf-HCVcc (FIG. 2) to equilibrium buoyant density ultracentrifugation on iodixanol gradients. As described previously for genotype 2a, 3a, 5a and 6a HCVcc, we observed that infectious genotype 1-6 HCVcc particles constituted heterogeneous virus populations with buoyant densities between 1.01-1.10 g/mL (FIG. 5). Interestingly, for genotype 1-6 sf-HCVcc harvested after 48 hours of cell culture with AEM, we detected up to 92% of recovered infectious sf-HCVcc at a single density of ~1.10 g/mL, following iodixanol gradient ultracentrifugation. Furthermore, between 71% and 97% of recovered infectious sf-HCVcc could be collected in three fractions with densities between 1.09 g/mL and 1.12 g/mL (FIG. 5). Thus, infectious genotype 1-6 sf-HCVcc constituted a more homogeneous virus population compared to their HCVcc counterparts.

Infectious sf-HCVcc Particles were Apparently Associated with ApoE.

The altered density profile of sf-HCVcc might indicate an altered association with lipoproteins. To investigate if sf-HCVcc was associated with ApoE, a key component of HCV associated lipoproteins, we carried out neutralization assays using a monoclonal antibody directed against ApoE. Due to limited availability of this antibody, we studied only the genotype 5a recombinant. SA13(5a) and sf-SA13(5a) showed a similar concentration-dependent response with median inhibitory concentrations (IC50) of 1.3 μg/mL for SA13(5a) and 1.1 μg/mL for sf-SA13(5a), and almost complete neutralization achieved at the highest α-ApoE concentrations (FIG. 6A), suggesting that genotype 5a HCVcc and sf-HCVcc showed similar association with ApoE. These data were confirmed by neutralizing SA13(5a) and sf-SA13(5a) using Anti-Apolipoprotein E antibody (ab24139, abcam). Using this polyclonal rabbit IgG, complete neutralization, as well as 50% neutralization, was observed at similar dilutions for SA13(5a) and sf-SA13(5a) (data not shown).

We further carried out immunoprecipitation of SA13(5a) and sf-SA13(5a) with the ApoE specific monoclonal antibody also used for neutralization experiments in FIG. 6A. We observed no major differences in the amount of viral RNA precipitated by this antibody (FIG. 6B). Collectively, these data indicate that HCVcc and sf-HCVcc showed similar association with ApoE.

Establishment of the Use of sf-HCVcc in Biological Assays.

To further characterize sf-HCVcc, we aimed at studying routes of sf-HCVcc entry and sf-HCVcc sensitivity to neutralizing antibodies. To avoid potential in vitro association of sf-HCVcc with FBS components such as lipoproteins, we aimed at replacing DMEM+10% FBS, typically used in such assays, by AEM during the viral infection step. However, using AEM, in initial experiments with genotype 5a and 2a viruses, we found greatly reduced infectivity for sf-SA13 (5a) and sf-J6(2a). Interestingly, SA13(5a) and J6(2a) infectivity was also reduced when these viruses were diluted in AEM prior to infection (FIG. 7A and data not shown). This loss of infectivity was not due to down-regulation of important HCV co-receptors on AEM cultured Huh7.5 cells, since expression of CD81, LDLr, SR-BI and claudin-1 was similar in Huh7.5 cells cultured for three hours in either DMEM+ 10% FBS or AEM, as determined by flow cytometry (FIG. 8).

To determine how infectivity of sf-HCVcc in AEM could be rescued, we diluted sf-SA13(5a) in DMEM+10% FBS (reference culture), DMEM, AEM, or AEM supplemented with 10% FBS and/or GlutaMax (a glutamine supplement present in DMEM+10% FBS culture medium but not in AEM). For sf-SA13(5a) diluted in AEM, infectivity was only 12% of infectivity of the reference culture (FIG. 7B). While supplementing AEM with GlutaMax did not influence infectivity, supplementing AEM with 10% FBS or 10% FBS and GlutaMax increased infectivity of sf-SA13(5a) to 67% and 68% respectively, compared to the reference culture (FIG. 7B). When sf-SA13(5a) was diluted in DMEM without FBS (GlutaMax only), infectivity was only 30% compared to the reference culture (FIG. 7B). Apparently other FBS components than lipoproteins and lipoprotein-associated factors mediated this enhancement of infectivity, because supplementing AEM with either VLDL, low density lipoprotein, high density lipoprotein, ApoB, ApoCI, ApoE or water-soluble cholesterol did not rescue infectivity, while lipoprotein deficient FBS partly restored infectivity (data not shown). Furthermore, we observed that sf-SA13(5a) infectivity correlated with the % of FBS in AEM (FIG. 7C). These findings suggested that yet undefined factors in FBS culture medium supplement were crucial for infectivity of HCVcc and sf-HCVcc. Therefore, we investigated if sf-HCVcc was able to associate in vitro with FBS components, leading to alteration of the observed sf-HCVcc density profile. We incubated sf-SA13(5a) with different media and serum concentrations in the absence of cells. Such incubations did not affect the density profile of sf-SA13(5a) (FIG. 9), suggesting that association between sf-HCVcc and serum components did not occur to an extent that influenced the previously observed density profile (FIG. 5). Thus, it was feasible to carry out further biological studies of sf-HCVcc in AEM supplemented with 10% FBS.

Entry of sf-HCVcc Depended on HCV Co-Receptors CD81, LDLr and SR-BI as Well as on Clathrin-Mediated Endocytosis.

To investigate if sf-HCVcc differed from HCVcc regarding entry into the host cell, we first studied HCV co-receptors LDLr and SR-BI, which might interact with lipoprotein components on the LVP, as well as CD81, supposed to directly interact with E2.

When blocking CD81, for genotype 1-6 HCVcc, maximum blocking rates (Bmax) of ~100% were observed at the highest anti-CD81 concentrations; for these viruses, similar blocking rates were previously observed. Genotype 1-6 sf-HCVcc showed similar concentration-dependent sensitivity towards CD81 blocking as their HCVcc counterparts (FIG. 10, left column).

When blocking LDLr, we found concentration-dependent blocking for genotype 1-6 HCVcc. Bmax values were between 69% for ED43(4a) and 100% for SA13(5a) at the highest concentrations of α-LDLr, suggesting genotype/isolate-specific differences in dependency on LDLr (FIG. 10, middle column). Genotype 1-6 sf-HCVcc could also be blocked in a concentration-dependent manner, with Bmax values between 33% for sf-HK6a(6a) and 74% for sf-H77 (1a) at the highest concentrations of α-LDLr. While sf-H77 (1a), sf-552(3a) and sf-ED43(4a) showed similar Bmax values as their HCVcc counterparts, sf-J4(1b), sf-J6(2a), sf-SA13(5a) and sf-HK6a(6a) showed 31-55% lower Bmax values than their HCVcc counterparts, suggesting that sf-HCVcc of certain genotypes had lower dependency on LDLr than their HCVcc counterparts.

Blocking of SR-BI had only limited effect on entry of J4(1b) and HK6a(6a) HCVcc with Bmax values <50% (FIG. 10, right column). For HCVcc of other genotypes we observed concentration-dependent blocking with Bmax values between 51% for J6(2a) and 80% for H77(1a) at the highest concentrations of anti-SR-BI. Thus, sensitivity to SR-BI blocking apparently depended on the genotype/isolate. Blocking of SR-BI also had limited effect on entry of sf-J4(1b) and sf-HK6a(6a). Entry of sf-HCVcc of other genotypes was blocked in a concentration-dependent manner, with Bmax values between 60% for sf-SA13(5a) and 86% for sf-H77(1a). Bmax values were similar between HCVcc and sf-HCVcc of the same genotype. Thus, overall, HCVcc and sf-HCVcc of the same genotype showed similar sensitivity to SR-BI blocking.

Finally, we studied dependency of genotype 1-6 sf-HCVcc on clathrin-mediated endocytosis. When pretreating cells with chlorpromazine, we observed concentration-dependent blocking rates of up to 93%, suggesting that both sf-HCVcc and HCVcc depended on clathrin-mediated endocytosis (FIGS. 11A-G). We were not able to achieve 100% blocking for any of the recombinants at 10 μg/mL chlorpromazine, the highest concentration not resulting in cytotoxic effects (FIG. 11H). Interestingly, most sf-HCVcc were slightly more sensitive to chlorpromazine treatment than their HCVcc counterparts. This difference was greatest for J4(1b), ED43(4a) and HK6a(6a). For J6(2a) and SA13 (5a) no obvious difference was observed, while H77(1a) and S52(3a) showed relatively small differences. This suggested that dependency on clathrin-mediated endocytosis might be slightly greater for sf-HCVcc of most genotypes/isolates than for HCVcc.

In conclusion, these data suggest that, overall, entry of HCVcc and sf-HCVcc relied on CD81, LDLr and SR-BI HCV co-receptors as well as on clathrin-mediated endocytosis, with exception of genotype 1b and 6a particles, which could not be blocked by anti-SR-BI. However, we detected minor differences for recombinants of different HCV genotypes and for HCVcc versus sf-HCVcc regarding dependency on certain receptors and clathrin-mediated endocytosis Chronic-phase patient sera and monoclonal antibodies against conformational epitopes in E1E2 and E2 neutralize sf-HCVcc.

To investigate if there were differences between HCVcc and sf-HCVcc in sensitivity to neutralizing antibodies, we first did neutralization of genotype 1-6 viruses using serum from genotype 1a infected Patient H, taken 29 years after acute infection (H06). For HCVcc, as previously described, S52(3a) was the least sensitive to neutralization with H06 (FIG. 12D). For HCVcc of other genotypes we observed dilution-dependent neutralization with IC50 values ranging from $1/1{,}436$ to $1/233{,}209$ and relatively high neutralization rates by high concentrations of H06 serum (FIG. 12). For genotype 1-6 sf-HCVcc, we found similar neutralization patterns as for their HCVcc counterparts. For all sf-HCVcc except S52(3a) we observed dilution dependent neutralization with IC50 values ranging from $1/605$ to $1/156{,}666$ and relatively high neutralization rates by high concentrations of H06 serum (FIG. 12). Thus, sf-HCVcc particles showed similar susceptibility to neutralizing antibodies in chronic phase patient serum as HCVcc.

To confirm these observations, we next neutralized SA13 (5a) and sf-SA13(5a) with a genotype 5a chronic-phase patient serum (SA3). These viruses showed similar neutralization profiles, with IC50 values of $1/28$ for SA13(5a) and $1/654$ for sf-SA13(5a) as well as high neutralization rates by high concentrations of SA3 serum (FIG. 13A).

Finally, we tested a panel of monoclonal antibodies (AR1B and AR2A-5A) targeting defined conformational epitopes in E1E2 and E2, against SA13(5a) and sf-SA13 (5a). AR1B was the least efficient for both viruses without reaching a top plateau (FIG. 13B). AR2A-5A neutralized SA13(5a) and sf-SA13(5a) with similar concentration-response profiles, with IC50 values ranging from 0.33 to 0.53 μg/mL for SA13(5a) and 0.19 to 1.56 μg/mL for sf-SA13 (5a); for both viruses complete neutralization was observed at high antibody concentrations (FIG. 13C-F). This further supports that sf-HCVcc show similar sensitivity to neutralizing antibodies as HCVcc. In addition, these findings suggest that sf-HCVcc and HCVcc do not show major differences regarding conformation of E1 and E2.

Discussion

In this study, we describe the generation and characterization of genotype 1-6 serum-free HCVcc particles, using AEM to culture infected Huh7.5 hepatoma cells. Compared to HCVcc, sf-HCVcc showed similar biological properties but increased infectivity titers and a homogenous single-peak density profile. These unique characteristics, as well as the reduced concentration of non-HCV proteins in serum-free culture supernatants, are expected to facilitate generation of purified and concentrated virus stocks, required for vaccine development and biophysical studies of HCV particle composition. Further, the developed serum-free culture conditions might reduce the risk of contamination with adventitious microbial agents in future vaccine antigen preparations.

Efficient production of HCVcc has primarily been achieved in the continuous hepatoma cell line Huh7 and derived cell lines, such as Huh7.5 cells. Due to their increased permissiveness to infection with recombinant HCV, Huh7.5 cells were previously used for cell culture adaptation and growth of HCV genotype 1-6 recombinants used in this study.

According to WHO recommendations, a wide range of continuous cell lines are now considered as suitable substrates for production of various medicinal substances if certain requirements are met. These requirements include use of well-characterized cell banks, use of suitable manufacturing procedures aiming at a high degree of purification of the end product, and thorough characterization of the end product. Thus, Huh7.5 cells could potentially be characterized to comply with these recommendations, allowing their use for vaccine development. Huh7 derived cell lines have typically been subjected to long-term passage using serum-containing growth medium and animal-derived trypsin. According to WHO recommendations, animal derived products should be reduced or eliminated from cell cultures used for production of medicinal substances due to risk of contamination with adventitious microbial agents.

In this study, we describe a method for production of sf-HCVcc, thus avoiding the use of trypsin and bovine serum during the virus production phase. To further reduce presence of animal-derived components in sf-HCVcc producing cell culture, it might be possible to culture Huh7.5 cells in serum-free medium, prior to sf-HCVcc production. Alternatively, based on recently generated knowledge on host-factors required for HCV infection, it might be possible to engineer cell lines already approved for vaccine development with susceptibility to HCV infection. However, this might be a cumbersome process and might require re-approval of the modified cell-line. Of note, most genotype 1-6 recombinants used in this study contained adaptive mutations conferring efficient growth in Huh7.5 cells. For HK6a(6a) cell culture adaptive mutations localized to the envelope proteins. In addition, in this study H77(1a) and J4(1b) polyclonal virus stocks had acquired putative cell culture adaptive mutations in the envelope proteins. In future studies, it will be of relevance to develop a panel of genotype 1-6 recombinants without envelope mutations, thus not differing from naturally occurring isolates.

Recently, proof-of-concept for immunogenicity of genotype 2a HCVcc was obtained, since immunization of mice resulted in induction of HCV neutralizing antibodies. This underlines the potential of inactivated HCVcc particles as future vaccine antigens. However, an experimental adjuvant, not suitable for human use was used. Further, HCVcc used for immunizations were grown in cell culture medium supplemented with 2% FBS, even though the authors had previously reported development of serum-free cultures for genotype 2a recombinants JFH1 and J6/JFH1, using growth medium DMEM/F-12 supplemented with Insulin-Transferrin-Selenium-X. In contrast to our study, infectivity titers and specific infectivity of 2a virus from such serum-free cultures were apparently only equal to or lower than titers of viruses from serum-supplemented cultures. In addition, serum-free 2a HCVcc showed a similar density profile as 2a HCVcc derived from serum-containing cell culture, following sucrose gradient ultracentrifugation. These differences between previously produced serum-free 2a HCVcc and sf-HCVcc described in this study are most likely due to the different culture media used and/or other differences in experimental conditions.

We describe establishment of serum-free cell cultures producing HCV particles of prototype strains of genotypes 1-6 with favourable biophysical- and biological characteristics (FIGS. 2 and 5 and FIG. 14). Supernatant infectivity titers of sf-HCVcc were 0.6 to 2.1 log 10 FFU/ml higher than titers of HCVcc (FIG. 14 and FIG. 2). Of the panel of previously developed HCVcc recombinants, SA13(5a) showed the highest infectivity titers (~5 log 10 FFU/ml). Infectivity titers of >6 log 10 FFU/ml, as observed for sf-SA13(5a) (FIG. 14 and FIGS. 2F and 3A), are among the highest infectivity titers reported to date for cell culture grown HCV. Furthermore, recombinants with relatively low infectivity titers, such as J4(1b) and ED43(4a), yielded significantly increased infectivity titers, when grown under serum-free conditions (FIG. 14 and FIGS. 2B and E).

Genotype 1b is considered to be the most prevalent genotype worldwide and in certain countries, such as Egypt, genotype 4a has a prevalence of up to 15%; thus genotype 4a sf-HCVcc might prove an important antigen for vaccine trials. The reason why serum-free culture conditions resulted in increased infectivity titers remains to be fully elucidated. Our studies indicated that increased infectivity in AEM cultures was not due to (i) avoiding stress related to cell splitting (FIG. 3A), (ii) changes in Huh7.5 cell viability or proliferation (FIG. 3B) or (iii) increased stability of sf-HCVcc (FIGS. 3C and D). While in S29 cells, serum-free culture conditions resulted in reduction of viral replication/translation, they increased viral release and specific infectivity, possibly contributing to the higher infectivity titers observed (FIG. 4).

Specific infectivities were generally higher for sf-HCVcc than for HCVcc as observed in both Huh7.5 cell cultures (FIG. 14) and S29 cell cultures (FIG. 4). This is in line with previous reports that HCVcc fractions with the highest specific infectivity had a buoyant density between 1.09-1.10 g/mL, similar to the density of the majority of infectious sf-HCVcc particles (FIG. 5).

Higher specific infectivity might be due to absence of serum, which might have non-specific neutralizing or inhibitory activity; alternatively, less immature viral particles might be produced using the developed culture conditions.

Furthermore, in our serum-free cultures, supernatants with high infectivity titers could typically be harvested for a prolonged period of time compared to DMEM+10% FBS cultures (FIGS. 1-4). For example, for SA13(5a), high-titer supernatants could typically be harvested at 2-3 subsequent time points in DMEM+10% FBS cultures, whereas in serum-free cultures, high-titer supernatants could be harvested at 4-6 subsequent time points (FIGS. 2F and 3A). This further increased the yield of infectious virus that could be harvested from serum-free cultures.

In contrast to HCVcc, sf-HCVcc displayed a homogeneous density distribution with a single peak of infectious virus at densities of ~1.10 g/mL, following iodixanol gradient ultracentrifugation (FIG. 5). We believe that the density profile of sf-HCVcc might allow more effective density-based purification and concentration using ultracentrifugation and gel chromatography, since a single fraction, containing the majority of infectious virus, can be collected. Density changes were previously observed for HCVcc without hypervariable region 1 (HVR1), HCVcc with a specific E2 mutation and for HCV recovered from HCVcc-infected chimpanzees and uPA-SCID mice engrafted with human liver cells.

These density changes were suggested to be due to differences in lipoprotein association. We showed that sf-SA13(5a) could be neutralized as efficiently as its HCVcc counterpart by a monoclonal α-ApoE antibody and polyclonal α-ApoE IgG (FIG. 6A and data not shown). Further, immunoprecipitation of sf-SA13(5a) and SA13(5a) showed similar efficacy (FIG. 6B). These data indicate that HCVcc and sf-HCVcc do not show major differences in association to ApoE, and thus possibly to lipoproteins. Therefore, further studies will be required to elucidate the cause for the observed density shift (FIG. 5). Preliminary studies indicated a decrease in intracellular lipid content in serum-free cultures (data not shown). However, determination of expression levels of genes involved in lipid production or of lipid/lipoprotein composition of HCVcc versus sf-HCVcc was considered outside the scope of this study.

Compared to HCVcc, HCVcc without HVR1, displaying a similar density distribution as sf-HCVcc, were less susceptible to blocking of SR-BI and more susceptible to neutralizing antibodies. Furthermore, previously described serum-free HCVcc were more susceptible to blocking of CD81 and SR-BI and to neutralization by a monoclonal antibody targeting E2 (AP33). Of note, in this study biological assays were carried out in AEM supplemented with FBS, which was required for viral infection, but did apparently not alter composition of sf-HCVcc lipo-viral particles (FIGS. 7 and 9). When blocking CD81 and SR-BI, we did not observe major differences between sf-HCVcc and HCVcc (FIG. 10). Even though sf-HCVcc of certain genotypes showed slightly lower dependency on LDLr and slightly higher dependency on clathrin mediated endocytosis than their HCVcc counterparts (FIGS. 10 and 11), overall our findings suggested that sf-HCVcc relied on similar routes of entry as HCVcc. In the future, it will be of interest to further investigate the small differences observed for LDLr usage and dependency on clathrin mediated endocytosis using different blocking antibodies and alternative methods of inhibition such as RNA interference. We further confirmed previous results showing that HCVcc of genotype 1-6 showed similar dependency on CD81. Previously, we reported that blocking SR-BI had a similar effect on genotype 1-6 HCVcc entry. However, in this study and another recent study by our group, using a different blocking antibody, we found differential sensitivity of genotype 1-6 HCVcc to SR-BI blocking.

Single E2 mutations in culture adapted JFH1(2a) were reported to cause reduced dependency on SR-BI. Further studies are required to elucidate if the E2 mutations present in HK6a(6a) and J4(1b) HCVcc virus stocks mediated reduced dependency on SR-BI. For genotype 1-6 HCVcc, we also observed small but consistent differences regarding dependency on LDLr (FIG. 10). Whereas dependency on LDLr for entry has been shown for JFH1(2a) and was recently shown for H77(1a), J6(2a) and S52(3a) HCVcc, this study is the first to show dependency on LDLr for J4(1b), ED43(4a), SA13(5a) and HK6a(6a) HCVcc. In future studies, also involving recombinants of additional isolates of each genotype, it will be of interest to investigate if different genotypes, subtypes or isolates differ regarding receptor usage.

Compared to HCVcc, sf-HCVcc showed similar sensitivity to neutralization by chronic phase patient sera and human monoclonal antibodies targeting conformational epitopes in E1E2 and E2 (FIGS. 12 and 13). These results suggest that sf-HCVcc resemble HCVcc regarding epitope exposure and conformation, of importance for vaccine development using sf-HCVcc as antigen.

In conclusion, we have established a method allowing for robust production of genotype 1-6 sf-HCVcc with favourable biological and biophysical characteristics. Serum-free culture apparently reduced viral replication/translation but enhanced viral release and specific infectivity. Sf-HCVcc had increased infectivity titers compared to HCVcc, and compared to serum-free HCVcc reported previously, thus contributing to an increased yield of infectious virus from infected cell cultures. Furthermore, sf-HCVcc displayed a homogeneous density distribution. Together with a reduced concentration of non-HCV proteins in supernatants from serum-free cultures, these features are expected to facilitate viral purification and concentration required for vaccine production and morphological analysis of HCV particles. Biologically, sf-HCVcc particles resembled their HCVcc counterparts regarding association to ApoE, routes of viral entry and sensitivity to neutralizing antibodies.

Thus, sf-HCVcc particles could prove important as antigens in a prophylactic HCV vaccine against all six epidemiologically important HCV genotypes. To this aim future studies are required, focussing on establishment of large-scale sf-HCVcc production as well as efficient purification, concentration and inactivation. Finally, it will be of great interest to test immunogenicity of genotype 1-6 sf-HCVcc in small animal models.

Example 2—Adaptive Mutations of HCV Genotype 5a Core-NS2 Recombinant and Identification of Mutations Conferring Increased Viral Fitness and High Infectivity Titer Materials and Methods
Huh7.5 Cell Cultures.

Human hepatoma Huh7.5 cells were cultured in filter-cap culture flasks (Nunc) in DMEM (Gibco/Invitrogen) supplemented with 10% fetal bovine serum (FBS, [Sigma]), penicillin (100 U/mL) and streptomycin (100 µg/mL) (Gibco/Invitrogen), hereafter referred to as complete DMEM. Cells were split every 2-3 days by washing in PBS (Sigma), followed by detachment using trypsin (Sigma). Serum-free cell culture was performed in adenovirus expression medium (AEM) supplemented with penicillin (100 U/mL) and streptomycin (100 µg/mL), hereafter referred to as AEM. AEM cultures were not split but instead kept overconfluent during virus production (Mathiesen et al. data submitted for publication). Huh7.5 cells were maintained at 37° C. and 5% $CO_2$.

Construction of SA13/JFH1-Based Mutant Constructs.

The previously described plasmid pSA13/JFH1C3405G, A3696G was used as backbone for generating mutant constructs. Single point mutations A3042G and T2687G were inserted using fusion PCR and cloning. All PCRs were performed using Pfu polymerase (Stratagene). Single point mutation A6443G was inserted using QuikChange II XL Site-Directed Mutagenesis Kit (Stratagene/Agilent). QuikChange forward primer 5'-GCCCTTGCGGCGCCGA-CATCTCTGGCAATG-3' and reverse primer 5'-CATTGC-CAGAGATGTCGGCGCCGCAAGGGC-3' were generated using PrimerX. Single point mutations C1043G, G1043C, C1493A, A1493C and A6443G were inserted using QuikChange II XL Site-Directed Mutagenesis Kit (Stratagene/Agilent). Two pUC57 plasmids encoding (i) an SA13 Core-E2 sequence containing mutations C680T, T900C, G1043C and A1493C, and (ii) a JFH1 NS5A-NS5B sequence containing mutations A7044G, T7086C, T7128C, T7350C, G7895T, A7897G and T8919C, were synthesized (GenScript). Target sequence of plasmid (i) was introduced by digestion with KpnI and BlpI FastDigest enzymes (Fermentas). Target sequence of plasmid (ii) was introduced by digestion with SanDI and BstZ17I FastDigest enzymes (Fermentas). The HCV sequences of plasmids were verified by sequencing of the final DNA preparation (HiSpeed Plasmid Maxi Kit, [Qiagen]).

Transfection and Infection of Huh7.5 Cells.

For transfection of Huh7.5 cells, 350,000 cells/well were seeded in 6-well plates (Nunc) and incubated for 24 hours. Plasmids (10 µg) were linearized by over-night digestion with XbaI (New England Biolabs). Linearized plasmids were purified using Wizard® SV Gel and PCR Clean-Up System (Promega). In vitro transcription was performed using T7 RNA polymerase (Promega) for 2 hours at 37° C. Transfection was performed by incubating 5 μL lipofectamine 2000 (Invitrogen) and the RNA transcripts in 500 μL serum-free Opti-MEM (Gibco/Invitrogen) for 20 minutes at room temperature. RNA-lipofectamine complexes were added to the pre-plated cells and incubated for 16-24 hours. Transfection efficiencies and culture spread were determined by HCV NS5A immunostaining (see below). Supernatants were harvested every 2-3 days when cultures were split, sterile filtered and stored at −80° C.

For infection of Huh7.5 cells in culture flasks, cells were seeded and incubated for 24 hours. When cells were evaluated to be ~80% confluent, they were infected at a multiplicity of infection (MOI) of either 0.003 or 0.0003 for 3 hours (see Figure legends for details). After infection, cells were washed in PBS and incubated in complete DMEM. Infection spread was monitored by HCV NS5A immunostaining (see below). Supernatants were harvested every 2-3 days when cells were split, sterile filtered, and stored at −80° C. For serum-free cultures, cells were infected in complete DMEM as described above and spread was monitored by NS5A immunostaining. When ~80% of the cells were NS5A positive, complete DMEM was removed and the cells were washed in PBS before AEM was added to the cells. Every 2-3 days, supernatants were harvested, sterile filtered and stored at −80° C., and fresh AEM was added to the cells without splitting them.

Evaluation of HCV Transfected and Infected Cell Cultures.

HCV spread was monitored by HCV NS5A immunostaining. Cells plated onto chamber slides (Nunc) the previous day were fixed in ice-cold acetone (Sigma) for 10 minutes. Fixed cells were washed twice in PBS and twice in PBS+0.1% Tween-20 (Sigma), hereafter referred to as PBS/Tween. Cells were stained for 2 hours at room temperature, using primary anti-NS5A antibody 9E10 at a 1:1,000 dilution in PBS+1% bovine serum albumin (BSA, [Roche Applied Science])+0.2% skim milk, hereafter referred to as PBS/BSK. Cells were washed twice in PBS and twice in PBS/Tween. Cells were stained for 10 minutes using a mix of secondary antibody Alexa Fluor 594-conjugated goat anti-mouse IgG (H+L) (Invitrogen) at a 1:500 dilution and Hoechst 33342 (Invitrogen) at a 1:1,000 dilution in PBS/Tween. Cells were washed twice in PBS, before being covered by Fluoromount-G (SouthernBiotech) and a coverslip.

Culture supernatant infectivity titers were determined as Focus Forming Units (FFU)/mL. Huh7.5 cells (6,000 cells/well), seeded the previous day onto poly-D-lysine coated 96-well plates, were infected with serially diluted supernatants (lowest dilution 1:2). Forty-eight hours after infection, cells were fixed in ice-cold methanol (Sigma) for 10 minutes and washed twice in PBS/Tween. Cells were incubated for 5 min with 3% H2O2 at room temperature before being washed twice in PBS/Tween. Cells were stained for 24 hours at 4° C. using primary anti-NS5A antibody 9E10 at a 1:1,000 dilution in PBS/BSK. Cells were washed twice in PBS/Tween and stained for 30 minutes at room temperature using secondary antibody ECL anti-mouse IgG horseradish peroxidase (HRP)-linked whole antibody (GE Healthcare Amersham) at 1:300 dilution in PBS/Tween. NS5A positive cells were visualized using a DAB substrate kit (Dako). FFU were counted and their sizes (mm2) were determined automatically, using an ImmunoSpot series 5 UV analyser (CTL Europe GmbH) with customized software as previously described. Lower limit of detection was calculated for each 96-well plate as previously described.

Serial passage of SA13/JFH1 in cell culture flasks and 96-well microtiter plates. For serial passage in cell culture flasks, 3×10$^6$ cells were seeded into T80 flasks and infected as described above with a previously described 2nd passage SA13/JFH1C3405G,A3696G stock. When infection had peaked as determined by immunostaining, 5 mL supernatant, collected one time point prior to the peak of infection, was used to infect naïve cells plated in a new T80 flask for 3 hours. After infection, cells were washed and complete DMEM was added. This procedure was repeated for serial passage of SA13/JFH1C3405G,A3696G in T80 flasks.

For serial passage in 96-well plates, we employed an approach similar to what has been previously described for adaptation of J6/JFH1. For initial infection of Huh7.5 cells in 96-well plates, 5,000 cells/well were seeded in a poly-D-lysine coated 96-well plate (Nunc) and incubated for 24 hours. Initially, each well was infected for 72 hours with 200 μL SA13/JFH1p17 corresponding to an MOI of 0.01. After incubation, supernatant was collected from all wells and stored at −80° C. The infected cells were fixed and stained for HCV NS5A (see above). In subsequent serial passages, 5-100 μL of the saved supernatant (the same volume for all wells) was transferred from each well to the corresponding wells of a poly-D-lysine coated 96-well plate with naïve Huh7.5 cells, seeded the previous day. Complete DMEM was added to each well for a total volume of 200 μL, and cells were incubated for 3 hours. After incubation, virus was removed and cells were washed in PBS before 200 μL complete DMEM was added and cells were incubated for 72 hours. Following incubation, supernatant was saved from all wells and cells were fixed in ice-cold methanol and stained for NS5A as described above. Single HCV NS5A positive cells were counted automatically using an ImmunoSpot series 5 UV analyser with customized software as described previously.

Endpoint Dilution.

Huh7.5 cells (6000 cells/well), plated the previous day onto poly-D-lysine coated 96-well plates, were infected with 12 replicate serial dilutions of SA13/JFH1p31/C5 from 10-1 to 10-8. Forty-eight hours post infection, supernatant was collected and stored at −80° C. Cells were fixed in ice-cold methanol and HRP-stained for HCV NS5A as described above. FFU were counted automatically, as described.

Direct sequencing of SA13/JFH1 HCVcc. HCV RNA was purified from 200 μL culture supernatant using the High Pure Viral Nucleic Acid Kit (Roche Applied Science). In general, reverse transcription, 1st round PCR, and 2nd round nested PCR was carried out as described previously. Primers used to generate cDNA and PCR amplicons spanning the entire ORF have previously been described. Direct sequencing was carried out by Macrogen Europe.

Neutralization Assays.

Huh7.5 cells (7,000 cells/well) were seeded onto poly-D-lysine coated 96-well plates. The following day, IgG purified from serum from genotype 1a infected Patient H, taken 29 years after acute infection (H06), were diluted in complete DMEM as specified and mixed 1:1 with SA13/JFH1C3405G,A3696G, SA13/JFH1p7-NS5B or SA13/JFH1Core-NS5B 3rd passage supernatants. IgG-virus mixes were incubated at 37° C. for 1 hour before being added onto the pre-plated cells. Cells were incubated with IgG-virus mixes for 6 hours. After incubation, cells were washed in PBS and complete DMEM was added to all wells. Cells were incubated and fixed 48 hours post infection in ice-cold methanol and HRP-stained for HCV NS5A as described above. Single HCV NS5A positive cells were counted automatically as described. The % neutralization was calculated by relating counts of experimental wells to the mean count of six replicate wells with untreated control virus. Following logarithmic transformation of X-values, variable-slope sigmoidal dose-response curves [Y=Bottom+(Top−Bottom)/(1+10$^{(Log10EC50-X) \times HillSlope}$)] were fitted using GraphPad Prism 6.0 software. A "Bottom" constraint of 0 and a "Top" constraint of 100 were introduced.

Single-Cycle Virus Production Assay in S29 Cells.

Transfection of S29 cells for determination of intra- and extracellular Core values and infectivity titers, respectively, was carried out as previously described. Briefly, 400,000 CD81-deficient S29 cells were plated in 6-well plates 24 hours before transfection. In vitro transcription of plasmid clones was carried out as described above. RNA transcripts were DNAse treated using DNA RQ1 DNAse (Promega) and purified using RNeasy kit (Qiagen). RNA transcripts (2.5 µg) were transfected into S29 cells using lipofectamine 2000 as described above, but with the following changes to the protocol: S29 cells were incubated with transfection complexes for 4 hours during which complete DMEM had been exchanged by Opti-MEM. After 4 hours, Opti-MEM was replaced by complete DMEM. Cells were collected at 4 and 48 hours post transfection and prepared for determination of intracellular core and intracellular infectivity titers as previously described. Transfection supernatants were collected at 48 hours for determination of extracellular Core and extracellular infectivity titers as previously described. Infectivity titers were determined as described above. Core titers were determined by the ARCHITECT HCV Ag assay (Abbott).

Statistics. Non-parametric Mann-Whitney test was used to determine statistical differences between FFU sizes. Mann-Whitney test was performed using GraphPad Prism 6.0 software.

Results

Figure 17:
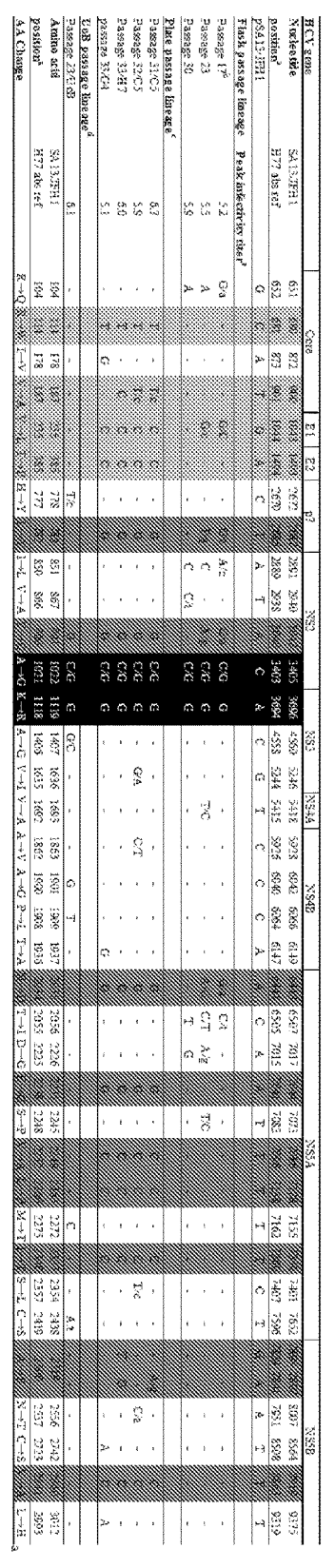

Significant increase of SA13/JFH1C3405G,A3696G titers following serial passage in Huh7.5 cells. In an attempt to generate a further adapted high-titer genotype 5a Core-NS2 JFH1-based HCVcc recombinant, we performed serial passage in Huh7.5 cells of a 2nd passage SA13/JFH1C3405G,A3696G virus stock. At Hvidovre Hospital (HVH, DK), we employed two different approaches for serial passage (FIG. 15A). For the "flask lineage" (FIG. 15A, black arrows), in each passage we infected Huh7.5 cells seeded in cell flasks and collected supernatants until massive cell death was observed due to HCV-induced cytopathic effect. The HCV infectivity titers of all collected supernatants were determined in order to compare peak infectivity titers in the different passages (FIG. 16A). Over time there appeared to be a modest increase in HCV infectivity titer, peaking in passage 29 with a peak titer of 6.0 log 10 FFU/mL (FIG. 16A). We also employed an alternative high-throughput 96-well plate passage technique, resulting in the "plate lineage" (FIG. 15A, blue arrows). For this approach, Huh7.5 cells seeded in a poly-D-lysine coated 96-well plate were infected for 72 hours with passage 17 supernatant of the flask lineage, and serially passaged, as described in Materials and Methods. After each passage, supernatant was collected from all wells and the plate was stained for HCV NS5A. Based on the NS5A staining of the passage 30-plate, we observed that the majority of the wells had become completely infected. We randomly selected six of the completely infected wells and transferred supernatant from these wells to naïve Huh7.5 cells. Supernatant was collected until massive cell death was observed and HCV infectivity titers were determined of all supernatants to compare peak titers (FIG. 16B). Peak titers in 5/6 of these passage 31 cultures were ~6 log 10 FFU/mL, comparable to peak titers of the flask lineage; however, the peak titer of a single passage 31 culture (SA13/JFH1p31/C5) was 6.7 log 10 FFU/mL (FIG. 16B and FIG. 17). This was significantly higher than what has typically been observed for SA13/JFH1 and at that point represented the highest infectivity titer recorded in our laboratory.

We did a 32nd passage of SA13/JFH1p31/C5 termed SA13/JFH1p32/C5. The peak titer of SA13/JFH1p32/C5 was determined to be 5.9, thus we were not able to reproduce peak titers of 6.7 log 10 FFU/mL (FIG. 17). We attempted to select individual SA13/JFH1 high-titer quasispecies by performing endpoint dilution of SA13/JFH1p31/C5. Cells plated in 96-well plates were infected with serial dilutions of SA13/JFH1p31/C5 ($10^{-1}$-$10^{-8}$ dilutions). After incubation, cells were stained for NS5A as described in Materials and Methods, and supernatant from wells with 1-2 FFU recorded were selected for testing in culture. Supernatant from these wells were transferred to naïve Huh7.5 cells. Four of the 6 cultures became infected and supernatant was collected from these until massive cell death was observed, and titrated to compare peak titers (FIG. 16C). Peak titers ranged from 5.1-6.0 log 10 FFU/mL (FIG. 16C, FIG. 17). Thus, none of these passage 33 cultures had peak titers matching that of SA13/JFH1p31/C5.

At the same time we analyzed a putative adapted passage 22 SA13/JFH1C3405G,A3696G stock generated independently by serial passage at The University of Birmingham (UoB, UK). We did a 23rd passage of this virus (FIG. 15B, green arrow), and titrated all supernatants collected (FIG. 17 and data not shown). This was termed the "UoB lineage". A Peak HCV infectivity titer of 6.1 FFU/mL was recorded, similar to titers of the flask lineage (FIG. 17).

Sequence analysis of serially passaged SA13/JFH1C3405G,A3696G revealed several putative adaptive mutations. To determine if serially passaged SA13/JFH1C3405G,A3696G had acquired putative adaptive mutations, we performed direct sequencing of RT-PCR amplicons from RNA purified from selected cultures (FIG. 15 and FIG. 17). A total of 37 nucleotide changes encoding different aa substitutions at 36 positions were identified (FIG. 17). Of these, two mutations were the original adaptive mutations described previously. Mutations were distributed throughout the HCV genome, however, most were found in the JFH1-portion of the genome (NS3-NS5B), especially in NS5A (FIG. 17). As the first 17 passages were identical between the flask- and plate lineages, it was interesting to observe how some mutations observed in passage 17 reverted back to wild-type (WT) plasmid sequence or became dominant in subsequent passages of either the flask- or the plate lineage. The UoB lineage displayed a different panel of mutations except for a single NS2 mutation (A3042G) that was also present as the dominant quasispecies in the common passage 17 of the flask- and plate lineage. In the subsequent flask lineage, this mutation had reverted back to WT by passage 30, however, in the plate lineage, this mutation had become dominant by passage 31 (FIG. 17). Interestingly, SA13/JFH1p23/UoB had not acquired any coding mutations in the structural proteins (FIG. 17).

In all serially passaged viruses sequenced above, the originally introduced adaptive mutation C3405G was observed as a C3405C/G 50/50 quasispecies (FIG. 17). The A3696G mutation remained stable during serial passage (FIG. 17).

Introduction of a panel of putative adaptive mutations into the SA13/JFH1C3405G,A3696G genome accelerated viral spread and increased HCV infectivity titers. Based on the consensus sequences of SA13/JFH1p31/C5 and SA13/JFH1p31/H7, the subcloned quasispecies which showed the highest infectivity titer, we selected a panel of 14 nucleotide mutations encoding 13 aa changes (FIG. 17, shaded), and introduced these into the original pSA13/JFH1C3405G, A3696G plasmid. Three different plasmid constructs were made: pSA13/JFH1C3405G,A3696G,A3042G, containing the original adaptive mutations and the single NS2 mutation A3042G, present in both the plate lineage and the UoB lineage; pSA13/JFH1p7-NS5B, containing the original adaptive mutations and 10 of the 14 putative adaptive mutations present in the nonstructural genes, encoding 9 aa changes (FIG. 17, dark grey shaded); and pSA13/JFH1Core-NS5B, containing the original adaptive mutations and the full panel of 14 putative adaptive mutations in structural- and nonstructural proteins encoding a total of 13 aa changes (FIG. 17, shaded). RNA transcripts of these recombinants were transfected into Huh7.5 cells together with transcripts of pSA13/JFH1 (original SA13/JFH1 plasmid without adaptive mutations) and pSA13/JFH1C3405G,A3696.

Cultures were terminated at day 7 due to massive cell death in most cultures. All cultures spread fast, showing high HCV infectivity titers on day 3, except for pSA13/JFH1, which only started to spread on day 7 (FIG. 18A). This was in accordance with previously published results for pSA13/JFH1. The pSA13/JFH1C3405G,A3696G and pSA13/JFH1C3405G,A3696G,A3042G transfections peaked on day 5 with peak titers ~5.0 log 10 FFU/mL (FIG. 18A). Interestingly, pSA13/JFH1p7-NS5B and pSA13/JFH1Core-NS5B showed accelerated spread kinetics, with peak titers on day 3. Titers were only modestly increased to 5.3 log 10 FFU/mL for pSA13/JFH1p7-NS5B, whereas pSA13/JFH1Core-NS5B peak titer was 5.7 log 10 FFU/mL (FIG. 3A). To investigate whether differences in spread kinetics and peak titers observed in transfections were also apparent after infection, we did a 1st passage, infecting Huh7.5 cells at an MOI of 0.003 using transfection peak supernatants. As observed in the transfection experiment, SA13/JFH1p7-NS5B and SA13/JFH1Core-NS5B spread faster, reaching infectivity titers above cut-off already at day 1 post infection. Both viruses peaked at day 5, whereas SA13/JFH1C3405G,A3696G and SA13/JFH1C3405G,A3696G,A3042G peaked on day 7 (FIG. 18B). Peak HCV infectivity titers were about 1 log 10 FFU/mL higher for the SA13/JFH1Core-NS5B compared to the original SA13/JFH1C3405G,A3696G (FIG. 18B). We generated 2nd passage stock viruses of all recombinants (data not shown) and sequenced their entire ORF. Peak infectivity titers in 2nd passage virus stocks were similar to those of 1st passage stocks (data not shown). Sequence analysis confirmed the presence of all the inserted mutations. Apparently, all the adapted SA13/JFH1 viruses were genetically stable during two passages since no further adaptive mutations had been acquired.

We noted that during infectivity titration of both transfection and infection supernatants, individual SA13/JFH1Core-NS5B foci appeared to be larger than individual SA13/JFH1C3405G,A3696G foci. By measuring the area of all individual foci for these two viruses in both transfection (FIG. 18C, top panel) and infection (FIG. 18C, bottom panel), we found that SA13/JFH1Core-NS5B foci were significantly bigger in size than SA13/JFH1C3405G,A3696G foci (transfection: p=0.0001 and infection: p<0.0001; Mann-Whitney non-parametric test) (FIG. 18C). This indicated that cell-to-cell transmission could have contributed to the accelerated spread of SA13/JFH1Core-NS5B.

Spread kinetics and peak infectivity titers were similar between SA13/JFH1p31/C5 and SA13/JFH1Core-NS5B. To more accurately compare spread kinetics and peak HCV infectivity titers between the different virus stocks generated, we did two infection studies using 2nd passage SA13/JFH1C3405G,A3696G, SA13/JFH1C3405G,A3696G, A3042G, SA13/JFH1p7-NS5B and SA13/JFH1Core-NS5B supernatants, SA13/JFH1p31/C5 and SA13/JFH1p23/UoB supernatants, and J6/JFH1 control supernatant. To increase accuracy, three aliquots of each virus stock were titrated in three independent assays using the same stock of Huh7.5 cells (data not shown). Mean infectivity titers were determined for all stocks and used to calculate the dose needed to infect Huh7.5 cell cultures at MOIs of 0.003 and 0.0003, respectively. Supernatants were collected as indicated until cultures were terminated due to massive cell death. HCV infectivity titers were determined for all collected supernatants (FIG. 19).

In both experiments, the J6/JFH1 control virus reached peak infectivity titers of 4.8 and 4.9, similar to what is typically observed for this recombinant (FIG. 19, FIG. 23). In the 0.003 MOI experiment, SA13/JFH1C3405G,A3696G peak infectivity titer was 5.0 log 10 FFU/mL (FIG. 23). We observed minor differences in spread kinetics and peak titers between SA13/JFH1C3405G,A3696G, SA13/JFH1C3405G,A3696G,A3042G and SA13/JFH1p7-NS5B (FIG. 4A and FIG. 23). SA13/JFH1Core-NS5B, SA13/JFH1p31/C5, and SA13/JFH1p23/UoB all spread faster than SA13/JFH1C3405G,A3696G (FIG. 19A). Furthermore, differences in peak infectivity titers between 0.6 and 0.9 log 10 FFU/mL were observed between SA13/JFH1C3405G, A3696G and SA13/JFH1Core-NS5B, SA13/JFH1p31/C5, and SA13/JFH1p23/UoB (FIG. 23). A similar pattern was observed in the 0.0003 MOI experiment. Differences in spread kinetics were more pronounced with only SA13/JFH1Core-NS5B and SA13/JFH1p31/C5 infectivity titers being above cut-off at day 1 (FIG. 19B). Peak titers were comparable to the titers observed in the 0.003 MOI experiment (FIG. 23). Again, SA13/JFH1Core-NS5B and SA13/JFH1p31/C5 viruses grew to similar peak infectivity titers, suggesting that the panel of 14 putative adaptive mutations encoding 13 aa changes conferred faster spread and increase in peak infectivity titers compared to SA13/JFH1C3405G, A3696G (FIG. 19B, FIG. 23).

Adaptive mutations might enhance HCV assembly. Since the introduced adaptive mutations conferred increased viral fitness, we investigated which step of the viral life cycle was affected. To this aim, we performed single-cycle virus production assays in CD81-deficient S29 cells. S29 cells were transfected with either SA13/JFH1C3405G,A3696G, SA13/JFH1C3405G,A3696G,A3042G, SA13/JFH1p7-NS5B, or SA13/JFH1Core-NS5B; J6/JFH1 or J6/JFH1-GND were included as controls. At 48 hours post transfection, we determined intra- and extracellular Core levels (FIG. 20A) and infectivity titers (FIG. 20B). Core levels were normalized to intracellular Core levels determined 4 hours post transfection. We observed no major differences in intracellular Core levels suggesting that HCV replication/translation was not affected by the putative adaptive mutations present in any of the tested viruses (FIG. 20A). For extracellular Core levels we observed a trend towards higher Core levels for SA13/JFH1p7-NS5B and SA13/JFH1Core-NS5B (FIG. 20A). This indicated that assembly/release might be enhanced by the putative adaptive mutations in these two viruses. S29 intracellular infectivity titers were ~1 log 10 FFU/well higher for SA13/JFH1p7-NS5B and SA13/JFH1Core-NS5B compared to SA13/JFH1C3405G, A3696G (FIG. 20B).

This supported the Core data described above, suggesting enhanced assembly. As observed for infections in Huh7.5 cells, S29 extracellular infectivity titers were ~1 log 10 FFU/mL higher for SA13/JFH1p7-NS5B and SA13/JFH1Core-NS5B compared to SA13/JFH1C3405G, A3696G (FIG. 20B), supporting that assembly of HCV particles was enhanced. The ratio between intra- and extracellular infectivity titers were comparable between all viruses (FIG. 20B), indicating that the putative adaptive mutations primarily enhanced HCV assembly and not release of virus particles. The specific infectivity based on the ratio between extracellular Core and -infectivity titers were higher for SA13/JFH1p7-NS5B and SA13/JFH1Core-NS5B compared to SA13/JFH1C3405G,A3696G suggesting that more complete infectious virus particles were produced from these cultures (data not shown).

Increased sensitivity of SA13/JFH1Core-NS5B to neutralization with purified patient IgG. The influence of envelope mutations on the sensitivity to neutralizing antibodies has previously been described. Since the SA13/JFH1Core-NS5B recombinant contains 4 mutations in the structural genes, with two mutations in the envelope glycoproteins, we investigated the neutralization sensitivity of this virus compared to SA13/JFH1C3405G,A3696G and SA13/JFH1p7-NS5B, using IgG purified from patient H serum taken 29 years after the acute infection.

We observed that SA13/JFH1C3405G,A3696G and SA13/JFH1p7-NS5B were similarly neutralized, suggesting that the panel of nonstructural mutations present in SA13/JFH1p7-NS5B did not confer increased sensitivity to neutralization (FIG. 21). However, SA13/JFH1Core-NS5B showed increased sensitivity to neutralization, never reaching less than 50% neutralization even at the lowest IgG concentration tested, suggesting that either one or several of the structural mutations altered sensitivity to neutralization (FIG. 21).

Serum-free culture increases peak infectivity titers of SA13/JFH1p31/C5 virus. We have developed a novel serum-free cell culture system based on adenovirus expression medium (AEM), which consistently produces higher titers than regular cultures (Mathiesen et al., data submitted for publication). To test whether the infectivity titers of our high-titer virus stock SA13/JFH1p31/C5 could be increased further, we performed a serum-free culture (passage 32) of this virus as described in Materials and Methods. We recorded peak titers of 7.2 log 10 FFU/mL in supernatants collected from Huh7.5 cells cultured in AEM. Furthermore, titers of ~6 log 10 FFU/mL could be collected until at least day 15 post infection when cultures were terminated (FIG. 22). Thus, using serum-free culture conditions, peak infectivity titers were increased, consistent with what we typically observe for AEM cultured HCVcc (see example 1).

Discussion

In this study, we describe further adaptation of an HCV genotype 5a JFH1-based Core-NS2 recombinant (SA13/JFH1C3405G,A3696G) by 96-well plate based serial passage. Serial passage of this virus resulted in the generation of a high-titer virus (SA13/JFH1p31/C5). We identified a panel of 14 novel putative adaptive mutations conferring 13 aa changes. When introduced back into the original SA13/JFH1C3405G,A3696G construct generating SA13/JFH1Core-NS5B, these mutations caused accelerated viral spread and increased HCV infectivity titers comparable to SA13/JFH1p31/C5, possibly due to enhanced HCV assembly and entry. SA13/JFH1Core-NS5B, with envelope mutations, showed an increased sensitivity towards neutralization with purified patient serum IgG compared to the SA13/JFH1C3405G,A3696G and SA13/JFH1p7-NS5B constructs, containing no envelope mutations. Finally, we demonstrated that infectivity titers of SA13/JFH1p31/C5 could be further increased by employing a novel serum-free Huh7.5 cell culture system.

The error rate of the HCV RNA-dependent RNA polymerase NS5B has been determined to be ~$2.5 \times 10^{-5}$ mutations per nucleotide per genome replication. Thus, serial passage of HCV will result in the emergence of quasispecies with possible fitness advantages compared to the original virus genome. By natural selection, it follows that if a fitter genome is generated, this will over time become the dominant quasispecies in the cell culture. For most HCVcc Core-NS2 JFH1-based recombinants, adaptive mutations were needed for efficient viral growth. Others have described further adaptation of JFH1 or J6/JFH1 using serial passage. For JFH1, the authors were able to generate adapted stocks displaying peak infectivity titers between 5 to 7 log 10 FFU/mL or 5 to 6 log 10 50% tissue culture infectious dose (TCID50)/mL. For J6/JFH1, the authors were apparently able to generate a virus stock with a peak titer of 8 log 10 TCID50/mL, although this data was not shown, while others have reported high-titer J6/JFH1 variants growing to titers of ~6.5 log 10 TCID50/mL.

In order to perform high throughput serial passage, we employed 96-well plate based serial passage (FIG. 15, arrows). By testing 6 (corresponding to 16%) of the serially passaged cultures, we were able to generate SA13/JFH1p31/C5 with an infectivity titer of 6.7 log 10 FFU/mL. Thus, our peak titers was in the upper range of what was previously reported. It is worth noting that direct comparisons of infectivity titers between different laboratories is made difficult by different methodologies used for titer determination (FFU vs. TCID50), as well as variation between Huh7.5 cells cultured in different laboratories.

In the following 32nd passage, we were not able to reproduce an equally high titer (FIG. 17); however, in a 32nd passage stock generated at a later stage, we observed peak titers of 6.6 log 10 FFU/mL (data not shown). Furthermore, several independent titrations of SA13/JFH1p31/C5 confirmed the infectivity titer to be 6.5-6.7 log 10 FFU/mL (data not shown). Thus, it is possible that slight differences in specific culture conditions might have favoured virus production. It is interesting that most adaptation studies describe generation of virus stocks with peak titers in the range of 6 log 10 FFU/mL or TCID50/mL.

Possibly, this represents the maximum HCV output that Huh7 and derived cell lines are capable of. The fact that we were able to increase the infectivity titer of our fittest JFH1-based Core-NS2 recombinant suggests that 96-well plate based serial passage might be used to further adapt low-titer recombinants such as those of epidemiologically important genotypes 1b (J4/JFH1) and 4a (ED43/JFH1), which might be important for future vaccine development as well as for biophysical studies.

Figure 18:
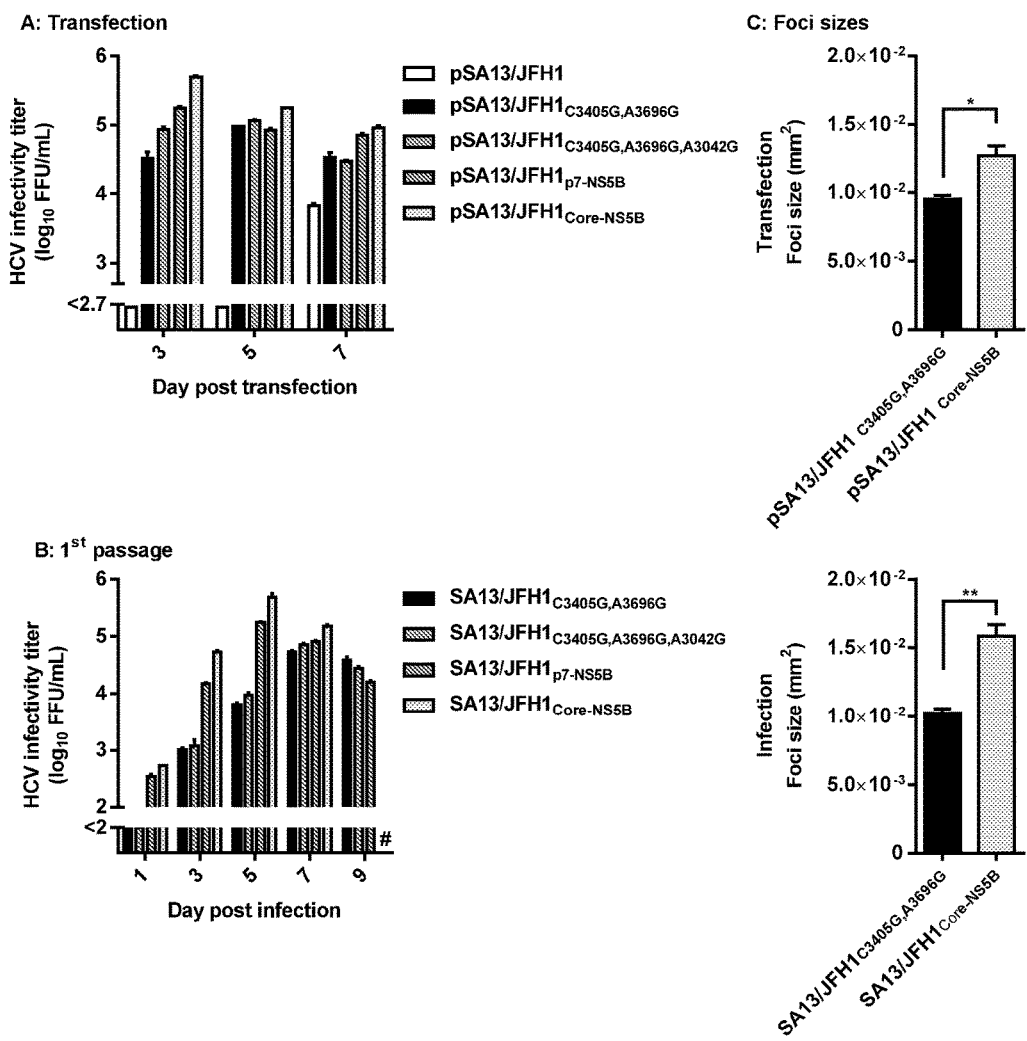

Interestingly, when comparing the consensus sequence of the independently adapted serial passaged SA13/JFH1p23/UoB stock to the SA13/JFH1p31/C5 stock, we discovered a single common NS2 mutation (A3042G) (FIG. 17). This NS2 mutation alone did not confer increased viral fitness compared to SA13/JFH1C3405G,A3696G (FIGS. 18, 19 and 20).

We generated SA13/JFH1p7-NS5B and SA13/JFH1Core-NS5B by introducing panels of 10 mutations, conferring 9 aa changes in the nonstructural proteins (FIG. 17, dark shaded), or a total of 14 mutations, conferring 13 aa changes in structural- and nonstructural proteins, respectively (FIG. 17, shaded). To our knowledge, only one of these mutations has previously been described; the NS5A mutation T7138C (L2266P) was previously described as a minor quasispecies for the genotype 4a Core-NS2 recombinant ED43/JFH1, however, any potential function of this specific change was never investigated.

More mutations were found in NS5A than in any other HCV protein (FIG. 17). This is in accordance with several other studies describing an accumulation of mutations in NS5A. Interestingly, both constructs showed increased viral fitness after transfection and during a 1st passage experiment, although the complete panel of 14 nucleotide mutations was needed to generate the fittest construct (FIGS. 18A and B). By investigating HCV spread kinetics following infections at different MOIs, we observed that the SA13/JFH1Core-NS5B construct displayed similar spread kinetics and grew to similar peak titers as the SA13/JFH1p31/C5 virus stock, suggesting that the panel of 14 nucleotide mutations could confer a similar increase in infectivity titers as seen for SA13/JFH1p31/C5 (FIG. 19). SA13/JFH1C3405G,A3696G has been shown to be capable of high levels of cell-to-cell spread compared to other Core-NS2 JFH1-based recombinants. Interestingly, foci were significantly bigger for SA13/JFH1Core-NS5B compared to SA13/JFH1C3405G,A3696G following both transfection and infection (FIG. 19C), suggesting a further increase in cell-to-cell spread ability of SA13/JFH1Core-NS5B. Thus, further studies of cell-to-cell spread will determine whether this phenomenon plays a pronounced role for the increased viral fitness observed for SA13/JFH1Core-NS5B.

In several adaptation studies, the authors were able to identify specific aa changes conferring the increase in viral fitness. Enhancement of viral fitness can occur at different stages of the viral life cycle: entry, replication, assembly and release. Several of the adaptive mutations described previously were present in E2. Since E2 apparently mediates interaction between HCV and host cell surface receptors, these mutations might be entry enhancing as previously described, although E2 apparently also plays a role during assembly.

Mutations were also detected in nonstructural proteins, suggesting that these enhanced virus production. Although previously reported mutations were detected in all nonstructural proteins, specifically mutations found in p7, NS2, NS4B and NS5A were suggested to mediate increased virus production; for some of these, virus assembly was suggested to be affected. Using single cycle virus production assays in S29 cells, we observed that HCV assembly might be affected by the putative adaptive mutations present in both SA13/JFH1p7-NS5B and SA13/JFH1Core-NS5B (FIG. 20). Infectivity titers for SA13/JFH1Core-NS5B were slightly higher compared to SA13/JFH1p7-NS5B, suggesting that the 4 mutations in the structural proteins conferred a further increase in viral fitness. Since the extracellular Core level was slightly increased for SA13/JFH1Core-NS5B compared to SA13/JFH1p7-NS5B, these data indicate that the effect of the structural mutations was also assembly enhancing. The common NS2 mutation A3042G alone did not enhance or reduce viral fitness at any step of the viral life cycle (FIG. 20), supporting the data obtained from transfections and infections of Huh7.5 cells (FIGS. 18 and 19).

It is possible that systematic mutational analysis of these 14 putative adaptive mutations would reveal some residues as major determinants of increased viral fitness as previously described in other studies. Since most of the mutations described in this study appear to be novel, it is difficult to predict specific residues responsible for increased viral fitness. This would require extensive reverse genetics studies that we consider outside the scope of this study.

Mutations in the viral envelope glycoproteins have previously been associated with altered sensitivity to neutralizing antibodies. Indeed, SA13/JFH1Core-NS5B showed increased sensitivity to neutralizing IgG purified from patient serum compared to SA13/JFH1C3405G,A3696G and SA13/JFH1p7-NS5B without structural mutations (FIG. 21). The distribution of the 4 structural mutations can be seen in FIG. 17 (light grey shaded). Since the two Core residues, at which mutations occurred, are unlikely to be exposed to neutralizing antibodies, it is likely that the E1 mutation G1043C, the E2 mutation A1493C, or both mutations were responsible for the increased sensitivity to neutralization. The A1493C mutation confers a threonine to proline change at aa position 385 (FIG. 17).

This mutation is positioned in the HVR1, a region of high sequence variability; however, at aa position 385, threonine is highly conserved amongst all HCV genotypes. Interestingly, position 385 is a putative glycosylation site for O-linked glycosylation. Alanine substitution at this position was previously shown to confer increased sensitivity to neutralization of HCV pseudo-particles displaying envelope proteins of the genotype 1a isolate H77 with genotype 1-5 patient serum. Deletion of HVR1 in HCVcc particles has previously been shown to be associated with increased sensitivity to neutralizing antibodies; possibly, deletion of HVR1 abrogates a shielding mechanism revealing highly immunogenic epitopes.

Since no known neutralizing epitopes have been described in connection with any of the envelope mutations, it is possible that increased neutralization sensitivity is caused by the A1493C mutation disrupting glycan-mediated shielding. Thus, this single aa change might mediate the same effect as deletion of the complete HVR1. Deletion of HVR1 was also associated with a change in HCVcc density, suggested to be due to altered lipoprotein association.

Thus, future studies will focus on the density- and neutralization profile of mutants of the SA13/JFH1Core-NS5B recombinant missing either or both envelope mutations. Furthermore, constructs where these mutations have been introduced into the original SA13/JFH1C3405G,A3696G construct should be investigated. Such mutational studies will help determining the specific role of these positions in HCV neutralization.

Finally, we applied a novel serum-free cell culture system developed in our laboratory for vaccine development studies (see example 1) to the SA13/JFH1p31/C5 virus stock. From the AEM culture, we were able to generate a virus stock with a peak titer of 7.2 log 10 FFU/mL, representing the highest infectivity titer recorded in our laboratory (FIG. 22), thus demonstrating the potential for combining these methods for production of high-titer HCVcc.

In summary, we have demonstrated high-throughput adaptation of JFH1 based HCVcc recombinants using 96-well plate based serial passage. The serial passage-generated stock SA13/JFH1p31/C5 displayed accelerated spread kinetics and grew to higher peak infectivity titers compared to SA13/JFH1C3405G,A3696G. A panel of 14 putative adaptive mutations, causing 13 aa changes, could confer this increased viral fitness, possibly by enhancing HCV assembly and entry. Four of the 14 nucleotide mutations were in structural genes and might confer an increase in sensitivity to neutralizing antibodies. Application of a novel serum-free culture system further increased infectivity titers. Production of high-titer virus stocks is of great importance for research aimed at vaccine development and biophysical characterization that currently involves production of great volumes of HCVcc followed by cumbersome concentration procedures.

Thus, we believe that 96-well plate based serial passage of JFH1-based HCVcc recombinants might facilitate high-throughput improvement of the HCVcc system in order to produce sufficient amounts of virus particles for such studies.

Example 3—Multistep Procedure for Virus Purification, Concentration and Inactivation A) Multistep Procedure for Virus Purification and Concentration Using a multistep procedure involving cross-flow filtration, ultracentrifugation and chromatography, we are able to achieve >99% pure virus, and more than 1000-fold upconcentration. Thus, the described methods result in production of a virus vaccine candidate stock.

We first established Method 1. A typical experiment is depicted in FIG. 24.

Starting material for this method is typically up to 10 L of HCV containing serum-free cell culture supernatant from Huh7.5 cell cultures infected with the adapted genotype 5a (isolate SA13) Core-NS2 JFH1-based recombinant. We first carried out cross-flow filtration using Vivaflow filters (Sartorius) with 100 kDa cut-off for purification from low-molecular proteins and significant up-concentration. We then carried out 3-cushion iodixanol ultracentrifugation using 3 cushions with different percentages of iodixanol for purification and further up-concentration. In this step, viral particles can be concentrated and separated according to their buoyant density. At equilibrium, viruses will be found at a certain density. We collect 3 fractions and use the middle one. Next, we carried out ultracentrifugation pelleting for purification from iodixanol and up-concentration. This step, associated with a relatively low recovery is required to remove iodixanol and to be able to proceed to the next step. We then carried out iodixanol gradient centrifugation using a continuous gradient (10-40% iodixanol) for purification. At equilibrium, viruses will be found at a certain density. We collected 18 fractions, and further processed the 3 fractions that contain most virus. At last, we carried out sephadex chromatography for purification from iodixanol, which interfers with UV irradiation-based inactivation.

Compared to Method 2, Method 1 had relatively low recovery and importantly, input volume (HCV containing cell culture supernatant) was limited to 10 L.

Thus, we established Method 2. A typical experiment is depicted in FIG. 25.

In the experiment shown, starting material was 8.7 L, however, with this method upscaling to for example close to 1000 L should be possible. Another advantage of Method 2 is increased recovery compared to Method 1.

Starting material for this method is typically up to 1000 L of virus containing serum-free cell culture supernatant from Huh7.5 cell cultures infected with the adapted genotype 5a (isolate SA13) Core-NS2 JFH1-based recombinant. We first carried out cross-flow filtration using mPES MiniKros® Sampler Filter Modules 20 cm with 500 kDa cut-off (SpectrumLabs) for purification from low-molecular proteins and significant up-concentration. Importantly, by introduction of these filters instead of filters used in Method 1, viral recovery could be significantly increased. To process greater volumes than in the experiment shown in FIG. 25, MiniKros® Filter Modules, mPES KrosFlo® Filter Modules, or KrosFlo® Max Filter Modules might be used. We then carried out 3-cushion iodixanol ultracentrifugation using 3 cushions with different percentages of iodixanol for purification and further up-concentration. In this step, viral particles can be separated according to their buoyant density. At equilibrium, viruses will be found at a certain density. We collect 3 fractions and use the middle one. Next, we carried out small-scale cross-flow filtration using mPES MicroKros® Modules (Spectrum labs) for purification from iodixanol and up-concentration. Importantly, by introduction of this step instead of ultracentrifugation pelleting (Method 1), viral recovery could be significantly increased. We then carried out iodixanol gradient centrifugation using a continuous gradient (10-40% iodixanol) for purification. At equilibrium, viruses will be found at a certain density. We collected 18 fractions, and further processed the 3 fractions that contain most virus. At last, we carried out sephadex chromatography for purification from iodixanol, which interfers with UV irradiation-based inactivation.

Thus, when using equivalent starting material, with Method 2 a 10-fold higher yield was obtained compared to Method 1. In addition, it is expected that it is possible to increase the input volume, when using Method 2, by up to 100-fold compared to Method 1.

B) Virus Inactivation by UV Irradiation

The UV lamp was turned on 5 min in advance to ensure maximum intensity. Virus vaccine candidate stock is placed in 6-well plates and irradiated for 15 to 35 min, shaking every 5 min. Alternatively, other UV emitting devices, such as UV boxes might be used. To confirm inactivation, the same volume that might be used for vaccination, is inoculated in replicate Huh7.5 cell cultures. These cultures are followed for 3 weeks with immunostaining for HCV antigen. Inactivation is confirmed, if no positive cells are observed. Replicate positive control cultures are infected with non-inactivated genotype 5a Core-NS2 JFH1-based recombinant. Replicate negative cultures are also maintained throughout the experiment.

UV irradiation damages the genomic material of the virus. It is of advantage, that the viral proteins and specifically the envelope proteins are expected to be largely unaffected by this method. Thus, native epitopes might be presented on UV-inactivated viral particles. This is in contrast to other methods, for example paraformaldehyde inactivation, during which proteins are cross-linked and undergo profound conformation changes. Another advantage of UV-irradiation is that following this step no additional purification is required. This is, however, the case if chemicals such as paraformaldehyde are used for viral inactivation. From electron microscopy we have found evidence suggesting that the UV-inactivated vaccine antigen is still comprised of what appears to be whole enveloped HCV particles.

Example 4—Increased Sensitivity to Neutralization with Purified Patient IgG, Human Monoclonal IgG and sCD81-LEL is Caused by a Putative Adaptive aa Change in E2

Materials and Methods:

Neutralization assays. Huh7.5 cells (7,000 cells/well) were seeded onto poly-D-lysine coated 96-well plates. Antibody assays: The following day, IgG purified from serum from genotype 1a infected Patient H, taken 29 years after acute infection (H06) or monoclonal antibodies AR3A and AR4A, were diluted in complete DMEM as specified and mixed 1:1 with 400 FFU of the relevant viruses. IgG-virus mixes were incubated at 37° C. for 1 hour before being added onto the pre-plated cells. Cells were incubated with IgG-virus mixes for 3 hours. After incubation, cells were washed in PBS and complete DMEM was added to all wells. sCD81-LEL assay: The following day, soluble CD81 large-extracellular-loop (sCD81-LEL) was diluted in complete DMEM as specified and mixed 1:1 with 300 FFU of the relevant viruses. sCD81-LEL-virus mixes were incubated at 37° C. for 1 hour before being added onto the pre-plated cells. Cells were incubated with sCD81-LEL-virus mixes for 3 hours. After incubation, cells were washed in PBS and complete DMEM was added to all wells. Antibody and sCD81-LEL assays: Cells were fixed 48 hours post infection in ice-cold methanol and HRP-stained for HCV NS5A as described. Single HCV NS5A positive cells were counted automatically as described. The % neutralization was calculated by relating counts of experimental wells to the mean count of six replicate wells with untreated control virus. Following logarithmic transformation of X-values, variable-slope sigmoidal dose-response curves [$Y = Bottom + (Top - Bottom)/(1 + 10^{(Log10EC50-X) \times HillSlope)}$] were fitted using GraphPad Prism 6.0 software. A "Bottom" constraint of 0 and a "Top" constraint of 100 were introduced, and median inhibitory concentrations (IC50) were calculated using GraphPad Prism 6.0. Recombinants with envelope mutations were propagated in Huh7.5 cells. For all virus stocks used for neutralization assays we confirmed that the entire ORF sequence, determined by direct sequencing, was identical to the plasmid sequence.

Results:

Increased sensitivity to neutralization with purified patient IgG, human monoclonal IgG and sCD81-LEL is caused by a putative adaptive aa change in E2. The influence of envelope mutations on the sensitivity of extracellular HCV to neutralizing antibodies has previously been described. Thus, we investigated if the adaptive aa changes present in SA13/JFH1Core-NS5B influenced virus sensitivity to neutralization compared to SA13/JFH1orig. As neutralizing reagent, we used a well-defined IgG purified from patient H serum taken 29 years after the acute infection. We observed a significant increase (P=0.0003) in the neutralization sensitivity of SA13/JFH1Core-NS5B with a median inhibitory concentration (IC50) of 0.27 µg/mL compared to SA13/JFH1orig with an IC50 value of 1.4 µg/mL (FIGS. 26A and B; FIG. 27). Thus, mutations in SA13/JFH1Core-NS5B apparently caused increased neutralization sensitivity. To identify the mutation responsible for the increased neutralization sensitivity, we mutated residues at aa positions 235 in E1 and 385 in E2 singly and in combination. Peak infectivity titers of these recombinants were 5.4-5.6 log 10 FFU/mL. Interestingly, we observed significantly increased neutralization sensitivity (P=0.0004) when inserting the T385P in E2 of SA13/JFH1orig (SA13/JFH1orig+E2; FIG. 26A; FIG. 27). The IC50 value was determined to be 0.28 µg/mL, similar to SA13/JFH1Core-NS5B. Insertion of the E1 mutation V235L (SA13/JFH1orig+E1) did not affect neutralization sensitivity (P=0.65), whereas insertion of both mutations (SA13/JFH1orig+E1+E2) resulted in significantly increased neutralization sensitivity (P=0.0002) (FIG. 26A; FIG. 27), suggesting that the E2 mutation was responsible for the neutralization phenotype. We confirmed these findings by reverting the E1 and E2 mutations in SA13/JFH1Core-NS5B. Peak infectivity titers of these recombinants were 5.9-6.1 log 10 FFU/mL. When reverting P385T in E2 of SA13/JFH1Core-NS5B (SA13/JFH1Core-NS5B, revE2), we observed significantly decreased neutralization sensitivity (P<0.0001) compared to SA13/JFH1Core-NS5B (FIG. 26B; FIG. 27). Reversion of the E1 mutation L235V (SA13/JFH1Core-NS5B,revE1) did not affect neutralization sensitivity (P=0.68), whereas reversion of both mutations (SA13/JFH1Core-NS5B,revE1,E2) resulted in significantly decreased neutralization sensitivity (P<0.0001) (FIG. 26B; FIG. 27). Thus, an aa change at position 385 caused increased sensitivity to neutralizing patient IgG.

To investigate whether the mutation at position 385 would affect sensitivity against well-defined human monoclonal antibodies, we performed neutralization assays using previously described antibodies AR3A (FIG. 26C) and AR4A (FIG. 26D). Both AR3A and AR4A target conformational epitopes; whereas AR3A binds an epitope on E2 and blocks E2 binding to CD81, AR4A binds only the full E1/E2 heterodimer and does not block E2 binding to CD81. As above, SA13/JFH1Core-NS5B,revE2 was significantly less sensitive to neutralization with both AR3A and AR4A (P=0.0019 and P<0.0001 respectively) with IC50 values of 0.07 µg/mL for AR3A and 0.16 µg/mL for AR4A compared to 0.027 µg/mL (AR3A) and 0.02 µg/mL (AR4A) for SA13/JFH1Core-NS5B (FIGS. 26C and D; FIG. 27). For SA13/JFH1Core-NS5B,revE1, we determined IC50 values of 0.022 µg/mL for AR3A and 0.017 µg/mL for AR4A, similar to that of SA13/JFH1Core-NS5B (P=0.46 for both), whereas SA13/JFH1Core-NS5B,revE1,E2 with IC50 values of 0.075 µg/mL for AR3A and 0.15 µg/mL for AR4A was significantly less sensitive to neutralization (P=0.0004 and P<0.0001 respectively) compared to SA13/JFH1Core-NS5B (FIGS. 26C and D; FIG. 27). Finally, we investigated whether the CD81 binding region of E2 was affected by the mutation at position 385 by neutralizing SA13/JFH1Core-NS5B and SA13/JFH1Core-NS5B,revE2 with sCD81-LEL. Hypervariable region 1 (HVR1)-deleted SA13/JFH1ΔHVR1 was included as control, since it was reported that HVR1 deletion exposed the CD81 binding site of E2. Interestingly, SA13/JFH1Core-NS5B,revE2, with an IC50 value of 0.9, was significantly less sensitive to neutralization with sCD81-LEL compared to SA13/JFH1Core-NS5B with an IC50 value of 0.2 (P<0.0001) and SA13/JFH1ΔHVR1 with an IC50 value of 0.32 (P<0.0001) (FIG. 26E).

It should be noted that neutralizing antibodies and sCD81-LEL were pre-incubated with the virus for 1 hour before the mix was added onto Huh7.5 cells for a 3 hour attachment phase and subsequently removed. Thus, differences in the use of cell-to-cell transmission between viruses as described above would not influence the results of these assays.

Discussion:

Due to the lack of immunological pressure in Huh7.5 cells, fitness enhancing mutations may occur at positions that affect sensitivity to neutralization. E.g. aa changes in the viral envelope glycoproteins have previously been associated with altered sensitivity to neutralizing antibodies. The role of changes to the envelope glycoproteins in respect to HCV immunogenicity remains to be fully elucidated. However, immunogenicity studies of other viruses, such as human immunodeficiency virus, respiratory syncytial virus and herpes simplex virus 2 suggest that such changes can be of importance in order to expose otherwise non-accessible neutralizing epitopes. Indeed, we observed that the E2 aa change T385P conferred significantly increased sensitivity to neutralization by IgG purified from chronic phase patient serum (FIG. 26 and FIG. 27). Alanine substitution at this position was previously shown to confer increased neutralization sensitivity to HCV pseudo-particles using different patient sera. Thus, our results using the HCVcc system support these previous findings in the HCVpp system. It should be noted that we observed an apparent increased resistance towards neutralizing IgG when comparing IC50 values of SA13/JFH1orig and SA13/JFH1Core-NS5B, revE2 (FIG. 27). In a repeat experiment, we did not observe this difference in IC50, while the difference between SA13/JFH1orig and SA13/JFH1Core-NS5B was similar (data not shown). Thus, this apparent resistance was most likely due to variation in the assay shown in FIG. 26 FIG. 27. We further demonstrated that mutation at position 385 confers a significant increase in sensitivity to neutralization by well-defined human monoclonal antibodies AR3A and AR4A (FIG. 26 and FIG. 27). Both antibodies target conformational epitopes in E2 (AR3A) or E1E2 (AR4A), neither epitope overlapping with position 385. Furthermore, the CD81 binding site of E2 seemed to be more accessible in SA13/JFH1Core-NS5B, as this virus was significantly more sensitive to neutralization with sCD81-LEL compared to SA13/JFH1Core-NS5B,revE2 (FIG. 26E). Thus, our findings suggest that mutation at position 385 might cause a conformational change in the E1E2 heterodimer, or that position 385 is involved in shielding of both the AR3A and AR4A epitopes, and the CD81 binding site of E2. Supporting the latter hypothesis is the observation that position 385 is a putative site for O-linked glycosylation. Thus, even though O-linked glycans have never been implicated in shielding epitopes, it is possible that the T385P mutation disrupts glycan-mediated shielding of immunogenic epitopes. Collectively, these data suggest a novel role for O-linked glycosylation at position 385 in the shielding of defined neutralizing conformational epitopes, including epitopes involving the CD81 binding site of E2.

Example 5—Adaptive Mutations do not Affect the Buoyant Density of Infectious HCVcc Particles Materials and Methods:
Equilibrium density gradient ultracentrifugation. Semicontinuous 10-40% iodixanol gradients were prepared as previously described. HCVcc containing supernatants of the indicated viruses were concentrated using Amicon 100 kDa centrifugation filters (Millipore). A final volume of ~200 µL concentrated supernatant was loaded on top of each gradient. The samples were ultracentrifugated at 151.000× relative centrifugal force (RCF) for 18 hours at 4° C. using a Beckman SW-41 rotor mounted in a Beckman XL-70 ultracentrifuge. Following ultracentrifugation, fractions of ~550 µL were collected from the bottom of the tube. For determination of density, portions of 400 µL of each fraction were weighed (model SI-114; Denver Instruments). Fraction infectivity titers were determined as described above. Iodixanol-containing fractions were diluted to contain≤10% iodixanol before titration.

Results:
Adaptive mutations do not affect the buoyant density of infectious HCVcc particles. Envelope mutations and deletion of HVR1 from HCVcc have previously been reported to change HCVcc particle density. To determine whether the adaptive mutations identified in this study conferred any such changes, we subjected SA13/JFH1orig, SA13/JFH1p7-NS5B, SA13/JFH1Core-NS5B, SA13/JFH1orig,E2 and SA13/JFH1Core-NS5B,revE2 to equilibrium density ultracentrifugation using iodixanol gradients as described in Materials and Methods and measured infectious virus in all fractions. We included previously described SA13/JFH1ΔHVR1 as a control, since this virus was previously demonstrated to display an altered density profile. Overall, mutant viruses displayed a similar density profile with infectious virus present at densities of 1.01-1.13 g/mL (FIG. 28). The SA13/JFH1ΔHVR1 virus displayed a characteristic density profile with a single peak at ~1.10 g/mL (FIG. 28), in accordance with previous observations. Thus, the aa changes in the structural proteins described in this study did not seem to affect the buoyant density of infectious HCVcc particles.

Discussion:
Amino acid changes in E2, as well as deletion of HVR1 have previously been associated with changes in HCVcc biophysical properties, suggested to be due to altered lipoprotein association. Since one of the main applications of adapted HCVcc recombinants would be to facilitate morphological studies of the virus particle, it is of high importance to determine whether the biophysical properties of the virus changes with the introduction of putative adaptive aa changes in the structural proteins. We did not observe any differences in HCVcc particle density between SA13/JFH1orig, SA13/JFH1p7-NS5B, SA13/JFH1Core-NS5B, SA13/JFH1orig,E2 and SA13/JFH1Core-NS5B,revE2 (FIG. 28), suggesting that the E2 mutation at position 385 described in this study did not affect the morphology of the virus particles. It is possible that minor differences in the composition of the virus particles would become apparent using more sensitive methods, such as mass spectrometry, however, such analyses were considered outside the scope of this study.

Example 6—Adaptive Mutations do not Affect Usage of HCV eEntry Receptors CD81 and SR-BI Materials and Methods:
Receptor blocking assays. Huh7.5 cells (7,000 cells/well) were seeded onto poly-D-lysine coated 96-well plates. The following day, Purified Mouse Anti-Human CD81 primary antibody (JS-81 [BD Biosciences]) or anti-SR-BI primary antibody was diluted in complete DMEM as specified in the figure legend, and added to the cells for 1 hour. Following incubation, 300 FFU of the indicated viruses were added for 3 hours. Following incubation, cells were washed in PBS and complete DMEM was added to all wells. Cells were incubated and fixed 48 hours post infection in ice-cold methanol and HRP-stained for HCV NS5A as described above with the following modifications: Following fixation, cells were washed twice in PBS supplemented with 0.1% Tween-20 (Sigma-Aldrich) (termed PBS-Tween), and 3% $H_2O_2$ were added for 5 minutes at room temperature. Cells were washed twice in PBS-Tween, and 300 µL of PBS supplemented with 1% bovine serum albumin (BSA) and 0.2% skim milk (Blocking buffer) was added for 1 hour at room temperature. Following incubation, the blocking buffer was removed and 10 µg of AffiniPure fragment antigen binding (Fab Fragment) Goat Anti-Mouse IgG (H+L) (Jackson Immunoresearch) were added to the cells at 100 µg/mL and incubated for 1 hour at room temperature. Following incubation, cells were washed twice in PBS-Tween and stained for HCV NS5A as described above. Single HCV NS5A positive cells were counted automatically as described. The % blocking was calculated by relating counts of experimental wells to the mean count of eight replicate wells with untreated control virus. Following logarithmic transformation of X-values, variable-slope sigmoidal dose-response curves [Y=Bottom+(Top−Bottom)/(1+ $10^{(Log10EC50-X) \times HillSlope)}$] were fitted using GraphPad Prism 6.0 software. A "Bottom" constraint of 0 was introduced. For CD81 blocking, a "Top" constraint of 100 was introduced. For SR-BI blocking, maximum blocking rates, the Y values at the top plateaus of the fitted curve were calculated using GraphPad Prism 6.0. Recombinants with envelope mutations were propagated in Huh7.5 cells. For all virus stocks used for blocking assays we confirmed that the entire ORF sequence, determined by direct sequencing, was identical to the plasmid sequence.

Results:

Adaptive mutations do not affect usage of HCV entry receptors CD81 and SR-BI. HCV E2 is pivotal during entry as it interacts with several HCV co-receptors, including CD81 and SR-BI. Thus, E2 mutations might influence the usage of these co-receptors. We tested the ability of antibodies against CD81 and SR-BI to block entry of SA13/JFH1orig, SA13/JFH1p7-NS5B, SA13/JFH1Core-NS5B and SA13/JFH1Core-NS5B,revE2; for SR-BI blocking we included viruses SA13/JFH1Core-NS5B,revE1 and SA13/JFH1Core-NS5B,revE1,E2. We observed no major differences between the different viruses when blocking CD81 or SR-BI (FIG. 29). Thus, it seemed that the E2 mutation at position 385 did not affect interactions between E2 and CD81 or SR-BI.

Discussion:

While the T385P mutation had significant impact on neutralization sensitivity, it did not influence the usage of CD81 as all tested viruses were equally sensitive to antibody-mediated blocking (FIG. 29A). Thus, even though the CD81 binding site of E2 was more accessible for viruses carrying the T385P mutation, this did not influence the binding properties. Furthermore, unlike deletion of HVR1 which seems to reduce the usage of SR-BI for some genotypes the T385P mutation, which is the 2nd aa in HVR1 of E2, did not have any major effects on SR-BI usage (FIG. 29B).

The invention claimed is:

1. A method of obtaining a whole hepatitis C virus (HCV) vaccine candidate stock, the method comprising:
    a) providing a cell culture supernatant comprising HCV particles, wherein the cell culture is grown in an adenovirus expression medium, optionally supplemented with penicillin 100 U/mL and streptomycin 100 µg/mL,
    b) purifying or increasing the concentration of the HCV particles in the cell culture supernatant using cross-flow filtration,
    c) purifying or increasing the concentration of the product of step using 2-6 cushion iodixanol ultracentrifugations,
    d) collecting 2-8 fractions from step c), and selecting the fractions, which contain the most HCV particles,
    e) purifying or increasing the concentration of the selected fractions from step d) using ultracentrifugation pelleting or small-scale cross-flow filtration,
    f) purifying or increasing the concentration of the product of step e) using iodixanol gradient ultracentrifugation,
    g) collecting 10-35 fractions from the product of step f), and selecting the 2-7 fractions, which contain the most HCV particles,
    h) purifying or increasing the concentration of the selected 2-7 fractions from step g) using sephadex chromatography, and
    i) obtaining the whole HCV vaccine candidate stock.

2. The method according to claim 1, wherein the cell culture is grown on a surface, in a suspension, on beads, in cell factories or bioreactors.

3. The method according to claim 1, wherein the cells in the cell culture are Huh7.5 cells.

4. The method according to claim 1, wherein the cross-flow filtration utilizes hollow-fiber filters with molecular weight cut-offs of 500 kDa, 300 kDA, 200 kDa, 100 kDa, 70 kDa, 50 kDa, 30 kDa, 10 kDa, 5 kDa, 3 kDa, or 1 kDa, and optionally with different surface areas.

* * * * *